United States Patent
Kawai et al.

(12)

(10) Patent No.: US 6,417,202 B1
(45) Date of Patent: Jul. 9, 2002

(54) PYRIDYLPYRROLE COMPOUNDS USEFUL AS INTERLEUKIN- AND TNF ANTAGONISTS

(75) Inventors: Akiyoshi Kawai, Handa; Makoto Kawai; Yoshinori Murata, both of Chita-Gun; Junji Takada, Nagoya; Minoru Sakakibara, Chita-Gun, all of (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/214,573

(22) PCT Filed: Jun. 16, 1997

(86) PCT No.: PCT/IB97/00703

§ 371 (c)(1),
(2), (4) Date: Dec. 10, 1999

(87) PCT Pub. No.: WO98/02430

PCT Pub. Date: Jan. 22, 1998

(30) Foreign Application Priority Data

Jul. 11, 1996 (JP) .................................. PCT/IB96/00671

(51) Int. Cl.⁷ .................. A61K 31/4427; C07D 401/14
(52) U.S. Cl. ....................................... 514/333; 546/256
(58) Field of Search ........................... 514/333; 546/256

(56) References Cited

U.S. PATENT DOCUMENTS 5,478,827 A  12/1995  Oku et al. .................. 514/243
5,776,954 A  * 7/1998  De Laszlo et al. .......... 514/340

FOREIGN PATENT DOCUMENTS

| WO | 9705877 | 2/1997 |
| WO | 9705878 | 2/1997 |
| WO | 9716426 | 5/1997 |
| WO | 9716441 | 5/1997 |
| WO | 9716442 | 5/1997 |

* cited by examiner

Primary Examiner—C. S. Aulakh
(74) Attorney, Agent, or Firm—Peter C. Richardson; Paul H. Ginsburg; Seth H. Jacobs

(57) ABSTRACT

The present invention provides a compound of the formula:

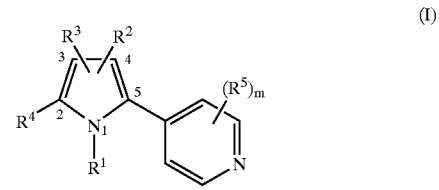

and its pharmaceutically acceptable salts, wherein $R^1$, $R^2$, $R^3$, $R^4$, $R^5$ and m are as defined in claim 1. The present invention also provides processes for the preparation thereof, the use thereof in treating cytokines mediated diseases and/or cell adhesion molecules (CAMs) mediated diseases and pharmaceutical compositions for use in such therapy.

18 Claims, No Drawings

PYRIDYLPYRROLE COMPOUNDS USEFUL AS INTERLEUKIN-AND TNF ANTAGONISTS

This application is a 371 of PCT/IB97/00703 filed May 15, 1997, now WO 98/02430 Jan. 22, 1998.

TECHNICAL FIELD

This invention relates to novel pyridylpyrrole compounds, processes for the preparation thereof, the use thereof in treating cytokines mediated diseases and/or cell adhesion molecules mediated diseases, and pharmaceutical compositions for use in such therapy.

BACKGROUND ART

Cytokines possess a multitude of regulatory and inflammatory effects. Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation.

There are many disease states in which excessive or unregulated IL-1 production is implicated in exacerbating and/or causing the disease. These include rheumatoid arthritis (RA), osteoarthritis (OA), endotoxemia and/or toxic shock syndrome, other acute and chronic inflammatory disease states such as the inflammatory reaction induced by endotoxin or inflammatory bowel disease (IBD), tuberculosis, atherosclerosis, muscle degeneration, cachexia, psoriatic arthritis, Reiter's syndrome, gout, traumatic arthritis, rubella arthritis and acute synovitis. Recent evidence also links IL-1 activity to diabetes.

Excessive or unregulated TNF production has been implicated in mediating or exacerbating a number of diseases including RA, rheumatoid spondylitis, OA, gouty arthritis and other arthritic conditions; sepsis, septic shock, endotoxin shock, gram negative sepsis, toxic shock syndrome, adult respiratory distress syndrome (ARDS), cerebral malaria, chronic pulmonary inflammatory disease, silicosis, pulmonary sarcoisosis, bone resorption diseases, reperfision injury, graft vs. host reaction, allograft rejections, fever and myalgias due to infection such as influenza, cachexia secondary to infection or malignancy, cachexia, secondary to acquired immune deficiency syndrome (AIDS), ARC (AIDS related complex), keloid formation, scar tissue formation, Crohn's disease, ulcerative colitis or pyresis. The concept of anti-TNF therapy has been validated by the demonstration that soluble TNF receptor and neutralizing monoclonal antibodies (MAbs) against TNF showed therapeutic efficacy in a variety of preclinical and clinical studies (e.g., Elliott, M. J. et al., *The Lancet*, 1994, 344, 1125. Dullemen, H. M. V. et al., *Gastroenterology*, 1995, 109, 129.)

Interleukin-8 (IL-8) is a chemotactic factor first identified and characterized in 1987. IL-8 is produced by several cell types including neutrophils, mononuclear cells, fibroblasts, endothelial cells, epithelial cells and keratinocytes. Elevated IL-8 levels have been reported in joint fluids in RA, gouty arthritis, psoriatic scale and ARDS. Its production from endothelial cells is induced by IL-1, TNF or lipopolysaccharide (LPS). IL-8 has been shown to have chemoattractant properties for neutrophils, T-lymphocytes and basophils. In addition, it promote angiogenesis as well as neutrophil activation, including lysozomal enzyme release and respiratory burst. IL-8 has also been shown to increase the surface expression of Mac-1 (CD 11b/CD18) on neutrophils, this may contribute to increased adhesion of the neutrophils to vascular endothelial cells. Many diseases are characterized by massive neutrophil infiltration. Conditions associated with an increased IL-8 production would benefit by compounds which are suppressive of IL-8 production.

IL-1 and TNF affect a wide variety of cells and tissues, and these cytokines as well as other leukocyte derived cytokines are important and critical inflammatory mediators of a wide variety of disease states and conditions. The inhibition of these cytokines is of benefit in controlling, reducing and alleviating many of these disease states.

Cellular movement and adhesion are a fundamental biological response to external stimuli. During an inflammatory response, leukocytes must leave the plasma compartment and migrate to the point of antigenic insult. The mechanism of this migratory event is a complex interplay between soluble mediators and membrane-bound cellular adhesion molecules. Soluble cellular chemotactic factors, which are produced in the damaged tissue by a variety of resident cells, set up a chemical concentration gradient out to the plasma compartment. Interaction of these factors with their receptors on leukocytes leads to a directional migration of the leukocytes toward increasing concentrations of the chemotactic factor. Simultaneously, various adhesion molecules are upregulated on the leukocyte which mediate the initial rolling on the endothelial tissue, binding to a specific ligand on the activated endothelial tissue, and finally migration between endothelial cells into the tissue. The steps in this cascade of events are mediated by the interaction of specific cell surface protein, termed "cell adhesion molecules (CAMs)". E-selectin (ELAM-1, endothelial leukocyte adhesion molecule-1), ICAM-1 (intercellular adhesion molecule-1), and VCAM-1 (vascular cell adhesion molecule-1) are three major adhesion molecules whose expression on endothelial cells is upregulated upon treatment with inflammatory stimuli. ICAM-1 is expressed at low levels on resting endothelium and is markedly induced in response to cytokines such as IL-1, TNF and interferon-γ (IFN-γ). VCAM-1 is not expressed in resting endothelium but is induced by IL-1, TNF and IL-4. Induction of both ICAM-1 and VCAM-1 occurs 4 to 6 hours after cytokine treatment and cell surface expression remains elevated for up to 72 hours after treatment with cytokines. On the other hand, induction of transcription of the E-selectin gene by cytokines such as IL-1 and TNF results in an increase in the expression on the surface of endothelial cells peaking approximately 4–6 hours after challenge, and returns toward a basal level of expression by 24 hours.

The concept of anti-CAMs therapy has been validated by the demonstration that MAbs against ICAM-1 and antisense oligonucleotide against ICAM-1 showed therapeutic efficacy in a variety of preclinical and clinical studies (A. F. Kavanaugh et al., *Arthritis Rhetun*, 1994, 37, 992; C. E. Haug et al., *Transplantation*, 1993, 55, 766; and J. E. Jr. Sligh et al., *Proc. Natl. Acad. Sci.*, 1993, 90, 8529). Further support comes from the reports of the in vivo activity of sLeX and related carbohydrates, antagonists of E-selectin mediated adhesion (M. S. Mulligan et al., *Nature*, 1993, 364, 149–151). Thus, the potential therapeutic targets for CAMs inhibitors range from, but are not limited to, RA, IBD and psoriasis to ischemia/reperfusion injury, autoimmune diabetes, organ transplantation, ARDS, tumor metastases and AIDS, as is evident from the many ongoing development activities. The regulation of the functions of CAMs is of benefit in controlling, reduction and alleviating many of these disease states. There remains a need for treatment, in this field, for compounds which are capable of inhibiting cytokines production and/or CAMs expression. The pyridylpyrroles of the present invention have been shown in an in vitro assay to inhibit cytokines production and/or CAMs expression.

International Publication No. WO 95/18122 discloses 2-heteroaryl-3-cyanopyrrole compounds having agrochemical activities.

British Patent No. GB1311336 discloses quaternary salts of pyrrolylpyridine compounds (e.g., 4,4'-(3,4-dimethylpyrrol-2,5-diyl)bis(1-n-heptylpyridinium bromide) having antibacterial and fungal properties.

BRIEF DESCRIPTION OF THE INVENTION

The present invention provides a compound of the formula:

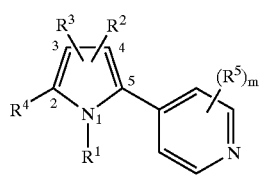

(I)

and its pharmaceutically acceptable salts, wherein
$R^1$ is selected from the following:
(a) hydrogen, $R^6$—, $R^6$—NH—, hydroxy-$R^6$— or $R^6$—O—$R^6$—;
(b) $R^6$—CO—, $R^6$—O—CO—$R^6$—, carboxy-$R^6$—, $NH_2$—CO— or $R^6$—NH—CO—; and
(c) Ar—, Ar—$R^6$—, Ar—NH—or Ar—CO—;
wherein Ar is selected from phenyl, naphthyl, pyridyl, quinolyl, thienyl, furyl, pyrrolyl, indolyl, benzothienyl and benzofuryl, the aryl or heteroaryl groups being optionally substituted with one or two substituents selected from $C_{1-4}$ alkyl, $C_{1-4}$ alkoxy, halo-substituted $C_{1-4}$ alkyl, halo-substituted $C_{1-4}$ alkoxy, nitro, hydroxy, amino, $R^6$—NH—, $(R^6)_2N$—, halo, formyl, halo-substituted phenoxy, halo-substituted phenyl, $C_{1-4}$ alkyl-substituted phenoxy, halo-substituted phenylthio, $C_{1-4}$ alkoxycarbonyl, $C_{1-4}$ alkylthio and $C_{1-4}$ alkyl-SO—; and
wherein $R^6$ is $C_{1-6}$alkyl optionally substituted by up to four halogen atoms;
$R^2$ and $R^4$ are independently selected from the following:
(d) hydrogen, halo, $R^6$—, $C_{2-6}$ alkenyl, $C_{2-6}$ alkynyl, hydroxy-$R^6$—, $R^6$—O—$R^6$—, mercapto-$R^6$—, $R^6$—S—$R^6$—, —$NH_2$, $R^6$—NH—, $(R^6)_2$—N—, $R^6$—O—, $R^6$—S—, $R^6$—SO— and $R^6$—$SO_2$—;
(e) 1,4-dioxa-8-azaspiro[4,5]-decanyl,

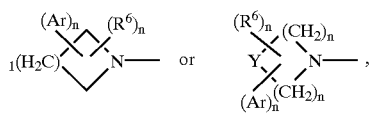

wherein Y is selected from —NH, —N—$R^6$, —N—Ar, O and S; l is 0, 1, 2, 3, 4 or 5; n is independently 0, 1 or 2; and Ar is as defined above;
(f) Ar—, Ar—$R^6$—, Ar—$C_{2-6}$ alkenyl, Ar—$C_{2-6}$ alkynyl, Ar—O—, Ar—O—$R^6$—, Ar—$R^6$—O—, Ar—S—, Ar—$R^6$—S—, Ar—NH—, $(Ar)_2$—$R^6$—, Ar—$R^6$—NH— or $(Ar)_2$—N—;
(g) $R^6$—CO—, —$NO_2$, $NH_2$—CO—, $R^6$—NH—CO—, $(R^6)_2$—N—CO—, Ar—CO—, $(Ar—R^6)_2$-N—CO—, Ar—$R^6$—CO—, Ar—NH—CO— or Ar—$R^6$—NH—CO—; and
(h) $R^6$—CO—NH—, Ar—CO—NH—, Ar—$R^6$—CO—NH—or $H_2N$—CO—NH—;
wherein Ar and $R^6$ are as defined above, provided that $R^2$ is not Ar;
$R^3$ is selected from the following:
(i) $C_{2-6}$ alkenyl, $C_{2-6}$ alkynyl, halo, hydroxy-$R^6$—, $R^6$—O—$R^6$—, $R^6$—S—$R^6$—, Ar—, $NH_2$—$R^6$— or $R^6$—NH—$R^6$;
(j) formyl, carboxy, carboxy-$R^6$—, tetrazolyl, triazolyl, imidazolyl, oxazolyl, thiazolyl, $R^6$—CO—, $C_{2-6}$ alkenyl—CO—, $C_{2-6}$ alkynyl—CO—, $R^6$—CO—$R^6$—, $C_{2-6}$ alkenyl—CO—$R^6$—, $C_{2-6}$alkynyl—CO—$R^6$—, $R^6$—O—CO—, $R^6$—O—CO—$R^6$—, $R^6$—S—CO—, $C_{2-6}$ alkenyl—O—CO—, $C_{2-6}$ alkynyl—O—CO— or $R^6$—O—$R^6$—CO—;
(k) $R^6$—CO—NH—, Ar—CO—NH—, Ar—$R^6$—CO—NH—, —$NH_2$, $R^6$—NH—, $(R^6)_2$—N—, $H_2N$—CO—NH—, $R^6$—NH—CO—NH—, $(R^6)_2$—N—CO—NH—, Ar—NH—CO—NH—, $(Ar)_2$—N—CO—NH—, HO—N=CH—$R^6$—, $R^6$O—N=CH— or $R^6$O—N=CH—$R^6$—;
(l) $R^6$—SO—, $R^6$—NH—$SO_2$— $R^6$—$SO_2$—, —$SO_2NH_2$, —$SONH_2$, $R^6$—NH—SO—, Ar—SO—, Ar—$R^6$SO—, Ar—$SO_2$—, $C_{2-6}$ alkenyl-$SO_2$—, $C_{2-6}$ alkynyl-$SO_2$—, Ar—$R^6$—$SO_2$—, Ar—NH—$SO_2$—, Ar—$R^6$—NH—$SO_2$—, Ar—NH—SO— or Ar—$R^6$—NH—SO—; and
(m) Ar—CO—, Ar—$R^6$—CO—, Ar—$C_{2-6}$ alkenyl—CO—, Ar—$C_{2-6}$ alkynyl—CO—, Ar—O—CO—, Ar—O—$R^6$—CO—, Ar—S—$R^6$—CO—, Ar—$R^6$—O—CO—, Ar—$R^6$—S—CO—, $(Ar)_2$—$C_{2-6}$ alkenyl-CO—, $(Ar)_2$—$C_{2-6}$ alkynyl-CO—, $(Ar)_2$—$R^6$—O—CO— or $(Ar)_2$—$R^6$—S—CO—;
wherein Ar and $R^6$ are as defined above; or
two of $R^2$, $R^3$ and $R^4$ together form a group of the formula —$A^1$—$B^1$—$A^2$—$B^2$—$A^3$— which, together with the carbon atoms to which $A^1$ and $A^3$ are attached, defines a ring having 5 to 8 ring atoms, the ring optionally being substituted with one or two substituents selected from hydroxy, $R^6$, $C_{1-4}$ alkoxy and Ar, wherein $A^1$, $A^2$ and $A^3$ are independently direct bond or $C_{1-4}$ alkylene and $B^1$ and $B^2$ are independently direct bond, O, S, SO, CO, NH or $NR^6$;
$R^5$ is independently selected from the following:
(n) hydrogen, halo, $R^6$—, hydroxy-$R^6$— or $R^6$—O—$R^6$—;
(o) Ar—, Ar—$R^6$—, Ar—O—, Ar—S—, Ar—NH— or Ar—CO—; and
(p) $R^6$—CO—, $R^6$—O—CO— or $R^6$—NH—CO—; or
two of $R^5$ which are attached to adjacent carbon atoms on the pyridine ring complete a fused benzene ring, the benzene ring being optionally substituted with one or two substituents selected from $C_{1-4}$ alkyl, halo-substituted $C_{1-4}$ alkyl, halo-substituted $C_{1-4}$ alkoxy, nitro, hydroxy, amino and halo;
wherein $R^6$ and Ar are as defined above;
m is 0, 1, 2, 3 or 4; and
the nitrogen atom of the pyridyl ring attached to the 5-position of the pyrrole ring is optionally replaced by a N oxide group.

The present invention also provides a pharmaceutical composition for the treatment or alleviation of cytokine-mediated diseases or CAMs mediated diseases, which comprises a therapeutically effective amount of a compound of said formula (I) or its pharmaceutically acceptable carrier.

The present invention further provides a method for the treatment of disease conditions caused by cytokine-mediator or CAMs mediator, in a mammalian subject, which comprises administering to said subject a therapeutically effective amount of a compound of the formula (I).

The present invention also provides a pharmaceutical composition for the treatment or alleviation of cytokine-mediated diseases or CAMs mediated diseases, which comprises a therapeutically effective amount of a compound of the formula (I):
and its pharmaceutically acceptable salts, wherein
$R^1$ is selected from the following:
(a) hydrogen, $R^6$—, $R^6$—NH—, hydroxy-$R^6$— or $R^6$—O—$R^6$—;
(b) $R^6$—CO—, $R^6$—O—CO—$R^6$—, carboxy-$R^6$—, $NH_2$—CO— or $R^6$—NH—CO—; and
(c) Ar—, Ar—$R^6$—, Ar—NH— or Ar—CO—;
wherein Ar is selected from phenyl, naphthyl, pyridyl, quinolyl, thienyl, furyl, pyrrolyl, indolyl, benzothienyl and benzofuryl, the aryl or heteroaryl groups being optionally substituted with one or two substituents selected from $C_{1-4}$ alkyl, $C_{1-4}$ alkoxy, halo-substituted $C_{1-4}$ alkyl, halo-substituted $C_{1-4}$ alkoxy, nitro, hydroxy, amino, $R^6$—NH—, $(R^6)_2$N—, halo, formyl, halo-substituted phenoxy, halo-substituted phenyl, $C_{1-4}$ alkyl-substituted phenoxy, halo-substituted phenylthio, $C_{1-4}$ alkoxycarbonyl, $C_{1-4}$ alkylthio and $C_{1-4}$ alkyl-SO—; and
wherein $R^6$ is $C_{1-6}$ alkyl optionally substituted by up to four halogen atoms;
$R^2$ and $R^4$ are independently selected from the following:
(d) hydrogen, halo, $R^6$—, $C_{2-6}$ alkenyl, $C_{2-6}$ alkynyl, hydroxy-$R^6$—, $R^6$—O—$R^6$—, mercapto-6—, $R^6$—S—$R^6$—, —$NH_2$, $R^6$—NH—, $(R^6)_2$—N—, $R^6$—O—, $R^6$—S—, $R^6$—SO—and $R^6$—$SO_2$;
(e) 1,4-dioxa-8-azaspiro[4,5]-decanyl,

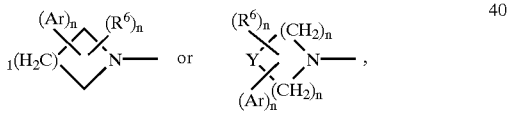

wherein Y is selected from —NH, —N—$R^6$, —N—Ar, O and S; l is 0, 1, 2, 3, 4 or 5; n is independently 0, 1 or 2; and Ar is as defined above;
(f) Ar—, Ar—$R^6$—, Ar—$C_{2-6}$ alkenyl, Ar—$C_{2-6}$ alkynyl, Ar—O—, Ar—O—$R^6$—, Ar—$R^6$—O—, Ar—S—, Ar—$R^6$—S—, Ar—NH—, $(Ar)_2$—$R^6$—, Ar—$R^6$—NH— or $(Ar)_2$—N—;
(g) $R^6$—CO—, —$NO_2$, $NH_2$—CO—, $R^6$—NH—CO—, $(R^6)_2$—N—CO—, Ar—CO—, (Ar—$R^6)_2$—N—CO—, Ar—$R^6$—CO—, Ar—NH—CO— or Ar—$R^6$—NH—CO—; and
(h) $R^6$—CO—NH—, Ar—CO—NH—, Ar—$R^6$—CO—NH—or $H_2$N—CO—NH—;
wherein Ar and $R^6$ are as defined above, provided that $R^2$ is not Ar;
$R^3$ is selected from the following:
(i) $C_{2-6}$ alkenyl, $C_{2-6}$ alkynyl, halo, hydroxy-$R^6$—, $R^6$—O—$R^6$—, $R^6$—S—$R^6$—, Ar—, $NH_2R^6$— or $R^6NH$—$R^6$;
(j) cyano, $H_2N$—CO—, formyl, carboxy, carboxy-$R^6$—, tetrazolyl, triazolyl, imidazolyl, oxazolyl, thiazolyl, $R^6$—CO—, $C_{2-6}$ alkenyl-CO—, $C_{2-6}$ alkynyl-CO—, $R^6$—CO—$R^6$—, $C_{2-6}$ alkenyl-CO—$R^6$—, $C_{2-6}$ alkynyl-CO—$R^6$—, $R^6$—O—CO—, $R^6$—CO—$R^6$—, $R^6$—S—CO—, $C_{2-6}$ alkenyl—O—CO—, $C_{2-6}$ alkynyl—O—CO— or $R^6$—O—$R^6$—CO—;
(k) $R^6$—CO—NH—, Ar—CO—NH—, Ar—$R^6$—CO—NH—, —$NH_2$, $R^6$—NH—, $(R^6)_2$—N—, $H_2N$—CO—NH—, $R^6$—NH—CO—NH—, $(R^6)$—N—CO—NH—, Ar—NH—CO—NH—, $(Ar)_2$—N—CO—NH—, HO—N=CH—$R^6$—, $R^6O$—N=CH— or $R^6O$—N=CH—$R^6$—;
(l) $R^6$—SO—, $R^6$—NH—$SO_2$—$R^6$—$SO_2$—, —$SO_2NH_2$, —$SONH_2$, $R^6$—NH—SO—, Ar—SO—, Ar—$R^6$—SO—, Ar—$SO_2$—, $C_{2-6}$ alkenyl-$SO_2$—, $C_{2-6}$ alkynyl-$SO_2$—, Ar—$R^6$—$SO_2$—, Ar—NH—$SO_2$—, NH—$SO_2$—, Ar—NH—SO— or Ar—$R^6$—NH—SO—; and
(m) Ar—CO—, Ar—$R^6$—CO—, Ar—$C_{2-6}$ alkenyl-CO—, Ar—$C_{2-6}$ alkynyl-CO—, Ar—O—CO—, Ar—O—$R^6$—CO—, Ar—S—$R^6$—CO—, Ar—$R^6$—O—CO—, Ar—$R^6$—S—CO—, $(Ar)_2$—$C_{2-6}$ alkenyl-CO—, $(Ar)_2$—$C_{2-6}$ alkynyl-CO—, $(Ar)_2$—$R^6$—O—CO— or $(Ar)_2$—$R^6$—S—CO—;
wherein Ar and $R^6$ are as defined above; or
two of $R^2$, $R^3$ and $R^4$ together form a group of the formula —$A^1$—$B^1$—$A^2$—$B^2$—$A^3$— which, together with the carbon atoms to which $A^1$ and $A^3$ are attached, defines a ring having 5 to 8 ring atoms, the ring optionally being substituted with one or two substituents such as hydroxy, $R^6$, $C_{1-4}$ alkoxy or Ar, wherein $A^1$, $A^2$ and $A^3$ are independently direct bond or $C_{1-4}$ alkylene and $B^1$ and $B^2$ are independently direct bond, O, S, SO, CO, NH or $NR^6$;
$R^5$ is independently selected from the following:
(n) hydrogen, halo, $R^6$—, hydroxy-$R^6$— or $R^6$—O—$R^6$—;
(o) Ar—, Ar—$R^6$—, Ar—O—, Ar—S—, Ar—NH— or Ar—CO—; and
(p) $R^6$—CO—, $R^6$—O—CO— or $R^6$—NH—CO—; or
two of $R^5$ which are attached to adjacent carbon atoms on the pyridine ring complete a fused benzene ring, the benzene ring being optionally substituted with one or two substituents selected from $C_{1-4}$ alkyl, halo-substituted $C_{1-4}$ alkyl, halo-substituted $C_{1-4}$ alkoxy, nitro, hydroxy, amino and halo;
wherein $R^6$ and Ar are as defined above;
m is 0, 1, 2, 3 or 4; and
the nitrogen atom of the pyridyl ring attached to the 5-position of the pyrrole ring is optionally replaced by a N oxide group.

DETAILED DESCRIPTION OF THE INVENTION

As used herein, the term "$C_{1-6}$ alkyl" means straight or branched chain saturated radicals of 1 to 6 carbon atoms, including, but not limited to methyl, ethyl, n-propyl, isopropyl, n-butyl, isobutyl, secondary-butyl, tertiary-butyl, and the like.

As used herein, the term "$C_{2-6}$ alkenyl" means straight or branched chain unsaturated radicals of 2 to 6 carbon atoms, including, but not limited to ethenyl, 1-propenyl, 2-propenyl (allyl), isopropenyl, 2-methyl-1-propenyl, 1-butenyl, 2-butenyl, and the like.

As used herein, the term "halo" means fluoro, chloro, bromo and iodo.

As used herein, the term "N oxide group" means one represented by the following formula:

As used herein, the term "equivalent of $R^{2a}$—C(O)—CH$_2$—R$^7$" means compounds with similar reactivity to $R^{2a}$—C(O)—CH$_2$—R$^7$, or compounds which can be transformed to $R^{2a}$—C(O)—CH$_2$—R$^7$ in situ, such as enamine equivalent $R^{2a}$—C(NH$_2$)=CH—R$^7$, or enolether equivalent $R^{2a}$—C(OR$^{3a}$)=CH—R$^7$.

In the formula (I), a substituent of substituted R$^6$ (for example, hydroxy-R$^6$—, carboxy-R$^6$—, R$^6$—O—R$^6$—, etc.) may be attached to any carbon atom of the R$^6$.

In the group "(Ar)$_2$—R$^6$—", two of Ar may be the same or different from each other, and may be attached to a same carbon atom or different carbon atoms of R$^6$.

A preferred group of compounds of this invention includes the compound of the formula (I) wherein R$^1$ is selected from group (a); R$^2$ is selected from group (d), (e) or (f), provided that R$^2$ is not Ar; R$^3$ is selected from groups (i), (j), (k) and (m), provided that R$^3$ is not Ar, tetrazolyl, triazolyl, imidazolyl, oxazolyl nor thiazolyl; R$^4$ is selected from group (d), (e) or (f); and R$^5$ is selected from group (n); and m is 0, 1 or 2.

A more preferred group of compounds of this invention includes the compounds of formula (I) wherein R$^1$ is hydrogen, C$_{1-4}$ alkyl, C$_{1-4}$ alkylamino, halo substituted C$_{1-4}$ alkyl, hydroxy-C$_{1-4}$ alkyl, C$_{1-4}$ alkoxyalkyl or halo C$_{1-4}$ alkoxy-C$_{1-4}$ alkyl; R$^2$ is hydrogen, halo, R$^6$—, hydroxy-R$^6$— or R$^6$—O—R$^6$—; R$^3$ is C$_{2-6}$ alkenyl, C$_{2-6}$ alkynyl, halo, hydroxy-R$^6$—, R$^6$—O—R$^6$—, R$^6$—S—R$^6$—, R$^6$—NH—R$^6$—, formyl, carboxy, carboxy-R$^6$—, R$^6$—CO—, C$_{2-6}$ alkenyl-CO—, C$_{24}$ alkynyl-CO—, R$^6$—CO—R$^6$—, C$_{2-6}$ alkenyl-CO—R$^6$—, C$_{2-6}$ alkynyl-CO—R$^6$—, R$^6$—O—CO—, R$^6$—O—CO—R$^6$—, R$^6$—S—CO—, C$_{2-4}$ alkenyl—O—CO— or R$^6$—O—R$^6$—CO—; R$^4$ is hydrogen, R$^6$—, morpholino optionally substituted by one, two or three C$_{1-4}$ alkyl or phenyl, 1-piperidinyl optionally substituted by one, two or three C$_{1-4}$ alkyl or phenyl, 4-piperazinyl optionally substituted at its 1-position by C$_{1-4}$ alkyl or phenyl, pyridyl, quinolyl, furyl, thienyl or pyrrolyl, phenyl, naphthyl, pyridyl, quinolyl, thienyl, furyl, pyrrolyl, indolyl, benzothienyl or benzofuryl, and wherein said phenyl, naphthyl, pyridyl, quinolyl, thienyl, furyl, pyrrolyl, indolyl, benzothienyl or benzofuryl may optionally be substituted with one or two substituents independently selected from C$_{1-4}$ alkyl, C$_{1-4}$ alkoxy, hydroxy, halo, formyl, C$_{1-4}$ halo-substituted alkyl, halo-substituted phenoxy, halo-substituted phenylthio, C$_{1-4}$ alkoxycarbonyl, C$_{1-4}$ alkylthio and C$_{1-4}$ alkyl-SO—; Rs is hydrogen, halo, C$_{1-4}$ alkyl or halo substituted C$_{1-4}$ alkyl; and m is 0 or 1.

A more preferred group of compounds of this invention includes the compounds of formula (I) wherein R$^1$ is hydrogen, C$_{1-4}$ alkyl or C$_{1-4}$ alkoxy-C$_{1-4}$ alkyl; R$^2$ is hydrogen, halo, C$_{1-4}$ alkyl optionally substituted by halo, hydroxy-C$_{1-4}$ alkyl or C$_{1-4}$-alkoxy-C$_{1-4}$ alkyl; R$^3$ is C$_{2-4}$ alkenyl, C$_{2-4}$ alkynyl, halo, hydroxy-C$_{1-4}$ alkyl, C$_{1-4}$ alkoxy-C$_{1-4}$ alkyl, formyl, carboxy, C$_{1-4}$ alkylcarbonyl, C$_{1-4}$ alkylcarbonyl-C$_{1-4}$ alkyl, C$_{1-4}$ alkoxy-carbonyl, C$_{1-4}$ alkoxycarbonyl-C$_{1-4}$ alkyl, C$_{2-4}$ alkenyloxycarbonyl or C$_{1-4}$ alkyloxy-C$_{1-4}$-alkylcarbonyl; R$^2$ and R$^3$ are at the 4 and 3 positions of the pyrrole ring, respectively; R$^4$ is C$_{1-4}$ alkyl, morpholino, dimethylmorpholino, 1-piperidinyl, 4-piperazinyl optionally substituted at its 1-position by C$_{1-4}$ alkyl, phenyl or pyridyl, phenyl, naphthyl, pyridyl, quinolyl, thienyl, furyl or pyrrolyl, and wherein said phenyl, naphthyl, pyridyl, quinolyl, thienyl, furyl or pyrrolyl may optionally be substituted with one or two substituents independently selected from C$_{1-4}$ alkyl, hydroxy, C$_{1-4}$ alkoxy, halo, formyl, fluorophenoxy, methoxycarbonyl, ethoxycarbonyl, methylthio, ethylthio and methyl-SO—; and R$^5$ is hydrogen or halo.

A more preferred group of compounds of this invention includes the compounds of formula (I) wherein R$^1$ is hydrogen, C$_{1-4}$ alkyl or C$_{1-4}$ alkoxy-C$_{1-4}$ alkyl; R$^2$ is C$_{1-4}$ alkyl optionally substituted by halo, hydroxy-C$_{1-4}$ alkyl or C$_{1-4}$-alkoxy-C$_{1-4}$ alkyl; R$^3$ is C$_{2-4}$ alkenyl, hydroxy-C$_{1-4}$ alkyl, C$_{1-4}$ alkoxy-C$_{1-4}$ alkyl, formyl, C$_{1-4}$ alkylcarbonyl, C$_{1-4}$ alkylcarbonyl-C$_{1-4}$ alkyl, C$_{1-4}$ alkoxy-carbonyl, C$_{1-4}$ alkoxycarbonyl-C$_{1-4}$ alkyl; R$^4$ is morpholino, 1-piperidinyl, 4-phenyl-piperazin-1-yl, 1-(2-pyridyl)-piperazin4-yl, pyridyl, phenyl, naphthyl, pyrrolyl, furyl or thienyl, and wherein said pyridyl, phenyl, naphthyl, pyrrolyl, furyl or thienyl may optionally be substituted with C$_{1-4}$ alkoxy, halo, formyl, 4-fluorophenoxy, methoxycarbonyl, ethoxycarbonyl or methylthio; and R$^5$ is hydrogen.

A preferred group of compounds of this invention includes the compound of the formula (I) wherein R$^3$ at the 3-position and R$^4$ at the 2-position together form a group of the formula —A$^1$—B$^1$—A$^2$—B$^2$—A$^3$— which, together with the carbon atoms to which A$^1$ and A$^3$ are attached, defines a ring having 5 to 8 ring atoms, the ring optionally being substituted with one or more substituents selected from hydroxy, R$^6$, C$_{1-4}$ alkoxy and Ar, wherein A$_1$, A$^2$ and A$^3$ are independently direct bond or C$_{1-4}$ alkylene and B$^1$ and B$^2$ are independently direct bond, O, S, SO, CO, NH or NR$^6$.

Among these, a more preferred group of compounds of this invention includes the compound of the formula (I) wherein —A$^1$—B$^1$—A$^2$—B$^2$—A$^3$— is selected form —CO—(CH$_2$)$_3$—, —CO—(CH$_2$)$_2$—, —CO—CH$_2$—C(CH$_3$)$_2$—CH$_2$—, —CO—(CH$_2$)$_2$—C(CH$_3$)$_2$, —CO—(CH$_2$)$_4$—, —CO—CH$_2$—CH(CH$_3$)—CH$_2$—, —CO—O—CH(CH$_3$)—CH$_2$— and —CO—CH$_2$—S—CH$_2$—.

Also, a particularly preferred compound of the invention includes the compound of formula (I) wherein R$^1$ is hydrogen, methyl or methoxyethyl; R$^2$ is methyl, ethyl, monofluoromethyl, difluoromethyl, trifluoromethyl, phenyl, n-propyl, isopropyl, n-bytyl, isobutyl, methoxymethyl, nitrophenyl, hydroxymethyl or pyridyl; R$^3$ is acetyl, propanoyl, pentanoyl, ethoxycarbonyl, methoxycarbonyl, formyl, methanesulfonyl, hydroxyethyl, hydroxymethyl, benzyloxycarbonyl, allyloxycarbonyl, carboxyl, methylethoxycarbonyl, 1,1-dimethylethoxycarbonyl, propoxycarbonyl, butoxycarbonyl or methoxyethoxycarbonyl; R$^2$ and R$^3$ are at the 4 and 3 positions of the pyrrole ring, respectively; R$^4$ is methyl, phenyl, 2-fluorophenyl, 3-fluorophenyl, 4-fluorophenyl, naphthyl, pyridyl, quinolyl, thienyl, phenyl, hydrogen, morpholino, 1-piperidinyl, (1-phenyl)-4-piperazinyl or (2-pyridyl)-4-piperazinyl; and R$^5$ is hydrogen.

Among the compounds of the formula (I), the most preferred compound is one of the following:
3-acetyl-4-methyl-2,5-di(4-pyridyl)-1H-pyrrole;
3-acetyl-4-ethyl-2,5-di(4-pyridyl)-1H-pyrrole;
3-acetyl-2,5-di(4-pyridyl)4-trifluoromethyl-1H-pyrrole;

3-methoxycarbonyl-4-methyl-2,5-di(4-pyridyl)-1H-pyrrole;

3-acetyl-2,4-dimethyl-5-(4-pyridyl)-1H-pyrrole;

3-acetyl-4-methyl-2-phenyl-5-(4-pyridyl)-1lH-pyrrole;

3-methyl4-oxo-2-(4-pyridyl)-4,5,6,7-tetrahydro-1H-indole;

3-acetyl-2-(4-fluorophenyl)-4-methyl-5-(4-pyridyl)-1H-pyrrole;

3-acetyl-2-(2-fluorophenyl)-4-methyl-5-(4-pyridyl)-1H-pyrrole;

4-Oxo-2-(4-pyridyl)-3,6,6-trimethyl-4,5,6,7-tetrahydro-1H-indole;

3,6-Dimethyl4-oxo-2-(4-pyridyl)-4,5,6,7-tetrahydro-1H-indole;

4-Oxo-2-(4-pyridyl)-3,7,7-trimethyl-4,5,6,7-tetrahydro-1H-indole;

3-Acetyl-2-{(4-methoxycarbonyl)phenyl}-4-methyl-5-(4-pyridyl)-1H-pyrrole;

3-Acetyl-4-methyl-2-(1-piperidinyl)-5-(4-pyridyl)-1H-pyrrole;

3-Acetyl-4-methyl-2-(4-phenylpiperazin-1-yl)-5-(4-pyridyl)-1H-pyrrole;

3-Acetyl-2-(3-chloro-4-fluorophenyl)-4-methyl-5-(4-pyridyl)-1H-pyrrole;

3-Acetyl-2-(4-chlorophenyl)-4-methyl-5-(4-pyridyl)-1H-pyrrole;

3-Acetyl-2-(4-methoxyphenyl)-4-methyl-5-(4-pyridyl)-1H-pyrrole; and

3-Acetyl-4-methyl-2-(4-morpholino)-5-(4-pyridyl)-1H-pyrrole.

The present invention also provides a process for preparing a compound of the formula;

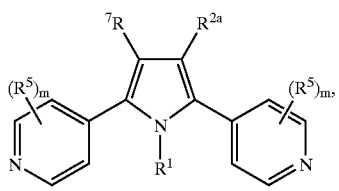

wherein $R^1$, $R^5$ and m are defined in claim 1; $R^{2a}$ are independently hydrogen, $C_{1-4}$ alkyl, $C_{2-4}$ alkenyl, $C_{2-4}$ alkynyl, Ar or Ar—$C_1$. alkyl; and $R^7$ is —C(O)$R^{3a}$, —C(O)O$R^{3a}$, —CN or —SO$_2$R$^{3a}$, wherein $R^{3a}$ is hydrogen, $C_{1-6}$ alkyl, $C_{2-6}$ alkenyl, $C_{2-6}$ alkynyl, Ar or Ar—$C_{1-4}$ alkyl, which comprises reacting a compound of the formula:

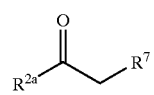

or its equivalent of this compound, with a compound of the formula:

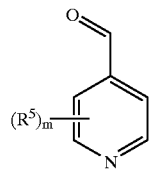

and amine $R^1NH_2$ in a reaction-inert solvent.

The compounds of the formula (I) of the present invention can be used as an active ingredient for the treatment or alleviation of asthma, arthritis, inflammatory bowel disease, sepsis, septic shock, rhinitis, inflammation of organs, AIDS, various inflammatory diseases, cardiovascular diseases, psoriasis, thrombosis, crohn's disease, cachexia, viral infections, gout, graft vs host disease, transplant rejection and the like.

Preferred pharmaceutical composition of this invention are those of the formula (I), wherein $R^1$ is selected from group (a); $R^2$ is selected from group (d), (e) or (f), provided that $R^2$ is not Ar; $R^3$ is selected from groups (i), (j), (k) and (m), provided that $R^3$ is not Ar, tetrazolyl, triazolyl, imidazolyl, oxazolyl nor thiazolyl; $R^4$ is selected from group (d), (e) or (f); and $R^5$ is selected from group (n); and m is 0, 1 or 2.

More preferred pharmaceutical composition of this invention are those of the formula (I), wherein $R^1$ is hydrogen, $C_{1-4}$ alkyl, $C_{1-4}$ alkylamino, halo substituted $C_{1-4}$ alkyl, hydroxy-$C_{1-4}$ alkyl, $C_{1-4}$ alkoxyalkyl or halo $C_{1-4}$ alkoxy-$C_{1-4}$ alkyl; $R^2$ is hydrogen, halo, $R^6$—, hydroxy-$R^6$— or $R^6O$—$R^6$—; $R^3$ is $C_{2-6}$ alkenyl, $C_{2-4}$ alkynyl, halo, hydroxy-$R^6$—, $R^6O$—$R^6$—, $R^6$—S—$R^6$—, $R^6$—NH—$R^6$—, formyl, carboxy, carboxy-$R^6$—, $R^6$—CO—, $C_{2-6}$ alkenyl-CO—, $C_{2-6}$ alkynyl-CO—, $R^6$—CO—$R^6$—, $C_{2-4}$ alkenyl-CO—$R^6$—, $C_{2-6}$ alkynyl-CO—$R^6$—, $R^6O$—CO—, $R^6$—O—CO—$R^6$—, $R^6$—S—CO—, $C_{2-6}$ alkenyl—O—CO— or $R^6O$—$R^6$—CO—; $R^4$ is hydrogen, $R^6$—, morpholino optionally substituted by one, two or three $C_{1-4}$ alkyl or phenyl, 1-piperidinyl optionally substituted by one, two or three $C_{1-4}$ alkyl or phenyl, 4-piperazinyl optionally substituted at its 1-position by phenyl or $C_{1-4}$ alkyl, pyridyl, quinolyl, furyl, thienyl or pyrrolyl, phenyl, naphthyl, pyridyl, quinolyl, thienyl, furyl, pyrrolyl, indolyl, benzothienyl or benzofuryl, and wherein said phenyl, naphthyl, pyridyl, quinolyl, thienyl, furyl, pyrrolyl, indolyl, benzothienyl or benzofuryl may optionally be substituted with one or two substituents independently selected from $C_{1-4}$ alkyl, $C_{1-4}$ alkoxy, hydroxy, halo, formyl, $C_{1-4}$ halo-substituted alkyl, halo-substituted phenoxy, halo-substituted phenylthio, $C_{1-4}$ alkoxycarbonyl, $C_{1-4}$ alkylthio and $C_{1-4}$ alkyl-SO—; $R^5$ is hydrogen, halo, $C_{1-4}$ alkyl or halo substituted $C_{1-4}$ alkyl; and m is 0 or 1.

Furthermore preferred pharmaceutical composition of this invention are those of the formula (I), wherein $R^1$ is hydrogen, $C_{1-4}$ alkyl or $C_{1-4}$ alkoxy-$C_{1-4}$ alkyl; $R^2$ is hydrogen, halo, $C_{1-4}$ alkyl optionally substituted by halo, hydroxy-$C_{1-4}$ alkyl or $C_{1-4}$-alkoxy-$C_{1-4}$ alkyl; $R^3$ is $C_{2-4}$ alkenyl, $C_{2-4}$ alkynyl, halo, hydroxy-$C_{1-4}$ alkyl, $C_{1-4}$ alkoxy-$C_{1-4}$ alkyl, formyl, carboxy, $C_{1-4}$ alkylcarbonyl, $C_{1-4}$ alkylcarbonyl-$C_{1-4}$ alkyl, $C_{1-4}$ alkoxy-carbonyl, $C_{1-4}$ alkoxycarbonyl-$C_{1-4}$ alkyl, $C_{2-4}$ alkenyloxycarbonyl or $C_{1-4}$ alkyloxy-$C_{1-4}$-alkylcarbonyl; $R^2$ and $R^3$ are at the 4 and 3 positions of the pyrrole ring, respectively; $R^4$ is $C_{1-4}$ alkyl, morpholino, dimethylmorpholino, 1-piperidinyl, 4-piperazinyl optionally substituted at its 1-position by $C_{1-4}$ alkyl, phenyl or pyridyl, phenyl, naphthyl, pyridyl, quinolyl, thienyl, furyl or pyrrolyl, and wherein said phenyl, naphthyl, pyridyl, quinolyl, thienyl, furyl or pyrrolyl may optionally be substituted with one or two substituents independently selected from $C_{1-4}$ alkyl, hydroxy, $C_{1-4}$ alkoxy, halo, formyl, fluorophenoxy, methoxycarbonyl, ethoxycarbonyl, methylthio, ethylthio and methyl-SO—; and Rs is hydrogen or halo.

Much furthermore preferred pharmaceutical composition of this invention are those of the formula (I), wherein $R^1$ is hydrogen, $C_{1-4}$ alkyl or $C_{1-4}$ alkoxy-$C_{1-4}$ alkyl; $R^2$ is $C_{1-4}$ alkyl optionally substituted by halo, hydroxy-$C_{1-4}$ alkyl or $C_{1-4}$-alkoxy-$C_{1-4}$ alkyl; $R^3$ is $C_{2-4}$ alkenyl, hydroxy-$C_{1-4}$ alkyl, $C_{1-4}$ alkoxy-$C_{1-4}$ alkyl, formyl, $C_{1-4}$ alkylcarbonyl, $C_{1-4}$ alkylcarbonyl-$C_{1-4}$ alkyl, $C_{1-4}$ alkoxy-carbonyl, $C_{1-4}$ alkoxycarbonyl-$C_{1-4}$ alkyl; $R^4$ is morpholino, 1-piperidinyl, 4-phenyl-piperazin-1-yl, 1-(2-pyridyl)-piperazin-4-yl, pyridyl, phenyl, naphthyl, pyrrolyl, furyl or thienyl, and wherein said pyridyl, phenyl, naphthyl, pyrrolyl, furyl or thienyl may optionally be substituted with $C_{1-4}$ alkoxy, halo, formyl, 4-fluorophenoxy, methoxycarbonyl, ethoxycarbonyl or methylthio; and $R^5$ is hydrogen.

Another preferred pharmaceutical composition of this invention are those of the formula (I), wherein $R^3$ at the 3-position and $R^4$ at the 2-position together form a group of the formula —$A^1$—$B^1$—$A^2$—$B^2$—$A^3$— which, together with the carbon atoms to which $A^1$ and $A^3$ are attached, defines a ring having 5 to 8 ring atoms, the ring optionally being substituted with one or more substituents selected from hydroxy, $R^6$, $C_{1-4}$ alkoxy and Ar, wherein $A^1$, $A^2$ and $A^3$ are independently direct bond or $C_{1-4}$ alkylene and $B^1$ and $B^2$ are independently direct bond, O, S, SO, CO, NH or $NR^6$.

Among these, more preferred pharmaceutical composition of this invention are those of the formula (1), wherein —$A^1$—$B^1$—$A^2$—$B^2$—$A^3$— is selected form —CO—$(CH_2)_3$—, —CO—$(CH_2)_2$—, —CO—$CH_2$—$C(CH_3)_2$—$CH_2$—, —CO—$(CH_2)_2$—$C(CH_3)_2$—, —CO—$CH_2$—CH$(CH_3)$—$CH_2$—, —CO—O—$CH(CH_3)$—$CH_2$— and —CO—$CH_2$—S—$CH_2$—.

Also, particularly preferred pharmaceutical composition of this invention are those of the formula (I), wherein $R^1$ is hydrogen, methyl or methoxyethyl; $R^2$ is methyl, ethyl, monofluoromethyl, difluoromethyl, trifluoromethyl, phenyl, n-propyl, isopropyl, n-bytyl, isobutyl, methoxymethyl, nitrophenyl, hydroxymethyl or pyridyl; $R^3$ is acetyl, propanoyl, pentanoyl, ethoxycarbonyl, methoxycarbonyl, formyl, methanesulfonyl, hydroxyethyl, hydroxymethyl, benzyloxycarbonyl, allyloxycarbonyl, carboxyl, methylethoxycarbonyl, 1,1-dimethylethoxycarbonyl, propoxycarbonyl, butoxycarbonyl or methoxyethoxycarbonyl; $R^2$ and $R^3$ are at the 4 and 3 positions of the pyrrole ring, respectively; $R^4$ is methyl, phenyl, 2-fluorophenyl, 3-fluorophenyl, 4-fluorophenyl, naphthyl, pyridyl, quinolyl, thienyl, phenyl, hydrogen, morpholino, 1-piperidinyl, (1-phenyl)-4-piperazinyl or (2-pyridyl)-4-piperazinyl; and $R^5$ is hydrogen.

Preferred individual compounds of this pharmaceutical composition of this invention are:

3-acetyl-4-methyl-2,5-di(4-pyridyl)-1H-pyrrole;
3-acetyl-4-ethyl-2,5-di(4-pyridyl)-1H-pyrrole;
3-acetyl-2,5-di(4-pyridyl)-4-trifluoromethyl-1H-pyrrole;
3-methoxycarbonyl-4-methyl-2,5-di(4-pyridyl)-1H-pyrrole;
3-acetyl-2,4-dimethyl-5-(4-pyridyl)-1H-pyrrole;
3-acetyl-4-methyl-2-phenyl-5-(4-pyridyl)-1H-pyrrole;
3-methyl-4-oxo-2-(4-pyridyl)4,5,6,7-tetrahydro-1H-indole;

3-acetyl-2-(4-fluorophenyl)-4-methyl-5-(4-pyridyl)-1H-pyrrole;
3-acetyl-2-(2-fluorophenyl)-4-methyl-5-(4-pyridyl)-1H-pyrrole;
4-Oxo-2-(4-pyridyl)-3,6,6-trimethyl-4,5,6,7-tetrahydro-1H-indole;
3,6-Dimethyl-4-oxo-2-(4-pyridyl)-4,5,6,7-tetrahydro-1H-indole;
4-Oxo-2-(4-pyridyl)-3,7,7-trimethyl-4,5,6,7-tetrahydro-1H-indole;
3-Acetyl-2-{(4-methoxycarbonyl)phenyl}-4-methyl-5-(4-pyridyl)-1H-pyrrole;
3-Acetyl-4-methyl-2-(1-piperidinyl)-5-(4-pyridyl)-1H-pyrrole;
3-Acetyl-4-methyl-2-(4-phenylpiperazin-1-yl)-5-(4-pyridyl)-1H-pyrrole;
3-Acetyl-2-(3-chloro-4-fluorophenyl)-4-methyl-5-(4-pyridyl)-1H-pyrrole;
3-Acetyl-2-(4-chlorophenyl)-4-methyl-5-(4-pyridyl)-1H-pyrrole;
3-Acetyl-2-(4-methoxyphenyl)-4-methyl-5-(4-pyridyl)-1H-pyrrole; and
3-Acetyl-4-methyl-2-(4-morpholino)-5-(4-pyridyl)-1H-pyrrole.

GENERAL SYNTHESIS

The compounds of this invention can be prepared by a variety of synthetic routes. Representative procedures are outlined as follows.

1. Synthesis of Pyridylpyrroles by Palladium Catalyzed Cross Coupling

The compounds of formula (I) can be prepared by using the method of Stille or Suzuki (for example, Snieckus V. et al., *J. Org. Chem.*, 1995, 60, 292, Stille, J. K. *Angew. Chem. Int. Ed. Engl.*, 1986, 25, 508, Mitchell, M. B. et al., *Tetrahedron Lett.*, 1991, 32, 2273, Matteson, D. S., *Tetrahedron*, 1989, 45, 1859).

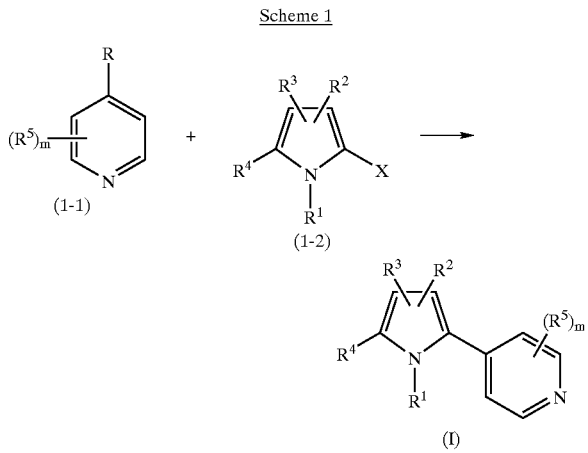

Scheme 1

(wherein R is an organometallic group such as trialkylstannyl, dialkylboronyl, boric acid or zinc halide such as zinc chloride, zinc bromide or zinc iodide; $R^1$, $R^2$, $R^3$, $R^4$ and $R^5$ are as already defined above; and X is halo such as Cl, Br or I)

As shown in Scheme 1, the pyrrole compounds (I) can be prepared by a reaction of compound (1-1) with pyrrolyl halide (1-2), in the presence of a catalyst, preferably tetrakis (triphenylphosphine)palladium or bis(triphenylphosphine) palladium(II) chloride, in the inert solvent such as benzene, toluene, xylene, tetrahydrofuran, dioxane, dimethylformamide, preferably dioxane under suitable conditions.

The reaction of trialkyl(4-pyridyl)stannane (1-1) with pyrrolyl halides (1-2) may be carried out in an inert solvent such as benzene, toluene, xylene, tetrahydrofuran, dioxane, dimethylformamide, preferably dioxane, typically in the presence of lithium chloride and a catalyst. The catalyst may be selected from those typically employed for the so-called Stille reaction (for example, tetrakis(triphenylphosphine) palladium or bis(triphenylphosphine)palladium(II) chloride). The reaction may be run at a temperature in a range from 20 to 160° C., preferably 60 to 130° C., for 10 minutes to 5 days, usually 30 minutes to 15 hours.

The reaction of dialkyl(4-pyridyl)borane (1-1) with pyrrolyl halides (1-2) may be carried out in an inert solvent such as benzene, toluene, tetrahydrofuran, preferably toluene, typically in the presence of a base such as potassium hydroxide, triethylamine, sodium ethoxide, sodium acetate or quaternary ammonium halide, preferably potassium hydroxide. The catalyst may be selected from those typically employed for the so-called Suzuki reaction (for example, tetrakis(triphenylphosphine)palladium or bis (triphenylphosphine)palladium(II) chloride). The reaction is run at a temperature in the range from 20 to 160° C., preferably 60 to 130° C. for 10 minutes to 5 days, usually 30 minutes to 15 hours.

The reaction of 4-pyridineboronic acid (1-1) with pyrrolyl halides (1-2) may be carried out in a solvent such as benzene, toluene, dimethoxyethane, dimethylformamide, preferably dimethoxyethane, typically in the presence of a base such as potassium hydroxide, triethylamine, sodium bicarbonate, preferably sodium bicarbonate, or a combination of water and above compounds, preferably water and dimethoxyethane. The catalyst may be selected from those typically employed for the so-called Suzuki reaction (for example, tetrakis(triphenylphosphine)palladium, bis (triphenylphosphine)palladium(II) chloride, or {bis (diphenylphosphino)butane}palladium(II) chloride). The reaction is run at a temperature in the range from 20 to 160° C., usually 60 to 130° C. for 10 minutes to 5 days, usually 30 minutes to 15 hours.

The procedures and conditions to carry out these coupling reactions are known to those in the art, and described in several technical literatures. For example, the procedures of Gronowitz, S. et al. and Snieckus, V. et al. for alkylstannanes are described in *J. Het. Chem.*, 1990, 27, 2165, and *J. Org. Chem.*, 1995, 60, 292; the procedure of Terashima, M. et al. for alkyl boranes, is in *Heterocycles*, 1984, 22, 265 and 2471, and in *Chem. Pharm. Bull.*, 1983, 31, 4573; and the procedures of Fischer, F. C., Mitchel, M. B. et al. and McKillop, A. et al. for boric acids are in *J. Red. Trav. Chim. Pays-Bays*, 1965, 84, 439, *Tetrahedron Lett.*, 1991, 32, 2273, and *Tetrahedron*, 1992, 48, 8117.

The 4-metalpyridines (1-1) (R=metal) can be prepared according to the procedure of the above literatures. The requisite pyrrolyl halides (1-2) can be prepared from the corresponding pyrroles by halogenation known in the art. The pyrroles for halogenation are either commercially available or can be prepared by using methods known in the art, for example, Hantzsch's method, Feist's method, Knorr's method and Katritzky's method (*Tetrahedron*, 1995, 51, 13271).

As apparent to one skilled in the art, the compound (I) can be also obtained from a reaction of the compound (1-1) wherein R is halo and the compound (1-2) wherein X is replaced by an organometallic group such as $Me_3Sn$, $Bu_3Sn-$, $Et_2B-$, $(HO)_2B-$ or zinc halide. The replacement of a halogen atom by the organometallic group can be carried out by the halogen-metal exchange, followed by a reaction of appropriate reagents such as trimethyltin chloride, tributyltin chloride, diethyl methoxyborane or trimethyl borate.

2. Synthetic Methods of 2,5-Diarylpyrroles

The compounds of the formula (Ia) can be prepared by the following novel method.

Scheme 2

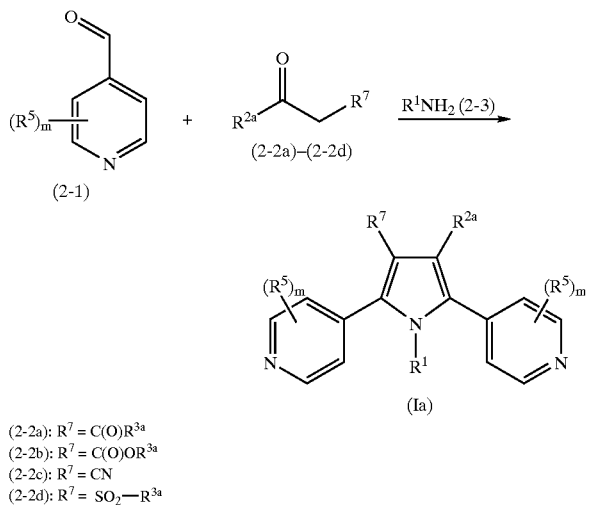

(2-2a): $R^7 = C(O)R^{3a}$
(2-2b): $R^7 = C(O)OR^{3a}$
(2-2c): $R^7 = CN$
(2-2d): $R^7 = SO_2-R^{3a}$ (wherein $R^1$, $R^5$ and m are as defined above; $R^{2a}$ and $R^{3a}$ are independently hydrogen, $C_{1-6}$ alkyl, $C_{2-6}$ alkenyl, $C_{2-6}$ alkynyl, Ar or Ar—$C_{1-4}$ alkyl; and $R^7$ is an electron withdrawing group exemplified by $C(O)R^{3a}$, $C(O)OR^{3a}$, CN or $SO_2R^{3a}$.)

As shown in Scheme 2, the compounds of the formula (Ia) can be prepared from a reaction of aldehyde (2-1), 1,3-dione (2-2a) and amine (2-3) in an inert reaction solvent. For example, 3-acetyl-4-methyl-2,5-di(4-pyridyl)-1H-pyrrole (Ia) ($R^1=R^5=H$, $R^{2a}$=methyl, $R^7=C(O)CH_3$) can be efficiently prepared from 4-pyridinecarboxaldehyde (2-1) ($R_5$=H) and 2,4-pentanedione (2-2a) ($R^{2a}=R^{3a}$=methyl) in the presence of ammonia (2-3) ($R^1$=H) in one step.

Scheme 2a

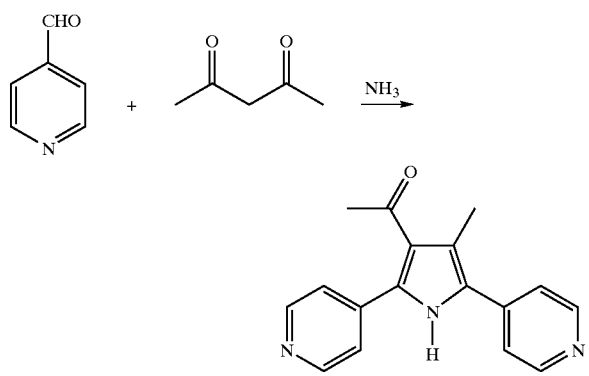

This reaction may be carried out in a reaction inert solvent, for example, ethanol, methanol, toluene, xylene, tetrahydrofuran, methylene chloride, preferably ethanol.

However, a solvent is not always necessary. The novel reactions of this pyrrole synthesis generally proceed at a temperature in the range from −20 to 250° C., preferably 0 to 150° C., more preferably 40 to 110° C. for 10 minutes to 3 days, usually 30 minutes to 15 hours.

The analogs of the compounds (Ia) with a variety of functional groups, such as alkylcarboxy, cyano or sulfonyl, instead of carbonyl, can be synthesized by the use of β-ketoesters (2-2b), β-ketonitriles (2-2c), β-ketosulfones (2-2d) or their equivalents of 1,3-diones instead of the 1,3-diones (2-2a) in the above reaction.

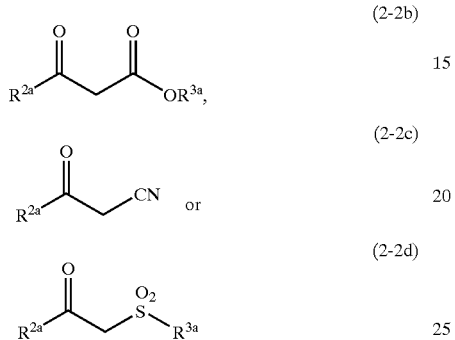

As the aldehydes (2-1), quinolinecarboxaldehydes (two of $R^5$ are attached to adjacent carbon atoms on the pyridine ring to complete a fused benzene ring) can be also used in this reaction, instead of 4-pyridinecarboxaldehyde, to afford 2,5-diquinolylpyrrole compounds. Also, 2,5-diarylpyrroles having different aryl rings at the 2 and 5-positions (Ia) can be prepared by the reaction of a mixture of two kinds of arylaldehydes (2-1) with the 1,3-dione (2-2a) or their equivalent ((2-2b)–(2-2d)) and the amine (2-3). For example, 2-pyridyl-5-quinolylpyrroles can be prepared by a reaction of a mixture of 4-pyridinecarboxaldehyde (2-1) and 4-quinolinecarboxaldehyde (2-1), 1,3-dione (2-2a) or their equivalent ((2-2b)–(2-2d)) and amine (2-3). As shown in Scheme 2b, 3-acetyl-4-methyl-2-(4-pyridyl)-5-(4-quinolyl)-1H-pyrrole can be efficiently prepared from 4-pyridinecarboxaldehyde, 4-quinolinecarboxaldehyde, 2,4-pentanedione and anmonia in one step.

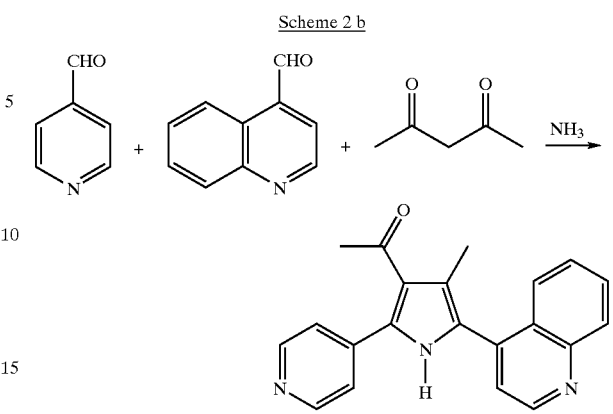

As amines (2-3), the other ammonia source such as ammonium acetate can be used in this reaction. By the use of substituted amines (2-3) ($R^1$=alkyl, aryl) such as alkylamines or arylamine in the above reaction can give the corresponding 1-substituted pyrroles.

In addition, the functional groups at the 1-, 3- or 4-position of the pyrroles prepared above can be converted to a variety of functional groups by the methods known to one skilled in the art.

3. Synthesis of Pyridylpyrroles by Cycloaddition Reaction

The compounds of formula (Ib) or (Ic) can be also prepared by [3+2] cycloaddition as described in Scheme 3.

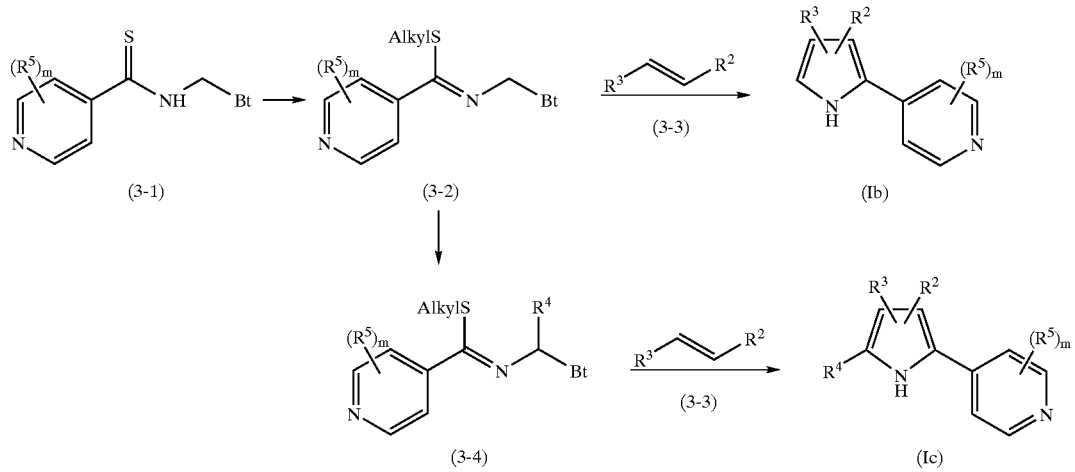

(wherein Bt is benztriazole)

In Scheme 3, the compounds of the formula (Ib or Ic) can be prepared by [3+2] cycloaddition of thioamidates ((3-2) or (3-4)) and α,β-unsaturated ketones (Michael acceptor) (3-3). This reaction can be carried out in an inert solvent, such as tetrahydrofuran or dimethylformamide, in the presence of base, preferably sodium hydride. This reaction can be carried out at a temperature in a range from −20 to 150° C., preferably 0 to 100° C., for 10 minutes to 3 days, usually 3 minutes to 15 hours. The reaction procedures and conditions are described in, for example, Katritzky A. R. et al., *Tetrahedron*, 1995, 51, 13271.

Thioamides (3-1) can be readily obtained by Mannich condensation of substituted isonicotinoylthioamide, aldehyde and benztriazole according to the literature procedure. Treatment of the thioamides (3-1) with one equivalent of base such as butyllithium or sodium hydride, followed by a reaction with alkyliodide gives thioimidates (3-2). This reaction may be carried out in a reaction inert solvent, for example, tetrahydrofuran, diethylether or methylene chloride, preferably tetrahydrofuran at a temperature in the range from −100 to 50° C., preferably −78 to 20° C. for 10 minutes to 2 days, usually 30 minutes to 3 hours.

In addition, the thioimidates (3-2) can also be alkylated at the α-position leading to the compound (3-4).

Alternatively, the compounds of formula (I) can be also prepared by a variety of methods known in the art, such as Knorr's method, Feist's method, and Hantzsch's method.

4. Synthesis of Pyridylpyrroles

The compounds of formula (I) can be also prepared from (4-1) by using the method of Stille or Suzuki or by nucleophilic substitution as described in Scheme 4.

Scheme 4. Synthesis of pyridylpyrroles

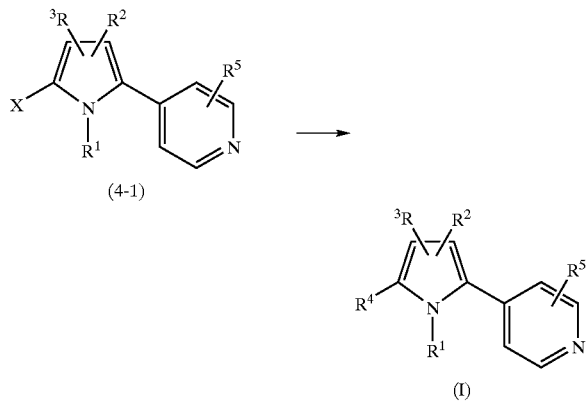

(wherein $R^1$, $R^2$, $R^3$, $R^4$, and $R^5$ are as already defined above; and X is halo such as Cl, Br, or I) The pyrrolyl halides (4-1) can be prepared from the corresponding pyrroles by halogenation known in the art.

The compounds of formula (I) can be prepared by a reaction of compound (4-1) with an appropriate organometallic reagent such as trialkylstannyl, dialkylboronyl, boric acid, in the presence of a catalyst, preferably tetrakis (triphenylphosphine)palladium or bis(triphenylphosphine) palladium(II) chloride, in the inert solvent such as benzene, toluene, xylene, tetrahydrofuran, dioxane, dimethylformamide, preferably dioxane under suitable conditions.

For example, the reaction of phenylboronic acid with compound (4-1) may be carried out in a solvent such as benzene, toluene, dimethoxyethane, dimethylformamide, preferably dimethoxyethane, typically in the presence of a base such as potassium hydroxide, triethylamine, sodium bicarbonate, preferably sodium bicarbonate, or a combination of water and above compounds, preferably water and dimethoxyethane. The catalyst may be selected from those typically employed for the so-called Suzuki reaction (for example, tetrakis(triphenylphosphine)palladium, bis (triphenylphosphine)palladium(II) chloride, or {bis (diphenylphosphino)butane}palladium(II) chloride). The reaction is run at a temperature in the range from 20 to 160° C., usually 60 to 130° C. for 10 minutes to 5 days, usually 30 minutes to 15 hours. The procedures and conditions to carry out these coupling reactions are known to those in the art.

The compounds of formula (I) can be prepared by a reaction of compound (4-1) with an appropriate alkylamine or cyclic amine such as piperidine, piperazine, or morpholine, without solvent. This reaction proceeds at a temperature in the range from 20 to 250° C., preferably 80 to 150° C. for 10 minutes to 3 days, usually 30 minutes to 15 hours. This reaction may also be carried out in the presence of a catalyst, preferably tetrakis (triphenylphosphine)palladium or bis(tri-o-tolylphosphine) palladium(II) chloride, in the inert solvent such as benzene, toluene, xylene, tetrahydrofuran, dioxane, dimethylformamide, preferably dioxane under suitable conditions. The procedures and conditions to carry out these coupling reactions are known to those in the art. (for example, Buchwald, S. L. et al., *Angew. Chem. Int. Ed. Engl.*, 1995, 34, 1348.)

As the pyridylpyrrole compounds of this invention may possess at least one asymmetric center, they are capable of occurring in various stereoisomeric forms or configurations. Hence, the compounds can exist in separated (+)- and (−)-optically active forms, as well as in racemic or (±)-mixtures thereof The present invention includes all such forms within its scope. Individual isomers can be obtained by known methods, such as optically selective reaction or chromatographic separation in the preparation of the final product or its intermediate.

Insofar as the pyridylpyrrole compounds of this invention are basic compounds, they are capable of forming a wide variety of different salts with various inorganic and organic acids.

The acids which are used to prepare the pharmaceutically acceptable acid addition salts of the aforementioned pyridylpyrrole base compounds of this invention of formula (I) are those which form non-toxic acid addition salts, i.e., salts containing pharmaceutically acceptable anions, such as chloride, bromide, iodide, nitrate, sulfate or bisulfate, phosphate or acid phosphate, acetate, lactate, citrate or acid citrate, tartrate or bi-tartrate, succinate, maleate, fu marate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts.

The pharmaceutically acceptable salts of the present invention also include alkali or alkaline earth metal salts such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Quaternary salts obtained from compounds of the invention and $C_{1-4}$ alkyl halide are also included. The other pharmaceutically acceptable salts which can be used in the present invention are described in *J. Pharmacelitical Scienices*, 1977, 66, 1–19.

These salts can be prepared by conventional procedures.

METHOD OF TREATMENT

The compounds (I) of this invention prepared as mentioned above inhibit inflammatory stimuli-induced cytokines production such as tumor necrosis factor alpha (TNF-α) and interleukine-1β (IL-1β), and are useful in the treatment or alleviation of various cytokine-mediated diseases such as asthma, arthritis, inflammatory bowel disease (IBD), sepsis, septic shock, rhinitis, inflammation of organs (e.g. hepatitis), AIDS and various inflammatory diseases. Furthermore, the compounds of this invention inhibit inflammatory stimuli-induced synthesis of proteins that regulate adhesion of leukocytes to other leukocytes and to other cell types and have potential use in the treatment of inflammatory and immune disorders such as arthritis and IBD; cardiovascular diseases, psoriasis and transplant rejection.

The pyridylpyrrole compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for the treatment of inflammation.

The compounds (I) of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The ability of the compounds of the formula (I) to inhibit TNFα biosynthesis and CAMs expression may be demonstrated in vitro by the following procedures.

METHOD FOR DETERMINING THE INHIBITION OF TNFα BIOSYNTHESIS AND CAMs EXPRESSION

1. Cells and Cell Culture:

L929 cells are grown in minimum essential medium (MEM) (Gibco BRL NY) supplemented with 10% FCS, 50 U/mL penicillin and 50 μg/mL streptomycin. Human umbilical vein endothelial cells (HUVECs) are obtained from Morinaga and grown in endothelial growth medium (E-GM UV, Kurabou, Japan) supplemented with 10% fetal calf serum (FCS, Biowhitakker, Walkersyille, Md.), 10 ng/mL EGF, 1 μg/mL hydrocortisone, and 1:100 dilution of bovine brain extract (Kurabou, Japan) in 5% $CO_2$ at 37° C. A human promyelocytic cell line, HL-60 cells are grown in RPMI-1640 (Nissui Seiyaku, Tokyo, Japan) supplemented with 10% FCS plus penicillin (50 U/mL) and streptomycin (50 μg/mL).

The ability of the compounds of the formula (I) to inhibit TNFα biosynthesis may be demonstrated in vitro by the following procedure 2.

2. TNFα Production:

Human peripheral blood mononuclear cells (HPBMNC) are isolated from heparinized human whole blood by Ficoll-Paque (Pharmacia, Sweden) density centrifugation, washed with Ca—Mg free phosphate-buffered saline (PBS, Nissui Seiyaku, Tokyo, Japan), suspended in RPMI 1640 containing 10% FCS and plated into 48 well plates (Falcon, Becton Dickinson, N.J.) at $2\times10^6$ cells/well. Monocytes (HBMo) are allowed to adhere to the plate by incubating at 37° C. for 1 hour, then the supernatant is aspirated and refilled with fresh RPMI-1640 medium containing 1% FCS.

Test compounds are prepared as 100 mM dimethyl sulfoxide ($Me_2SO$) stock solutions and diluted with media to obtain final testing concentrations. HMo are incubated at 37° C. for 4 hours in the presence of LPS (E. coli. 055:B5, Difco, Mich.) of 10 μg/mL with the test compounds in dose ranges of 0.1 μM~100 μM. The assay is run in a volume of 200 μL/well. Supernatants are subjected to quantitation of TNFα by an L929 cell cytotoxicity assay. On the day of the experiment, L929 cells are detached by trypsin treatment, washed with MEM and resuspended with 1% FCS-containing MEM. L929 cells ($8\times10^5$ cells/well) in a volume of 50 μL are plated into flat-bottomed 96 well plate (Corning, N.Y.) and incubated with 50 μL of serially diluted supernatants in the presence of finally 0.5 μg/mL of actinomycin D (Wako, Japan) at 37° C. in 5% $CO_2$ for 18 hours. After incubation, the culture medium is removed and viable cells are stained with 0.2% crystal violet dissolved in 20% ethanol. The cells are washed with tapping water and air-dried at room temperature. Resulting crystal violet is dissolved in 100 μl of 100% methanol and the optical density is determined at 595 nm on a BIO—RAD plate reader (Richmond, Calif.). The concentration of TNFα is regressed by human recombinant TNFα (Wako, Japan) set as a standard. Percent inhibition is determined by comparing the absorbance of vehicle treated cells with drug treated cells. Linear regression analysis of the means of the inhibition values are used to determine the $IC_{50}$s.

Some compounds prepared in the Working Examples as described below were tested by this method, and showed an $IC_{50}$ value of 100 nM to 10 μM with respect to inhibition of TNFα biosynthesis.

The ability of the compounds of the formula (I) to inhibit CAMs expression may be demonstrated in vitro by the following procedures 3 and 4.

3. Cell ELISA:

Test compounds are diluted with media to obtain final testing concentrations. HUVECs ($1.2 \times 10^4$/well) grown in flat-bottomed, 96 well, culture plates (Corning, N.Y.) are stimulated with human TNFα (3 U/mL, Wako, Tokyo, Japan) in the presence or absence of test compounds. Cells are incubated for 6 hours, then washed in PBS, fixed in 4% paraformaldehyde for 15 minutes, washed and stored for 1–3 days at 4° C. in PBS.

Adhesion molecules are detected using ELISA. Cells are incubated with a primary antibody to either ICAM-1 (0.5 μg/mL) (BA#3, R&D Systems) or E-selectin (0.5 μg/mL) (BBA#1, R&D Systems). Anti-mouse Ig, peroxidase-linked species-specific F(ab')$_2$ fragment (from sheep) (Amersham; 1:2500 dilution) is used as the second antibody, followed by the addition of peroxidase substrate, o-phenylenediamine. The absorbance of each well is read with a Bio-Rad plate reader at 490 nm, and the background at 655 nm is subtracted. The absorbance of nonstimulated HUVECs is subtracted from the absorbance values of TNFα- stimulated cells. Percent inhibition is determined by comparing the absorbance of vehicle treated cells with drug treated cells. Linear regression analysis of the means of the inhibition values are used to determine the $IC_{50}$s.

Some compounds prepared in the Working Examples as described below were tested by this method, and showed an $IC_{50}$ value of 50 nM to 10 μM with respect to inhibition of the CAMs expression.

4. Cell Adhesion Assay:

BL-60 cells are induced to differentiate into granulocyte-like cells by 1.25% Me$_2$SO in RPMI-1640 supplemented with 10% heat-inactivated FCS for 5–6 days. Then cells are incubated with 300 μM of fluorescent dye, 5(6)-carboxyl fluorescein diacetate, for 30 minutes at 37° C. and washed three times with Hank's solution. HUVECs ($1.2 \times 10^4$/well) grown in 96 well plates are simultaneously treated with the test compounds which are diluted with media to obtain final testing concentrations and 30 U/mL TNFα for 6 hours. Labeled cells ($5 \times 10^5$/well) are added to TNFα- stimulated HUVECs in a final volume of 0.1 mL gently washing four times with warm Hank's solution, and remaining cells are lysed with 1% Nonidet P-40. The number of adherent cells are determined by measuring the fluorescence intensity using a Fluoroscan II (excitation at 485 nm and emission at 538 nm). Percent inhibition is determined by comparing the fluorescence intensity of vehicle treated cells with drug treated cells. Linear regression analysis of the means of the inhibition values are used to determine the $IC_{50}$s.

Some compounds prepared in the Working Examples as described below were tested by this method, and showed an $IC_{50}$ value of 50 nM to 10 μM with respect to inhibition of the adhesion of HL-60 to HUVECs stimulated by TNFα.

EXAMPLES

The present invention is illustrated by the following examples. However, it should be understood that the invention is not limited to the specific details of these examples. Melting points were taken with a Buchi micro melting point apparatus and uncorrected. Mass spectra were recorded on a JEOL JMS-AM120 or API-III (Perkin-Elmer SCIEX) triple-quadrupole mass analyzer. Infrared Ray absorption spectra (IR) were measured by a Shimazu infrared spectrometer (IR-470). $^1$H and $^{13}$C nuclear magnetic resonance spectra (NMR) were measured in CDCl$_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad. Coupling constants (J) are recorded in hertz. The following abbreviations are used: MeOH for methanol, EtOH for ethanol, DMSO for dimethylsulfoxide, DMF for N,N-dimethylformamide, THF for tetrahydrofuran, HCl for hydrogen chloride or CH$_2$Cl$_2$ for dichloromethane.

Example 1

3-Acetyl-4-methyl-2,5-di(4-pyridyl)-1H-pyrrole

To a stirred solution of 4-pyridinecarboxaldehyde (14.8 g ; 0.138 mol) and 2,4-pentanedione (12.5 g; 0.125 mol) in EtOH (15 mL) was added 25% aqueous ammonia solution (8 mL) at room temperature. The resulting mixture was stirred for 15 minutes at room temperature, and then heated at reflux temperature for 3 hours. After cooling, the obtained precipitates were collected by filtration to give 18.7 g. Recrystallization from EtOH provided the title compound (14.1 g, 41% yield) as a colorless solid. X-ray analysis (recrystallized from EtOH/H$_2$O) indicated the title structure.

mp: 237–239.5° C.; $^1$H-NMR (DMSO-d$_6$) δ 12.00 (br. s, 1H), 8.66 (dd, J=4.4, 1.9 Hz, 2H), 8.62 (dd, J=4.4, 1.9Hz, 2H), 7.54 (dt, J=4.4, 1.9Hz, 4H), 2.35 (s, 3H), 2.18 (s, 3H); MS (EI) m/z 277 (M$^+$); Anal. Calcd for C$_{17}$H$_{15}$N$_3$O: C, 73.63; H, 5.45; N, 15.15. Found: C, 73.44; H, 5.39; N, 15.20.

Example 2

3-Acetyl-4-methyl-2.5di(4-pyridyl)-1H-pyrrole Dihydrochloride Monohydrate

3-Acetyl-4-methyl-2,5-di(4-pyridyl)-1H-pyrrole was dissolved in 10% HCl-MeOH. After removal of volatiles, the crude salt was recrystallized from EtOH to give the title compound.

mp: 238–241° C. (Recryst. from EtOH); $^1$H-NMR (DMSO-d$_6$) δ 12.0 (s, 1H), 8.66 (dd, J=4.4, 1.9 Hz, 2H), 8.62 (dd, J=4.4, 1.9 Hz, 2H), 7.55 (dd, J=4.4, 1.5 Hz, 2H), 7.53 (dd, J=4.4, 1.5 Hz, 2H), 2.35 (s, 3H), 2.18 (s, 3H); MS (EI) m/z 278 (M+H); Anal. Calcd for C$_{17}$H$_{15}$N$_3$O 2HCl H$_2$O: C, 55.45; H, 5.20; N, 11.41; Cl, 19.25. Found: C, 55.21; H, 5.17; N, 11.48; Cl, 19.19.

The compounds from Example 3 to 7 were prepared according to the procedure of Example 1 using the corresponding 1,3-diones instead of 2,4-pentanedione.

Example 3

4-Ethyl-3-propanoyl-2,5-di(4-pyridyl)-1H-pyrrole mp: 209–211° C.; IR (KBr) ν 3500, 1660, 1600, 1460, 1430, 1420, 1220, 1000, 940, 840, 820 cm$^{-1}$; $^1$H-NMR (DMSO-d$_6$) δ 11.90 (br. s, 1H), 8.66 (dd, J=4.4 Hz, 1.5 Hz, 2H), 8.62 (dd, J=4.4 Hz, 1.5 Hz, 2H), 7.53 (dd, J=4.4 Hz, 1.5 Hz, 2H), 7.47 (dd, J=4.4 Hz, 1.5 Hz, 2H), 2.71 (q, J=7.3 Hz, 2H), 2.41 (q, J=7.3 Hz, 2H), 1.16 (t, J=7.3 Hz, 3H), 0.95 (t, J=7.3 Hz, 3H); Anal. Calcd. for C$_{19}$H$_{19}$N$_3$O: C, 74.73; H, 6.27; N. 13.76. Found: C, 74.68; H, 6.35; N, 13.69.

Example 4

3-Acetyl-2,5-di(4-pyridyl)-4-trifluoromethyl-1H-pyrrole mp: 250–255° C. (Recryst. from ethyl acetate) $^1$H-NMR: (DMSO-d$_6$) δ 12.50 (br. s, 1H), 8.72 (dd, J=4.4 Hz, 1.5 Hz, 2H), 8.68 (dd, J=4.4 Hz, 1.8 Hz, 2H), 7.88–7.83 (m, 2H), 7.67–7.61 (m, 2H), 2.32 (s, 3H); Anal. Calcd. for $C_{17}H_{12}N_3OF_3$: C, 61.63; H, 3.65; N, 12.68. Found: C, 61.79; H, 3.57; N, 12.48.

Example 5

4-Methyl-3-propanoyl-2,5-di(4-pyridyl)-1H-pyrrole mp: 237–238° C.; IR (KBr) ν 1670, 1600, 1460, 1430, 1410, 1320, 1000, 820 cm$^{-1}$; $^1$H-NMR (DMSO-d$_6$) δ 11.90 (br. s, 1H), 8.66–8.60 (m, 4H), 7.58–7.46 (m, 4H), 2.49–2.43 (m, 2H), 2.31 (s, 3H), 0.97 (t, J=7.3 Hz, 3H); MS (EI) m/z 291 (M$^+$); Anal. Calcd. for $C_{18}H_{17}N_3O$ 1.4H$_2$O: C, 68.29; H, 6.30; N, 13.27. Found: C, 67.93; H, 5.90; N, 12.97.

Example 6

4-Methyl-2,5-di(4-pyridyl)-3-pentanoyl-1H-pyrrole mp: 88–89° C. (Recryst. from ethyl acetate-hexane); IR (KBr) ν 3400, 1660,1600, 1460, 1440, 1320, 1000, 830 cm$^{-1}$; $^1$H-NMR: (DMSO-d$_6$) δ 11.95 (br. s, 1H), 8.65 (d, J=5.9 Hz, 2H), 8.61 (d, J=5.5 Hz, 2H), 7.55 (d, J=5.9 Hz, 2H), 7.48 (d, J=5.5 Hz, 2H), 2.50–2.41 (m, 2H), 2.30 (s, 3H), 1.47 (q, J=7.3 Hz, 2H), 1.22–1.08 (m, 2H), 0.75 (t, J=7.3 Hz, 3H); Anal. Calcd. for $C_{20}H_{21}N_3O$ 1.25H$_2$O: C, 70.26; H, 6.93; N, 12.29. Found: C, 70.15; H, 6.76; N, 12.40.

Example 7

3-Acetyl-4-phenyl-2,5-di(4-pyridyl)-1H-pyrrole mp: 208–210° C.; $^1$H-NMR (DMSO-d$_6$) δ 12.30 (br. s, 1H), 8.75–8.60 (m, 2H), 8.45–8.36 (m, 2H), 7.70–7.20 (m, 9H), 1.88 (s, 3H).

The compound of Example 8 was prepared according to the procedure of Example 1 using 4-quinolinecarboxaldehyde instead of 4-pyridinecarboxaldehyde.

Example 8

3-Acetyl-4-methyl-2,5-di(4-quinolyl)-1H-pyrrole mp >260° C. (recryst. from ethyl acetate-hexane); $^1$H-NMR: (CDCl$_3$) δ 10.24 (s, 1H), 8.74 (dd, J=4.0, 2.5 Hz, 2H), 8.03–7.83 (m, 4H), 7.73–7.50 (m, 4H), 7.39 (d, J=4.4 Hz, 1H), 7.33 (d, J=4.4 Hz, 1H), 2.27 (s, 3H), 1.87 (s, 3H); Anal. Calcd. for $C_{25}H_{19}N_3O$: C, 79.55; H, 5.07; N, 11.13. Found: C, 79.15; H, 5.08; N, 10.99.

Example 9

3-Acetyl-4-methyl-2-(4-pyridyl)-5-(4-quinolyl)-1H-pyrrole

To a stirred solution of 4-quinolinecarboxaldehyde (2.3 g; 14.8 mmol), 4-pyridinecarboxaldehyde (1.6 g ; 14.8 mmol) in EtOH (40 mL) was added 2,4-pentanedione (2 g; 20 mmol) and 25% aqueous ammonia solution (8 ml) at room temperature. The mixture was heated at reflux temperature for 18 hours. After cooling, volatiles were removed by evaporation. Chromatographic purification of the residue on silica gel eluting with CH$_2$Cl$_2$—EtOH (20:1→8:1) provided 1.1 g, which was recrystallized from EtOH to afford the title compound (0.82 g, 17% yield) as a pale yellow solid.

mp: 237–239° C.; $^1$H-NMR (CDCl$_3$) δ 10.84 (s, 1H), 8.70 (d, J=4.4 Hz, 1H), 8.39 (d, J=5.1 Hz, 2H), 7.95 (d, J=8.4 Hz, 1H), 7.87 (d, J=7.7 Hz, 1H), 7.64 (t, J=7.0 Hz, 1H), 7.52 (t, J=7.0 Hz, 1H), 7.40 (d, J=5.9 Hz, 2H), 7.26 (d, J=4.4 Hz, 1H), 2.31 (s, 3H), 2.16 (s, 3H); Anal. Calcd. for $C_{21}H_{17}N_3O$: C, 77.04; H, 5.23; N, 12.83. Found: C, 77.26; H, 5.23; N, 12.77.

Example 10

3-Ethoxycarbonyl-4-ethyl-2,5-di(4-pyridyl)-1H-pyrrole

To a stirred solution of ethyl propionylacetate (2.03 g, 13.7 mmol) in EtOH (10 mL) was added 4-pyridinecarboxaldehyde (2.92 g, 27.3 mmol) and 25% aqueous ammonia solution (4 mL, 58.8 mmol) at room temperature. The mixture was heated at reflux temperature for 7 hours. After cooling, the resulting precipitates were collected by filtration, and washed with ethyl acetate to give the title product (1.44 g, 37% yield) as a solid.

mp: 212–215° C.; $^1$H-NMR (DMSO-d$_6$) δ 8 11.99 (br. s, 1H), 8.62 (dt, J=4.4 Hz, 1.8 Hz, 4H), 7.53 (dt,J=4.4 Hz, 1.8 Hz, 4H), 4.14 (q, J=7.0 Hz, 2H), 2.81 (q, J=7.3 Hz, 2H), 1.22 (t, J=7.3 Hz, 3H), 1.13 (t, J=7.0 Hz, 3H); IR (KBr) ν 3000, 1700, 1600, 1580, 1460, 1280, 1170,1140, 1100,820cm$^{-1}$; Anal. Calcd. for $C_{19}H_{19}N_3O_2$: C, 71.01; H, 5.96; N, 13.07. Found: C, 71.05; H, 5.95; N, 12.98.

The compounds from Example 11 to 25 were prepared according to the procedure of Example 10 using the corresponding β-ketoesters instead of ethyl propionylacetate.

Example 11

3-Ethoxycarbonyl-4-methyl-2,5-di(4-pyridyl)-1H-pyrrole mp: 206–208° C.; IR (KBr) ν 1700, 1600, 1580, 1470, 1260, 1140, 1080, 820 cm$^{-1}$; $^1$H-NMR (DMSO-d$_6$) δ 12.01 (br. s, 1H), 8.65–8.55 (m, 4H), 7.57–7.46 (m, 4H), 4.14 (q, J=7.0 Hz, 2H), 2.40 (s, 3H), 1.13 (t, J=7.0 Hz, 3H); MS (EI) m/z 307 (M$^+$); Anal. Calcd. for $C_{18}H_{17}N_3O_2$: C, 70.34; H, 5.57; N, 13.64. Found: C, 70.18; H, 5.60; N, 13.45.

Example 12

3-Methoxycarbonyl-4-methyl-2,5-di(4-pyridyl-1H-pyrrole mp: 245–247° C. (Recryst. from ethyl acetate-EtOH); IR (KBr) ν 1700, 1600, 1460, 1360, 1260, 1080, 1000, 820 cm$^{-1}$; $^1$H-NMR (DMSO-d$_6$) δ 12.03 (br. s, 1H), 8.62 (d, J=5.8 Hz, 4H), 7.56 (d, J=5.8 Hz, 2H), 7.53 (d, J=5.8 Hz, 2H), 3.66 (s, 3H), 2.39 (s, 3H); Anal. Calcd. for $C_{17}H_{15}N_3O_2$: C, 69.61; H, 5.15; N 14,33. Found: C, 69.93; H, 5.09; N, 14.38.

Example 13

3-Benzyloxycarbonyl-4-methyl-2,5-di(4-pyridyl)-1H-pyrrole mp: 204–205° C. (Recryst. from water-EtOH); IR (KBr) ν 3400, 1700, 1600, 1550, 1250, 1150, 1060, 820, 690, 660 cm$^{-1}$; $^1$H-NMR (CDCl$_3$) δ 9.51 (br. s, 1H), 8.59–8.46 (m, 4H), 7.36–7.22 (m, 9H), 5.23 (s, 2H), 2.50 (s, 3H); MS (EI) m/z 369 (M$^+$); Anal. Calcd for $C_{23}H_{19}N_3O_2$2O H$_2$O: C, 71.30; H, 5.46; N, 10.85. Found: C, 71.36; H, 5.33; N, 10.90.

Example 14

3-Allyloxycarbonyl-4-methyl-2,5-di(4-pyridyl)-1H-pyrrole mp: 224–224.5° C. (Recryst. from water-EtOH); IR (KBr) ν 3450, 1690, 1600, 1580, 1460, 1270, 1140, 1080, 990, 830 cm$^{-1}$; $^1$H-NMR (DMSO-d$_6$) δ 12.05 (br. s, 1H), 8.63–8.59 (m, 4H), 7.57–7.52 (m, 4H), 5.95–5.80 (m, 1H), 5.18–5.16 (m, 1H), 5.12 (t, J=1.6 Hz, 1H), 4.63 (dt, J=1.4, 1.4 and 5.5 Hz, 2H), 2.41 (s, 3H); MS (EI) m/z, 319 (M$^+$); Anal. Calcd for C$_{19}$H$_{17}$N$_3$O$_2$: C, 71.46; H, 5.37; N, 13.16. Found: C, 71.61; H, 5.30; N, 13.13.

Example 15

4-Methyl-3-(1-methylethoxy)carbonyl-2,5-di(4-pyridyl)-1H-pyrrole mp: 218–221° C. (Recryst. from water-EtOH); I R(KBr) ν 3300, 1700, 1600, 1590, 1470, 1280, 1150, 1080, 1000, 830cm$^{-1}$; $^1$H-NMR (DMSO-d$_6$) δ 11.99 (br. s, 1H), 8.62 (d, J=6.2 Hz, 4H), 7.57–7.52 (m, 4H), 5.06–4.97 (m, IfH), 2.39 (s, 3H), 1.14 (d, J=6.2 Hz, 6H); Anal. Calcd for C$_{19}$H$_{19}$N$_3$O$_2$·0.65H$_2$O: C, 68.51; H, 6.14; N, 12.62. Found: C, 68.15; H, 6.18; N, 12.97; MS (EI) m/z, 321 (M$^+$).

Example 16

4-Methyl-3-(1,1-dimethylethoxy)carbonyl-2,5-di(4-pyridyl)-1H-pyrrole mp: 265–267° C. (Recryst. from water-EtOH); IR (KBr) ν 3450, 1690, 1610, 1580, 1340, 1270, 1150, 1080, 1000, 820 cm$^{-1}$; $^1$H-NMR (DMSO-d$_6$) δ 11.93 (br. s, 1H), 8.65–8.58 (m, 4H), 7.56–7.49 (m, 4H), 2.38 (s, 3H), 1.36 (s, 9H); MS (EI) m/z, 335 (M$^+$); Anal. Calcd for C$_{20}$H$_{21}$N$_3$O$_2$: C, 71.62; H, 6.31; N, 12.53. Found: C, 71.54; H, 6.31; N, 12.54.

Example 17

4-Methyl-3-propoxycarbonyl-2,5-di(4-pyridyl)-1H-pyrrole mp: 215–218° C. (Recryst. from water-EtOH); IR (KBr) ν 3400, 1700, 1600, 1590, 1460, 1280, 1140, 1080, 1000, 830 cm$^{-1}$; $^1$H-NMR (DMSO-d$_6$) δ 12.02 (br. s, 1H), 8.61 (d, J=5.9 Hz, 4H), 7.56–7.47 (m, 4H), 4.05 (t, J=6.4 Hz, 2H), 2.40 (s, 3H), 1.59–1.45 (m, 2H), 0.75 (t, J=7.3 Hz, 3H). MS (EI) m/z, 321 (M$^+$); Anal. Calcd for C$_{19}$H$_{19}$N$_3$O$_2$·0.8H$_2$O: C, 67.96; H, 6.18; N, 12.51. Found: C, 67.84; H, 6.16; N, 12.60.

Example 18

3-Ethoxycarbonyl-4-phenyl-2,5-di(4-pyridyl)-1H-pyrrole mp: 99–100° C. (Recryst. from ethyl acetate-hexane) IR (KBr) ν 3400, 1710, 1600, 1590, 1460, 1280, 1150, 1100, 1000,830 cm$^{-1}$; $^1$H-NMR (CDCl$_3$) δ 9.92 (br. s, 1H), 8.63–8.57 (m, 2H), 8.38–8.33 (m, 2H), 7.58–7.01 (m, 9H), 4.02 (q, J=7.2 Hz, 2H), 0.91 (t, J=7.2 Hz, 3H); MS (EI) m/z, 369 (M$^+$); Anal. Calcd for C$_{23}$H$_{19}$N$_3$O$_2$·1.2H$_2$O: C, 70.65; H, 5.52; N, 10.75. Found: C, 70.51; H, 5.34; N, 11.13.

Example 19

3-Butoxycarbonyl-4-methyl-2,5-di(4-pyridyl)-1H-pyrrole mp: 182–186° C. (Recryst. from ethanol-hexane) IR (KBr) ν 3400, 1700, 1600, 1580, 1460, 1260, 1140, 1080, 1000, 830 cm$^{-1}$; $^1$H-NMR (MSOd$_6$) δ 12.01 (br. s, 1H), 8.61 (d, J=5.9 Hz, 4H), 7.57–7.53 (m, 4H), 4.08 (t, J=6.4 Hz, 2H), 2.40 (s, 3H), 1.52–1.42 (m, 2H), 1.22–1.08 (m, 2H), 0.80 (t, J=7.3 Hz, 3H); MS (EI) m/z, 335 (M$^+$); Anal. Calcd for C$_{20}$H$_{21}$N$_3$O$_2$: C, 71.62; H, 6.31; N, 12.53. Found: C, 71.65; H, 6.39; N, 12.66.

Example 20

3-(2-Methoxyethoxy)carbonyl-4-methyl-2,5-di(4-pyridyl)-1H-pyrrole mp: 174–177° C. (Recryst. from water-EtOH); IR (KBr) ν 3450, 1700, 1600, 1580, 1470, 1260, 1080, 830 cm$^{-1}$; $^1$H-NMR (DMSO-d$_6$) δ 12.02 (br. s, 1H), 8.63–8.60 (m, 4H), 7.57–7.54 (m, 4H), 4.23 (t, J=4.6 Hz, 2H), 3.47 (t, J=4.6 Hz, 2H), 3.19 (s, 3H), 2.40 (s, 3H); MS (EI) m/z, 337 (M$^+$); Anal. Calcd for C$_{19}$H$_{19}$N$_3$O$_3$ H$_2$O: C, 64.21; H, 5.96; N, 11.82. Found: C, 63.97; H, 5.98; N, 11.80.

Example 21

3-Ethoxycarbonyl-4-propyl-2,9di(4-pyridyl)-1H-pyrrole mp: 209–211° C.; IR (KBr) ν 3500, 1690, 1600, 1580, 1460, 1270, 1140, 820 cm$^{-1}$; $^1$H-NMR (DMSO-d$_6$) δ 11.99 (br. s, 1H), 8.65–8.58 (m, 4H), 7.56–7.48 (m, 4H), 4.13 (q, J=7.3 Hz, 2H), 2.82–2.71 (m, 2H), 1.64–1.50 (m, 2H),1.13 (t, J=7.3 Hz, 0.92 (t, J=7.3 Hz, 3H); Anal. Calcd. for C$_{20}$H$_{21}$N$_3$O$_2$: C, 71.62 H, 6.31; N, 12.53. Found: C, 71.66; H, 6.34; N, 12.40.

Example 22

3-Ethoxycarbonyl-4-(1-methyethyl)-2,5-di(4-pyridyl)-1H-pyrrole mp: 245–247° C.; IR (KBr) ν 3000, 1700, 1600, 1580, 1460, 1300, 1260, 1180, 1140, 1100, 1030, 820 cm$^{-1}$; $^1$H-NMR (DMSO-d$_6$) δ 11.90 (br. s, 1H), 8.67–8.57 (m, 4H), 7.48–7.44 (m, 4H), 4.15 (q, J=7.0 Hz, 2H), 3.24–3.12 (m, 1H), 1.30 (d, J=7.0 Hz, 6H), 1.06 (t, J=7.0 Hz, 3H); Anal. Calcd. for C$_{20}$H$_{21}$N$_3$O: C, 71.62; H, 6.31; N, 12.53. Found: C, 71.32; H, 6.30; N, 12.36.

Example 23

3-Ethoxycarbonyl-4-butyl-2,5-di(4-pyridyl-1H-pyrrole mp: 256–258° C.; IR (KBr) ν 3000, 1700,1600, 1580, 1460, 1280, 1260, 1170, 1100, 1070, 820cm$^{-1}$; $^1$H-NMR (DMSO-d$_6$) δ 11.98 (br. s, 1H), 8.61 (dt, J=4.8 Hz, 1.5 Hz, 4H), 7.52 (dt, J=4.8 Hz, 1.5 Hz, 4H), 4.14 (dd, J=14.4 Hz, 7.3 Hz, 2H), 2.80–2.76 (m, 2H), 163–1.47 (m, 2H), 1.41–1.27 (m, 2H), 1.13 (t, J=7.3 Hz, 3H), 0.89 (t, J=7.3 Hz, 3H); Anal. Calcd. for C$_{21}$H$_{23}$N$_3$O$_2$: C, 72.18; H, 6.63; N, 12.03. Found: C, 71.85; H, 6.69; N, 11.98.

Example 24

3-Methoxycarbonyl-4-methoxymethyl-2,5-di(4-pyridyl)-1H-pyrrole mp: 97–99° C.; IR (KBr) ν 3400, 1710, 1600, 1590, 1470, 1260, 1200, 1080, 1000, 820 cm$^{-1}$; $^1$H-NMR (DMSO-d$_6$) δ 12.28 (br. s, 1H), 8.70–8.60 (m, 4H), 7.63 (d, J=4.8 Hz, 2H), 7.55 (d, J=4.8 Hz, 2H), 4.53 (s, 2H), 3.68 (s, 3H); 3.34 (s, 3H); Anal. Calcd. for C$_{18}$H$_{17}$N$_3$O$_3$ 1.0H$_2$O: C, 63.33; H, 5.61; N, 12.31. Found: C, 63.30; H, 5.64; N, 12.20.

Example 25

3-Ethoxycarbonyl-4-(4-nitrophenyl)-2,5-di(4-pyridyl)-1H-pyrrole mp: 274–276° C.; IR (KBr) ν 1700, 1600, 1580, 1510, 1470, 1440, 1380, 1140, 1100, 930 cm$^{-1}$; $^1$H-NMR (DMSO-d$_6$) δ 12.53 (br. s, 1H), 8.67 (d, J=4.8 Hz, 2H), 8.46 (d, J=4.8 Hz, 2H), 8.23 (d, J=4.8 Hz, 2H), 7.65 (d, J=4.8 Hz, 2H), 7.52 (d, J=4.4 Hz, 2H), 7.19 (d, J=4.7 Hz, 2H), 3.94 (q, J=7.3 Hz, 2H), 0.85 (t, J=7.3 Hz, 3H); Anal. Calcd. for C$_{23}$H$_{18}$N$_4$O$_4$: C, 66.66; H, 4.38; N, 13.52. Found: C, 66.39; H, 4.33; N, 13.33.

Example 26

3-Formyl-4-methyl-2,5-di(4-pyridyl)-1H-pyrrole

The titled compound was prepared according to the procedure of Example 1 using either trans-4-methoxy-3-buten-2-one or 1,1-dimethoxybutan-3-one instead of 2,4-pentanedione.

mp: 278–280° C. (recryst. from EtOH); IR (KBr) ν 1670, 1600, 1590, 1460, 1220, 1000, 820 cm$^{-1}$; $^1$H-NMR (DMSO-d$_6$) δ 12.31 (br. s, 1H), 9.94 (s, 1H), 8.70 (d, J=5.9 Hz, 2H), 8.65 (d, J=5.9 Hz, 2H), 7.68 (d, J=5.9 Hz, 2H), 7.60 (d, J=5.9 Hz, 2H), 2.50 (s, 3H); Anal. Calcd. for C$_{16}$H$_{13}$N$_3$O 1.0H$_2$O: C, 68.31; H, 5.37; N, 14.94. Found: C, 68.49; H, 5.35; N, 14.85.

Example 27

3-Metha nesulfonyl-4-methyl-2,5-di(4-pyridyl)-1H-pyrrole

The titled compound was prepared according to the procedure of Example 1 using methanesulfonyl acetone instead of 2,4-pentanedione.

mp: 232–234° C.; IR (KBr) ν 3350, 1600, 1410, 1290, 1120, 820, 770 cm$^{-1}$; $^1$H-NMR (DMSO-d$_6$) δ 12.34 (br. s, 1H), 8.64 (d, J=4.8 Hz, 4H), 7.57 (dd, J=10.0 Hz, 6.0 Hz, 4H), 3.19 (s, 3H), 2.44 (s, 3H); MS (EI) m/z 313 (M$^+$);

Example 28

3-Acetyl-4-ethyl-2,5-di(4-pyridyl)-1H-pyrrole

The suspension of sodium hydride (NaH) (60% oil dispersion, 1.78 g, 44.5 mmol) in DMSO (15 mL) was heated at 70° C. for 2.5 hours under nitrogen. After cooling, the resulting solution of methylsulfinyl carbanion was added to 3-ethoxycarbonyl-4-ethyl-2,5-di(4-pyridyl)-1H-pyrrole (1.43 g, 4.45 mmol). The mixture was heated at 70° C. for 1 hour under nitrogen. After cooling, the mixture was diluted with benzene (25 mL) and water (5 mL). Zinc (0.87 g, 13.4 mmol) was added to the resulting mixture, and then heated at reflux temperature for 15 hours. After cooling, water was added to the mixturethen extracted with ethyl acetate-EtOH (5:1, 100 mL×3). Combined organic layers were washed with brine (50 mL), dried over MgSO$_4$, and concentrated in vaciio. The crude product was purified by flash chromatography eluting with CH$_2$Cl$_2$—EtOH (5:1) to give the title product (270 mg, 21% yield) as a colorless solid.

mp: 241–243° C.; $^1$H-NMR (DMSO-d$_6$) δ 11.90 (br. s, 1H), 8.64–8.55 (m, 4H), 7.48 (d, J=4.4 Hz, 4H), 2.74–2.66 (m, 2H), 2.07 (s, 3H), 1.20–1.10 (m, 3H); IR (KBr) ν 1660, 1600, 1460, 1430, 1410, 1000, 820 cm$^{-1}$; MS (EI) m/z 291 (M$^+$); Anal. Calcd. for C$_{18}$H$_{17}$N$_3$O 0.3H$_2$O: C, 72.85; H, 5.98; N, 14.16. Found: C, 72.69; H, 5.98; N, 13.81.

The compounds from Example 29 to 32 were prepared according to the procedure of Example 28 using the corresponding methoxy- or ethoxycarbonylpyrroles instead of 3-ethoxycarbonyl-4-ethyl-2,5-di(4-pyridyl)-1H-pyrrole.

Example 29

3-Acetyl-4-propyl-2,5-di(4-pyridyl)-1H-pyrrole mp: 111–113° C.; IR (KBr) ν 3400, 1660, 1600, 1460, 1430, 1000, 830, 770, 520 cm$^{-1}$; $^1$H-NMR (DMSO-d$_6$) δ 11.96 (br. s, 1H), 8.68–8.58 (m, 4H), 7.55–7.48 (m, 4H), 2.76–2.64 (m, 2H), 2.12 (s, 3H), 1.64–1.45 (m, 2H), 0.92 (t, J=7.3 Hz, 3H).

Example 30

3-Acetyl-4-(1-methyethyl)-2,5-di(4-pyridyl)-1H-pyrrole mp: 270–275° C. (Recryst. from ethyl acetate); IR (KBr) ν 1670, 1600, 1450, 1420, 1350, 1250, 1000, 960, 820, 540 cm$^-$; $^1$H-NMR (DMSO-d$_6$) δ 11.89 (br. s, 1H), 8.65 (d, J=5.1 Hz, 4H), 7.46 (t, J=4.6 Hz, 4H), 3.18–3.07 (m, 1H), 2.16 (s, 3H), 1.26 (d, J=7.0 Hz, 6H); Anal. Calcd. for C$_{19}$H$_{19}$N$_3$O 0.4H$_2$O: C, 73.01; H, 6.38; N, 13.44. Found: C, 73.23; H, 6.25; N, 13.29.

Example 31

3-Acetyl-4-butyl-2,5-di(4-pyridyl)-1H-pyrrole mp: 93–95° C.; IR (KBr) ν 3400, 1660, 1600, 1460, 1430, 1000, 830 cm$^{-1}$; $^1$H-NMR (DMSO-d$_6$) δ 11.95 (br. s, 1H), 8.69–8.57 (m, 4H), 7.55–7.48 (m, 4H) 2.78–2.67 (m, 2H), 2.12 (s, 3H), 1.56–1.42 (m, 2H), 1.36–1.24 (m, 2H), 0.87 (t, J=7.3 Hz, 3H); Anal. Calcd. for C$_{20}$H$_{21}$N$_3$O 1.3H$_2$O: C, 70.07; H, 6.94; N, 12.26. Found: C, 70.02; H, 6.89; N, 11.94.

Example 32

3-Acetil-4-methoxymethyl-2,5-di(4-pyridyl)-1H-pyrrole mp: 154–156° C.; IR (KBr) ν 3500, 1660, 1600, 1460, 1430, 1270, 1090, 830, 820 cm$^{-1}$; $^1$H-NMR (DMSO-d$_6$) δ 12.21 (br. s, 1H), 8.68–8.62 (m, 4H), 7.61–7.52 (m, 4H), 4.44 (s, 2H), 3.33 (s, 3H), 2.28 (s, 3H); Anal. Calcd. for C$_{18}$H$_{17}$N$_3$O$_2$ 0.5H$_2$O: C, 68.34; H, 5.73; N, 13.28. Found: C, 68.68; H, 5.64; N, 13.18.

Example 33

3-Acetyl-4-hydroxymethyl-2,5-di(4-pyridyl)-1H-pyrrole

3-Acetyl-4-methoxymethyl-2,5-di(4-pyridyl)-1H-pyrrole (0.36 g, 1.17 mmol) was dissolved in 10% aqueous HCl solution (14 mL). The mixture was heated at 70° C. for 15 hours. After cooling, the mixture was neutralized with saturated aqueous sodium bicarbonate solution. Insolubles were filtered off, and the filtrate was extracted with ethyl acetate-EtOH (5:1, 200 mL×2). The combined organic layers were washed with brine (50 mL), dried over MgSO$_4$, and concentrated ill vaciio. The crude product was recrystallized from ethyl acetate to provide the title product (150 mg, 44% yield) as a solid.

mp: 205–207° C.; $^1$H-NMR (DMSO-d$_6$) δ 12.13 (br. s, 1H), 8.64 (d, J=5.1 Hz, 4H), 7.67 (d, J=4.8 Hz, 2H), 7.52 (d, J=4.8 Hz, 2H), 5.03 (t, J=4.4 Hz, 1H), 4.54 (d, J=4.4 Hz, 2H), 2.34 (s, 3H); IR (KBr) ν 3400, 1670, 1600, 1460, 1430, 1260, 1000, 840 cm$^{-1}$; Anal. Calcd. for C$_{17}$H$_{15}$N$_3$O$_2$ 0.75H$_2$O: C, 66.55; H, 5.42; N, 13.69. Found: C, 66.80; H, 5.08; N, 13.37.

Example 34

3-(1-Rydroxyethyl)-4-methyl-2,5-di(4-pyridyl)-1H-pyrrole

To a stirred solution of 3-acetyl-4-methyl-2,5-di(4-pyridyl)-1H-pyrrole (1.11 g; 4.0 mmol) in EtOH (12 mL)

was added sodium borohydride (NaBH4) (0.15 g; 4.0 mmol) at room temperature. After stirring for 1 hour, additional NaBH4 (0.05 g; 1.3 mmol) was added. The mixture was stirred for 30 minutes, and then volatiles were removed by evaporation. Water (30 mL) was added to the reaction mixture, and the whole was extracted with ethyl acetate-EtOH (10:1, 70 mL×3). Combined organic layers were washed with water (50 mL), brine (50 mL), dried over $MgSO_4$, and concentrated in vaciio. The residue was recrystallized from EtOH to give the title compound (0.432 g, 39% yield) as a colorless solid.

mp: 250–252° C.; $^1$H-NMR (DMSO-$d_6$) δ 11.29 (s, 1H), 8.59 (dd, J=6.2, 1.8 Hz, 2H), 8.56 (dd, J=6.2, 1.8 Hz, 2H), 7.56 (dd, J=4.8, 1.8 Hz, 2H), 7.54 (dd, J=4.8, 1.8 Hz, 2H), 5.00 (s, 1H), 4.98 (q, J=6.6 Hz, 1H), 2.38 (s, 3H), 1.45 (d, J=6.6 Hz, 3H); Anal. Calcd. for $C_{17}H_{17}N_3O$ $0.1H_2O$: C, 72.63; H, 6.17; N, 14.95. Found: C, 72.47; H, 6.14; N, 14.86.

Example 35

4-Methyl-3-(methyloxyimino-1-ethyl-2,5-di(4-pyridyl-1H-pyrrole hydrochloride

To a stirred solution of 3-acetyl-4-methyl-2,5-di(4-pyridyl)-1H-pyrrole (0.7 g; 2.5 mmol) in ethanol-pyridine (8 mL×2 mL) was added O-methylhydroxylamine hydrochloride (0.27 g; 3.3 mmol) at room temperature, and the mixture was stirred for 15 hours. The resulting precipitates were collected by filtration, and the obtained solid was recrystallized from EtOH-MeOH to give the title product (0.16 g, 19% yield) as a colorless solid.

mp: 213–216° C. (recryst. from EtOH); $^1$H-NMR (DMSO-$d_6$) δ 13.1 (s, 1H), 8.90 (d, J=6.5 Hz, 2H), 8.87 (d, J=7.0 Hz, 2H), 8.37 (d, J=7.0 Hz, 2H), 7.81 (d, J=6.5 Hz, 2H), 3.90 (s, 3H), 2.33 (s, 3H), 2.12 (s, 3H); MS (EI) m/z 306 (M$^+$); Anal. Calcd. for $C_{18}H_{18}N_4O$ 1.8HCl $1.6H_2O$: C,53.94; H, 5.78; N, 13.98; Cl, 15.92. Found: C, 53.65; H, 5.57; N, 13.76; Cl, 15.67.

Example 36

3-Acetyl-4-methyl-2,5-di(4-pyridyl)-1H-pyrrole-N,N'-dioxides and a Mixture of 4-{3-acetyl-4-methyl-5-(4-pyridyl)-1H-pyrrol-2-yl}pyridine-N-oxide and 4-{3-acetyl-4-methyl-2-(4-pyridyl)-1H-pyrrol-5-yl}pyridine-N-oxide (2.5:1)

To a stirred suspension of 3-acetyl-4-methyl-2,5-di(4-pyridyl)-1H-pyrrole (1.0 g; 3.6 mmol) in $CH_2Cl_2$ (15 mL) was added m-chloroperbenzoic acid (MCPBA) (0.71 g; 2.9 mmol) at room temperature. After stirring for 30 minutes, volatiles were removed by evaporation. The residue was purified by flash chromatography eluting with $CH_2Cl_2$—EtOH (10:1→6:1) to give mono-oxide (0.24 g, 23% yield) as less polar product and dioxide (0.2 g, 18% yield) as polar product.
less polar product:
mp: >280° C.; $^1$H-NMR (DMSO-$d_6$) δ 11.98 (s, 1H), 8.65 (d, J=7.3 Hz, 2H), 8.27 (d, J=7.3 Hz, 2H), 7.57 (d, J=7.3 Hz, 2H), 7.52 (d, J=7.3 Hz, 2H), 2.31 (s, 3H), 2.17 (s, 3H); MS (EI) m/z 293 (M$^+$); Anal. Calcd. for $C_{17}H_{15}N_3O_2$ $0.1H_2O$: C, 69.19; H, 5.19; N, 14.24. Found: C, 69.14; H, 5.10; N, 14.18.
more polar product:
mp: 301–302° C. (recryst. from ethyl acetate); $^1$H-NMR (DMSO-$d_6$) δ 11.91 (s, 1H), 8.28 (d, J=6.3 Hz, 2H), 8.27 (d, J=6.3 Hz, 2H), 7.56 (d, J=6.3 Hz, 2H), 7.54 (dd, J=6.3 Hz, 2H), 2.31 (s, 3H), 2.24 (s, 3H); MS (EI) m/z 309 (M$^+$); Anal. Calcd. for $C_{17}H_{15}N_3O_3$: C, 66.01; H, 4.89; N, 13.58. Found: C, 65.65; H, 4.88; N, 13.41.

Exanmple 37

3-Acetyl-1-methoxymethyl-4-methyl-2,5-di(4-pyridyl)-1H-pyrrole

To a stirred solution of 3-acetyl-4-methyl-2,5-di(4-pyridyl)-1H-pyrrole (1.0 g, 3.6 mmol) in DMF (5 mL) was added NaH (60% oil dispersion; 0.29 g, 7.2 mmol) at room temperature. The mixture was heated at 70–80° C. for 30 minutes, and after cooling to 0° C., chloromethyl methyl ether (0.41 mL, 5.4 mmol) was added. The mixture was stirred for 15 hours, and saturated aqueous $NaHCO_3$ (30 mL) was added to the reaction mixture. The whole was extracted with ethyl acetate (50 mL×3). Combined organic layers were washed with water (50 mL), brine (50 mL), dried over $MgSO_4$, and concentrated in vactio. The residual oil was purified by preparative TLC (1 mm×3) to give the title compound (0.1 g, 9% yield) as a light brown powder.

$^1$H-NMR (CDCl$_3$) δ 8.78–8.71 (m, 4H), 7.47–7.40 (m, 4H), 4.68 (s, 2H), 3.12 (s, 3H), 2.26 (s, 3H), 2.03 (s, 3H); MS (EI) m/z 321 (M$^+$); Anal. Calcd. for $C_{19}H_{19}N_3O_2$ $0.6H_2O$: C, 68.70; H, 6.13; N, 12.65. Found: C, 68.61; H, 5.92; N, 12.31.

Example 38

3-Acetyl-1-(2-methoxy-1-ethyl)-4-methyl-2,5-di(4-pyridyl)-1H-pyrrole

The title compound was prepared according to the procedure of Example 37 using 2-chloro ethyl methyl ether instead of chloromethyl methyl ether.

mp: oil; $^1$H-NMR (CDCl$_3$) δ 8.76 (dd, J=4.4, 1.4 Hz, 2H), 8.72 (dd, J=4.4, 1.4 Hz, 2H), 7.38 (dd, J=4.4, 1.4 Hz, 2H), 7.29 (dd, J=4.4, 1.4 Hz, 2H), 3.89 (t, J=5.9 Hz, 2H), 3.00 (t, J=5.9 Hz, 2H), 2.97 (s, 3H), 2.21 (s, 3H), 1.98 (s, 3H).

Example 39

3-Hydroxymethyl-4-methyl-2,5-di(4-pyridyl)-1H-pyrrole
3-Ethoxycarbonyl-1-methoxymethyl-4-methyl-2,5-di(4-pyridyl)-1H-pyrrole The subtitle compound was prepared according to the procedure of Example 37 using 3-ethoxycarbonyl-4-methyl-2,5-di(4-pyridyl)-1H-pyrrole instead of 3-acetyl-4-methyl-2,5-di(4-pyridyl)-1H-pyrrole.

$^1$H-NMR (CDCl$_3$) δ 8.72 (t, J=1.8 Hz, 2H), 8.70 (t, J=1.8 Hz, 2H), 7.42–7.38 (m, 4H), 4.72 (s, 2H), 4.14 (q, J=7.0 Hz, 2H), 3.08 (s, 3H), 2.29 (s, 3H), 1.06 (t, J=7.0 Hz, 3H).
3-Hydroxymethyl-1-methoxymethyl-4-methyl-2,5-di(4-pyridyl)-1H-pyrrole To a stirred suspension of lithium aluminum hydride (LAH) (88 mg, 2.31 mmol) was added 3-ethoxycarbonyl-1-methoxymethyl-4-methyl-2,5-di(4-pyridyl)-1H-pyrrole (270 mg, 0.77 mmol) at 0° C. under nitrogen. After stirring for 2 hours, the reaction mixture was allowed to warm to room temperature and stirred for 3 days. Saturated aqueous ammonium chloride solution (50 mL) was added to the mixture, and the whole was extracted with ethyl acetate (70 mL×2). Combined organic layers were washed. with brine (50 mL), dried over $MgSO_4$, and concentrated il vacuo to afford the subtitle compound (180 mg, 5.8% yield) as a solid.

mp: 181–183° C.; $^1$H-NMR (CDCl$_3$) δ 8.70–8.66 (m, 4H), 7.57 (dd, J=4.4 Hz, 1.5 Hz, 2H), 7.44 (dd, J=4.4 Hz, 1.5 Hz, 2H), 4.82 (s, 2H), 4.53 (s, 2H), 3.19 (s, 3H), 2.22 (s, 3H).
3-Hydroxymethyl-4-methyl-2,5-di(4-pyridyl)-1H-pyrrole
3-Hydroxymethyl-1-methoxymethyl-4-methyl-2,5-di(4-pyridyl)-1H-pyrrole (150 mg, 0.49 mmol) was dissolved in 10% aqueous HCl solution (20 mL) and the mixture was stirred for 1 day at room temperature then heated at reflux temperature for 1 hour. After cooling, the mixture was neutralized with saturated aqueous sodium bicarbonate solution. Volatiles were removed by evaporation, and the residue was suspended in EtOH. After removal of insolubles by filtration, the filtrate was concentrated in vacto. The crude product was purified by flash chromatography eluting with $CH_2Cl_2$—EtOH (5:1), followed by recrystallization from EtOH to give the title compound (30 mg, 23% yield) as a solid.

mp: 258–261° C.; $^1$H-NMR (DMSO-$d_6$) δ 11.44 (br. s, 1H), 8.61–8.56 (m, 4H), 7.72–7.56 (m, 4H), 4.94 (t, J=4.8 Hz, 1H), 4.41 (d, J=4.8 Hz, 2H), 2.29 (s, 3H); Anal. Calcd. for $C_{16}H_{15}N_3O$ 0.8$H_2O$: C, 68.70; H, 5.98; N, 15.02. Found: C, 68.90; H, 5.56; N, 14.71.

Example 40

3-Aminocarbonyl-4-methyl-2,5-di(4-pyridyl)-1H-pyrrole

3-Cyano-4-methyl-2,5-di(4-pyridyl)-1H-pyrrole (200 mg, 0.77 mmol) was dissolved in sulfuric acid (3 mL) and the mixture was stirred for 15 hours at 85° C. After cooling, fuing sulfuric acid (1 drop) was added to the reaction mixture and stirred for 1 hour at room temperature. The reaction mixture was neutralized by saturated aqueous $NaHCO_3$ solution, and the resulting precipitates were collected by filtration. Recrystallization from EtOH gave the title compound (110 mg, 51% yield).

mp: 212–215° C.; IR (KBr) ν 3400, 1640, 1600, 1480, 1420, 1380, 1320, 1000, 820, 520 cm$^{-1}$; $^1$H-NMR (DMSO$d_6$) δ 11.63 (br. s, 1H), 8.60 (d, J=6.2 Hz, 2H), 8.55 (d, J=6.2 Hz, 2H), 7.63 (d, J=6.2 Hz, 2H), 7.62 (br. s, 1H), 7.57 (d, J=6.2 Hz, 2H), 7.34 (br, s, 1H), 2.26 (s, 3H); MS (EI) m/z 278 (M$^+$);

Example 41

3-Carboxyl-4-methyl-2,5-di(4-pyridyl)-1H-pyrrole Morpholinium Salt

To a solution of 3-allyloxycarbonyl-4-methyl-2,5-di(4-pyridyl)-1H-pyrrole (100 mg, 0.313 mmol) in TBIF (4 mL) including 10% DMSO were added Pd(PPh$_3$)$_4$ (36.2 mg, 0.0313 mmol) and morpholine (0.27 ml, 3.13 mmol) at room temperature. The mixture was stirred for 5 hours at the same temperature under Ar in the dark and then evaporated to give an oily residue, which was crystallized from ethyl acetate. The solid was recrystallized from MeOH to afford 30.2 mg of the title compound as a morpholinium salt.

mp: 223–224° C. (Recryst. from MeOH); IR (KBr) ν 3400, 1600, 1560, 1480, 1430, 1370, 1310, 1220, 830 cm$^{-1}$; $^1$H-NMR (DMSO-$d_6$) δ 11.84 (br. s, 1H), 8.61–8.57 (m, 4H), 7.63–7.54 (m, 4H), 3.50 (t, J=4.6 Hz, 2H), 2.67 (t, J=4.8 Hz, 2H), 2.54 (s, 5H), 2.38 (s, 2H); MS (FAB) m/z, 280 (M$^+$H)$^+$.

Example 42

3-Acetyl-2-methyl-4,5-di(4-pyridyl)1H-pyrrole

To a stirred solution of y-pyridoin (1.8 g, 8.4 mmol) (prepared according to the procedure of litrature; Japanese Kokai Publication H07-00273 7) and 2,4-pentanedione (1.35 g, 13.5 mmol) in acetic acid (20 mL) was added ammonium acetate (2.6 g, 33.7 mmol) at room temperature. The resulting mixture was heated at reflux temperature for 9 hours, and stirred at room temperature overnight. Volatiles were removed by evaporation, and the mixture was neutralized by saturated aqueous $NaHCO_3$. The whole was extracted with ethyl acetate (50 mL×3), $CH_2Cl_2$—EtOH (5:1, 50 mL×2), dried over $MgSO_4$, and concentrated in vacito. The residue was purified by flash chromatography eluting with $CH_2Cl_2$—EtOH (15:1->10:1) to give the title compound (0.2 g, 9% yield) as a colorless solid.

mp: 236–239° C.; $^1$H-NMR (DMSO-$d_6$) δ 12.03 (s, 1H), 8.57 (d, J=5.9 Hz, 2H), 8.38 (d, J=6.2 Hz, 2H), 7.27 (d, J=5.9 Hz, 2H), 7.03 (d, J=6.2 Hz, 2H), 2.53 (s, 3H), 1.93 (s, 3H); Anal. Calcd. for $C_{17}H_{15}N_3O$ 0.2$H_2O$: C, 72.68; H, 5.53; N, 14.96. Found: C, 72.72; H, 5.43; N, 14.89.

Example 43

3-Acetyl-2-methyl-5-(4-pyridyl)-1H-pyrrole

A mixture of 4-(bromoacetyl)pyridine hydrobromide (2.64 g, 10 mmol), 2,4-pentadione (1.62 g, 16 mmol), and $NH_4OAc$ (3.1 g, 40 mmol) in AcOH (25 mL) was heated under reflux temperature for 17 hours. After cooling, 10% aqueous KOH solution and saturated aqueous $NaHCO_3$ solution was added to this resulting solution until becoming basic solution (pH=8~9). The whole was extracted with ethyl acetate (50 mL×3), and the combined organic layers were washed with brine (20 mL), dried over $MgSO_4$, and concentrated in vactio. The residue was purified by flash chromatography eluting with $CH_2Cl_2$—EtOH (20–15:1) to afford the title compound (70 mg, 4% yield).

mp 236–237° C.; $^1$H-NMR (DMSO-$d_6$) δ 11.90 (s, 1H), 8.50 (d, J=6.2 Hz, 2H), 7.62 (d, J=6.2 Hz, 2H), 7.28 (d, J=2.6 Hz, 1H), 2.50 (s, 3H), 2.36 (s, 3H); IR (nujol) ν 1650, 990, 730 cm$^{-1}$; MS (EI) m/z 200 (M$^+$); Anal. Calcd for $C_{12}H_{12}N_2O$: C, 71.68; H, 6.06; N, 13.86. Found: C, 71.98, H, 6.04; N, 13.99.

Example 44

3-Ethoxycarbony-4-methyl-5phenyl-2-(4-pyridyl)-1H-pyrrole

A mixture of 1-amino-1-phenyl-propan-2-on hydrochloride (10.5 g, 50.5 mmol), ethyl isonicotinoylacetate (8.1 g, 42.1 mmol), and ammonium acetate (6.5 g, 84.2 mmol) in acetic acid (50 mL) was heated under reflux temperature for 6 hours. After cooling, the mixture was diluted with ice-water (50 mL). The whole was extracted with $CH_2Cl_2$ (30 mL×3), and the combined organic layers were dried over $MgSO_4$, and concentrated in vaciio. The residue was purified by flash chromatography eluting with hexane-ethyl acetate (2 : 1) to afford the title product (2.1 g, 16% yield) as a pale yellow solid.

mp 179–181° C.; $^1$H-NMR (CDCl$_3$) δ 9.53 (s, 1H), 8.49 (d, J=5.9 Hz, 2H), 7.50–7.27 (m, 7H), 4.24 (q, J=7.3 Hz, 2 H), 2.41 (s, 3H), 1.23 (t, J=7.3 Hz, 3H); IR (KBr) ν 3000, 1698, 1600, 1470, 1250, 1070, 700 cm$^{-1}$; MS (EI) m/z 306 (M$^+$); Anal. Calcd for $C_{19}H_{18}N_2O$ 0.2 $H_2O$: C, 73.62; H, 5.98; N, 9.04. Found: C, 73.67; H, 5.85; N, 9.00.

Example 45

3-Actyl-2,4-dimethyl-5-(4-pyridyl)-1H-pyrrole

Method A
3-Acetyl-2,4-dimethyl-1-{2-(trimethylsilyl)ethoxymethyl}-1H-pyrrole (Step 1)

To a stirred solution of 3-acetyl-2,4-dimethyl-1H-pyrrole (commercially available from Aldrich Chem. Co. Inc., 1.50 g, 10.6 mmol) in DMF (40 mL) was added NaH (60% oil dispersion, 0.85 g, 21.2 mmol) at room temperature under nitrogen. After stirring for 30 minutes at room temprature the resulting suspension was cooled to 0° C. and added 2-(trimethylsilyl)ethoxymethyl chloride (3 mL, 15.9 mmol). The reaction mixture was warm to room temperature and stirred for 3 hours. The mixture was quenched with aqueous saturated NaHCO$_3$ solution, and the whole extracted with diethyl ether (100 mL×2). The combined organic layers were washed with brine (50 mL), dried over MgSO$_4$, concentrated iii vaciio. Chromatographic purification of the crude product eluting ethyl acetate-hexane (1:10) gave the subtitle product (2.32 g, 82% yield).

$^1$H-NMR (CDCl$_3$) δ 6.37 (s, 1H), 5.09 (s, 2H), 3.44 (t, J=8.1 Hz, 2H), 2.50 (s, 3H), 2.40 (s, 3H), 2.22 (s, 3H), 0.87 (t, J=8.1 Hz, 2H), −0.04 (s, 9H).

3-Acetyl-5-bromo-2,4-dimethyl-1-{2-(trimethylsilyl) ethoxymethyl-}-1H-pyrrole(Step 2)

To a stirred solution of 3-acetyl-2,4-dimethyl-1-{2-(trimethylsilyl)ethoxymethyl}-1H-pyrrole (1.75 g, 6.91 mmol) in THF (40 mL) was added N-bromosuccinimide (NBS; 1.29 g, 7.25 mmol) at −78° C. under nitrogen. After stirring for 30 minutes at same temperature, the mixture was allowed to warm to room temperature and stirred for 1 hour. Volatiles were removed by evaporation and the residue was purified by flash chromatography eluting with ethyl acetate-hexane (1:15) to give the subtitle product (1.50 g, 67%).

$^1$H-NMR (CDCl$_3$) δ 5.30 (s, 2H), 3.56 (t, J=8.1 Hz, 2H), 2.57 (s, 3H), 2.44 (s, 3H), 2.26 (s, 3H), 0.91 (t, J=8.1 Hz, 2H), 0.00 (s, 9H).

3-Acetyl-2,4-dimethyl-5-(4-pyridyl)-1-{2-(trimethylsilyl) ethoxymethyl}-1H-pyrrole (Step 3)

To a stirred solution of 3-acetyl-5-bromo-2,4-dimethyl-1-{2-(trimethylsilyl)ethoxymethyl}-1H-pyrrole (309 mg, 0.85 mmol) in toluene (5 mL) was added diethyl(4-pyridyl) borane [prepared according to the method of M. Terashima et al., *Heterocycles*, 1984, 22, 2471] (250 mg, 1.70 mmol), potassium hydroxide (85% purity, 168 mg, 2.55 mmol), and tetrakis(triphenylphosphine)palladium (0) (100 mg, 0.085 mmol) at room temperature under nitrogen. The mixture was heated at reflux temperature for 3 hours. After cooling, volatiles were removed by evaporation. The residue was purified by flash chromatography eluting with ethyl acetate-hexane (1:1) to give the title product (105 mg, 36% yield).

$^1$H-NMR (CDCl$_3$) δ 8.73–8.66 (m, 2H), 7.31–7.26 (m, 2H), 5.05 (s, 2H), 3.38 (dd, J=8.3 Hz, 8.1 Hz, 2H), 2.62 (s, 3H), 2.50 (s, 3H), 2.22 (dd, J=8.3 Hz, 8.1 Hz, 2H), −0.01 (s, 9H).

3-Acetyl-2,4-dimethyl-5-(4-pyridyl)-1H-pyrrole (Step 4)

3-Acetyl-2,4-dimethyl-5-(4-pyridyl)-1-{2-(trimethylsilyl)ethoxymethyl}-1H-pyrrole (1.12 g, 3.39 mmol) was dissolved with EtOH (10 mL) and 10% aqueous HCl solution (30 mL) and the mixture was heated at 85° C. for 4 hours. After cooling, the mixture was neutralized with saturated aqueous NaHCO$_3$ solution. The whole was extracted with ethyl acetate (150 mL×2), and the combined organic layers were washed with brine (50 mL), dried over MgSO$_4$, and concentrated in vactio. The resulting solid was a mixture of 3-acetyl-1-hyroxymethyl-2,4-dimethyl-5-(4-pyridyl)-1H-pyrrole and 3-acetyl-2,4-dimethyl-5-(4-pyridyl)-1H-pyrrole. This mixture was suspended with saturated aqueous sodium acetate solution and then heated at reflux temperature for 15 minutes. After cooling, this mixture was extracted with ethyl acetate (100 mL×2). The combined organic layers were washed with brine (50 mL), dried over MgSO$_4$, and concentrated in vacuo. The residue was recrystallized from ethyl acetate-hexane to give the title product (205 mg, 28% yield) as a pale yellow solid.

mp: 205–207° C.; IR: ν 3250, 1620, 1605, 1460, 1420, 1170, 1080, 955, 820 cm$^{-1}$; $^1$H-NMR (DMSO-d$_6$) δ 11.52 (br. s, 1H), 8.56 (dd, J=4.4 Hz, 1.5 Hz, 2H), 7.42 (dd, J=4.4 Hz, 1.5 Hz, 2H), 2.50 (s, 3H), 2.37 (s, 6H); MS (EI) m/z 214 (M$^+$); Anal. Calcd. for C$_{13}$H$_{14}$N$_2$O 0.1H$_2$O: C, 72.27; H, 6.62; N, 12.96. Found: C, 72.09; H, 6.75; N, 12.60.

Method B

3-Acetyl-2,4-dimethyl-5-(4-pyridyl)-1-{2-(trimethylsilyl)ethoxymethyl}-1H-pyrrole can be prepared by the use of tri-n-butyl(4-pyridyl)stannane instead of diethyl(4-pyridyl)borane in step 3 as follows;

To a stirred solution of 3-acetyl-5-bromo-2,4-dimethyl-1-{2-(trimethylsilyl)ethoxymethyl}-1H-pyrrole (1.50 g, 4.65 mmol) in dioxane (50 mL) was added tri-butyl(4-pyridyl)stannane [prepared according to the method of V. Snieckus et al., *J. Org. Chem.*, 1995, 60, 292] (1.71 g, 4.65 mmol), lithium chloride (0.49 g, 11.6 mmol) and tetrakis (triphenylphosphine)palladium (0.54 g, 0.47 mmol) at room temperature under nitrogen. The mixture was heated at reflux temperature for 2 days, additional tributyl(4-pyridyl) stannane (1.00 g, 2.72 mmol) and tetrakis (triphenylphosphine)palladium (0.50 g, 0.43 mmol) were added to the reaction mixture. After stirring at reflux temperature for 3 days, tributyl(4-pyridyl)stannane (1.00 g, 2.72 mmol) and tetrakis(triphenylphosphine)palladium (0.37 g, 0.32 mmol) were added again to the mixture. Then the mixture was stirred at reflux temperature for additional 2 days. After cooling, the mixture was filtered through celite pad, and the filtrate was concentrated in vactio. The residue was purified by flash chromatography eluting with ethyl acetate-hexane (1:2.5) to give the subtitle product (1.12 g, 73% yield).

Method C

Alternatively, 3-acetyl-2,4-dimethyl-5-(4-pyridyl)-1H-pyrrole was prepared more efficiently as follows;

3-Acetyl-5-bromo-2,4-dimethyl-1H-pyrrole (Step 1)

To a stirred suspension of 3-acetyl-2,4-dimethyl-1H-pyrrole (2.89 g, 21.1 mmol) in THF (80 mL) was added NBS (3.75 g, 21.1 mmol) at −78° C. under nitrogen. After stirring for 30 minutes at same temperature, the mixture was allowed to warm to room temperature and stirred for 1 hour. Sodium sulfite (4.3 g) was added to the mixture and volatiles were removed by evaporation. Water (100 mL) was added to the mixture, and the precipitates were collected by filtration to give 5.33 g (quant. including water) of the subtitle product.

$^1$H-NMR (CDCl$_3$) δ 8.08 (br. s, 1H), 2.49 (s, 3H), 2.42 (s, 3H), 2.22 (s, 3H).

3-Acetyl-2,4-dimethyl-5-(4-pyridyl)-1H-pyrrole (Step 2)

To a stirred solution of 3-acetyl-5-bromo-2,4-dimethyl-1H-pyrrole (5.33 g, 21.1 mmol, including water) in dimethoxyethane (DME; 60 mL) added water (20 mL), sodium bicarbonate (5.32 g, 63.3 mmol), 4-pyridineboronic acid [prepared according to the method of Fischer F. C. et al., *J. Red. Trav. Chim. Pays-Bays*, 1965, 84, 439.] (3.11 g, 25.3 mmol) and bis(triphenylphosphine)palladium(II)chloride (1.48 g, 2.11 mmol) at room temperature under nitrogen. The mixture was heated at reflux temperature for 8 hours, 4-pyridineboronic acid (0.5 g, 4.07 mmol) and bis (triphenylphosphine)palladium(II)chloride (1.48 g, 2.11 mmol) were additionally added to the reaction mixture and stirred at reflux temperature for 6 hours. After cooling, the reaction mixture was filtered through celite pad. The filtrate was diluted with ethyl acetate (150 mL), and the whole was washed with water (50 mL). The aqueous layer was extracted with ethyl acetate (150 mL), and the combined organic layers were washed with brine (50 mL) and 10% aqueous HCl solution (100 mL×2). The combined acidic aqueous layers were neutralized with saturated aqueous $NaHCO_3$ solution. The whole was extracted with ethyl acetate (100 mL×3), and the combined organic layers were dried over $MgSO_4$, and concentrated in vacuo. The resulting solids were washed with diethylether to give 2.00 g of crude product, which was recrystallized from MeOH to give the title product (1. 13 g, 25% yield).

Example 46

3-Acetyl-4-methyl-2-phenyl-5-(4-pyridyl)-1H-pyrrole

3-Acetyl-4-methyl-2-phenyl-1H-pyrrole and 3-Acetyl-4-methyl-5-phenyl-1H-pyrrole (Step 1)

NaH (60% oil dispersion; 700 mg, 17.5 mmol) was washed with dry $Et_2O$ (10 mL×2) and dried under reduced pressure. To NaH was added a solution of N-(benzotriazol-1-yl-methyl)-α-(methylthio)phenylimine (Katritzky, A. R. et. al., *Tetrahedron*, 1995, 51, 13271) (1.41 g, 5.0 mmol) and 3-penten-1-on (0.84 mL, 8.6 mmol) in THF (20 mL) and DMSO (5 mL). The resulting mixture was stirred at 40° C. for 2 hours, and was quenched by $H_2O$ (30 mL). The whole was extracted with $Et_2O$ (30 mL×2), and the combined organic layers were washed with brine (20 mL), dried over $MgSO_4$ and concentrated in vaciio. The residue was purified by flash chromatography eluting with hexane-ethyl acetate (5:1) to give the less polar product (0.58 g, 58% yield) as a solid and the polar product (0.22 g, 22% yield) as a white solid.

3-Acetyl-4-methyl-2-phenyl-1H-pyrrole (less polar):

mp 156–157° C.; $^1$H-NMR ($CDCl_3$) δ 8.14 (br. s, 1H), 7.41 (s, 5H), 6.59–6.56 (m, 1H), 2.30 (d, J=1.1 Hz, 3H), 2.09 (s, 3H); MS (EI) m/z 199 (M$^+$); Anal. Calcd for $C_{13}H_{13}NO$: C, 78.36; H, 6.58; N, 7.03. Found: C, 78.47; H, 6.57; N, 7.12.

3-Acetyl-4-methyl-5-phenyl-1H-pyrrole (polar):

mp 156–157° C.; 1H-NMR ($CDCl_3$) δ 8.43 (br. s, 1H), 7.47–7.37 (m, 5H), 7.36–7.27 (m, 1H), 2.45 (s, 3H), 2.44 (s, 3H); MS (EI) m/z 199 (M$^+$); Anal. Calcd for $C_{13}H_{13}NO$: C, 78.36; H, 6.58; N, 7.03. Found: C, 78.36; H, 6.56; N, 6.96.

3-Acetyl-5-bromo-4-methyl-2-phenyl-1H-pyrrole (Step 2)

The subtitle compound was prepared according to the procedure of Example 45 (Method C) using 3-acetyl-4-methyl-2-phenyl-1H-pyrrole instead of 3-acetyl-2,4-dimethyl-1H-pyrrole in step 1.

mp 158–159° C.;

$^1$H-NMR ($CDCl_3$) δ 8.15 (s, 1H), 7.50–7.35 (m, 5H), 2.24 (s, 3H), 2.06 (s, 3H)MS; (EI) m/z 279 (M$^+$), 277 (M$^+$).

3-Acetyl-4-methyl-2-phenyl-5-(4-pyridyl)-1H-pyrrole (Step 3)

To a stirred suspension of 4-acetyl-2-bromo-3-methyl-5-phenyl-1H-pyrrole (139 mg, 0.50 mmol), 4-pyridylboronic acid (307 mg, 2.5 mmol) in DME (1.5 mL) and saturated aqueous $NaHCO_3$ (0.50 mL) was added $Pd(PPh_3)_2Cl_2$ (70 mg, 0.10 mmol) under nitrogen. The mixture was heated under reflux for 12 hours. After cooling, the mixture was diluted with ethyl acetate (5 mL) and water (10 mL). The organic layer was separated, and then the aqueous layer was extracted with ethyl acetate (5 mL×2). The combined organic layers were extracted with 1M aqueous HCl (3 mL×2). The combined aqueous layes were neutralized by the addition of 10% aqueous KOH until being pH=8. The whole was extracted with $CH_2Cl_2$ (10 mL×3), the combined organic layers were dried over $MgSO_4$, and concentrated in vacuo. The residue was purified by flash chromatography eluting with hexane-ethyl acetate (1:2→EtOAc only) to provide the title product (42 mg, 30% yield) as a colorless solid.

mp 202–203° C.; IR (nujol) 1670, 1650, 1600, 720 cm$^{-1}$; $^1$H-NMR ($CDCl_3$) δ 8.59 (dd, J=4.6, 1.7 Hz, 3H), 7.47 (s, 5H), 7.35 (dd, J=4.6, 1.7 Hz, 2H), 2.47 (s, 3H), 2.11 (s, 3H); MS (EI) m/z 276 (M$^+$); Anal. Calcd for $C_{18}H_{16}N_2O$: C, 78.24; H, 5.84; N, 10.14. Found: C, 78.21; H, 5.75; N, 9.96.

Example 47

3-Acetyl-4-methyl-5-phenyl-2-(4-pyridyl)-1H-pyrrole

The title compound was prepared according to the procedure of Example 46 using 3-acetyl-4-methyl-5-phenyl-1H-pyrrole instead of 3-acetyl-4-methyl-2-phenyl-1H-pyrrole in step 2.

mp 208–209° C.; IR (KBr) 3100, 1730, 1700, 1680, 1450, 1420, 1350, 990, 970, 825, 760, 700 cm$^{-1}$; $^1$H-NMR ($CDCl_3$) δ 8.62 (br. s, 3H), 7.55–7.30 (m, 7H), 2.37 (s, 3H), 2.31 (s, 3H).; MS (EI) m/z 276 (M$^+$); Anal. Calcd for $C_{18}H_{16}N_2O$: C, 78.24; H, 5.84; N, 10.14. Found: C, 78.06; H, 5.80; N, 10.01.

Example 48

3-Acetyl-4-methyl-5-(4-pyridyl)-1H-pyrrole

3-Acetyl-4-methyl-5-bromo-1H-pyrrole (Step 1)

The subtitle compound was prepared according to the procedure of Example 45 (Method C) using 3-acetyl-4-methyl-1H-pyrrole instead of 3-acetyl-2,4-dimethyl-1H-pyrrole in step 1.

$^1$H-NMR ($CDCl_3$) δ 8.46 (br. s, 1H), 7.35 (d, J=3.3 Hz, 1H), 2.39 (s, 3H), 2.26 (s, 3H).

3-Acetyl-4-methyl-5-(4-pyridyl)-1H-pyrrole (Step 2)

The title compound was prepared according to the procedure of Example 45 (Method C) using 3-acetyl-4-methyl-5-bromo-1H-pyrrole instead of 3-acetyl-5-bromo-2,4-dimethyl-1H-pyrrole in step 2.

mp: 210–211° C.; IR (KBr) ν 1650, 1600, 1490, 1400, 1360, 1200, 1000, 820, 720 cm$^{-1}$; $^1$H-NMR (DMSO-d$_6$) δ 11.86 (br. s, 1H), 8.57 (d, J=5.9 Hz, 2H), 7.81 (s, 1H), 7.46 (d, J=5.9 Hz, 2H), 2.43 (s, 3H), 2.36 (s, 3H); Anal. Calcd. for $C_{12}H_{12}N_2O$ 0.1$H_2O$: C, 71.34; H, 6.09; N, 13.87. Found: C, 71.16; H, 6.07 ; N, 13.54.

Example 49

3-Methyl-4-oxo-2-(4-pyridyl)-4,5,6,7-tetrahydro-1H-indole

3-Methyl-4-oxo-4,5,6,7-tetrahydro-1H-indole (Step 1)

The subtitle compound was prepared according to the literature procedure (Hauptmann, S. et al., *Z. Chem.*, 1966, 3, 107. Ravina, E. et al., *Bio. Med. Chem. Lett.*, 1995, 5, 579.). A mixture of anti-pyruvic aldehyde 1-oxime (1.3 g, 15 mmol), 1,3-cyclohexanedione (1.7 g, 15 mmol), glacial acetic acid (12 mL) and water (3.0 mL) was stirred vigorously at room temperature. Zinc dust (3 g) was added slowly keeping the temperature below 60° C. After addition, this resulting brown solution was heated under reflux temperature for 2 hours. After cooling, the reaction mixture was basified by an addition of 1 M aqueous KOH. The whole was extracted with $CH_2Cl_2$ (50 mL×3), and the combined organic layers were dried over $MgSO_4$, and concentrated in vaciio. The residue was purified by flash chromatography eluting with hexane-ethyl acetate (3:1→EtOAc only) to afford the subtitle compound (1.0 g, 46% yield) of as a yellow solid.

¹H-NMR (CDCl₃) δ 8.40 (br. s, 1H), 6.40 (s, 1H), 2.78 (t, J=6.3 Hz, 2H), 2.45 (t, J=6.5 Hz, 2H), 2.29 (d, J=1.1 Hz, 3H), 2.17–2.07 (m, 2H).

2-Bromo-3-methyl-4-oxo-4,5,6,7-tetrahydro-1H-indole (Step 2)

The subtitle compound was prepared according to the procedure of Example 45 (Method C) using 3-methyl-4-oxo-4,5,6,7-tetrahydro-1H-indole instead of 3-acetyl-2,4-dimethyl-1H-pyrrole in step 1. ¹H-NMR (CDCl₃) δ 8.19 (br. s, 1H), 2.75 (t, J=6.2 Hz, 2H), 2.45 (t, J=6.4 Hz, 2H), 2.23 (s, 3H), 2.17–2.07 (m, 2H); MS (EI) m/z 229 (M), 227 (M⁺);

3-Methyl-4-oxo-2-(4-pyridyl)-4,5,6,7-tetrahydro-1H-indole (Step 3)

The title compound was prepared according to the procedure of Example 45 (Method C) using 2-bromo-3-methyl-4-oxo-4,5,6,7-tetrahydro-1H-indole instead of 3-acetyl-5-bromo-2,4-dimethyl-1H-pyrrole in step 2.

mp 248–249° C.; ¹H-NMR (CDCl₃) δ 9.58 (br. s, 1H), 8.56 (dd, J=4.6, 1.6 Hz, 2H), 7.35 (dd, J=4.6, 1.6 Hz, 2H), 2.88 (t,J=6.2 Hz, 2H), 2.55 (s, 3H), 2.50 (t,J=6.4 Hz, 2H), 2.21–2.11 (m, 2H); MS (EI) m/z 227, 226 (M⁺); Anal. Calcd. for $C_{14}H_{14}N_2O$ 0.7H₂O: C, 70.39; H, 6.20; N, 11.73. Found: C, 70.45; H, 6.12;N, 11.64.

Example 50

3-Acetyl-2-bromo-4-methyl-5-(4-pyridyl)-1IH-pyrrole

The title compound was prepared according to the procedure of Example 45 (Method C) using 3-acetyl-4-methyl-5-(4-pyridyl)-1H-pyrrole instead of 3-acetyl-2,4-dimethyl-1H-pyrrole in step 1.

mp 205–206° C.; ¹H-NMR (CDCl₃) δ 8.51(br. s, 3H), 7.34 (d, J=5.9 Hz, 2H), 2.62 (s, 3H), 2.45 (s, 3H); MS (EI) m/z 280 (M⁺), 278 (M⁺).

Example 51

3-Acetyl-2-(4-fluorophenyl)4-methyl-5-(4-pyridyl)-1H-pyrrole

The title compound was prepared from 3-acetyl-2-bromo-4-methyl-5-(4-pyridyl)-1H-pyrrole according to the procedure of Example 46 using 4-fluorophenylboronic acid instead of 4-pyridylboronic acid in step 3.

mp 202–203° C.; IR (KBr) v 2860, 2760, 1650, 1600, 1495, 1460, 1430, 1225, 1100, 840, 830 cm⁻¹; ¹H-NMR (CDCl₃) δ 8.60 (br. s, 1H), 8.59 (d, J=6.2 Hz, 2H), 7.45 (dd, J=8.4, 5.1 Hz, 2H), 7.34 (dd, J=5.1, 1.3 Hz, 2H), 7.17 (t, J=8.4 Hz, 2H), 2.46 (s, 3H), 2.11 (s, 3H); MS (EI) m/z 294 (M⁺); Anal. Calcd for $C_{18}H_{15}N_2OF$ 0.3 H₂O: C, 72.13; H, 5.25; N, 9.35. Found: C, 72.05; H, 5.27; N, 9.05.

Example 52

3-Acetyl-4-methyl-5-(4-pyridyl)-2-(2-thienyl)-1H-pyrrole

The title compound was prepared from 3-acetyl-2-bromo-4-methyl-5-(4-pyridyl)-1H-pyrrole according to the procedure of Example 46 using 2-thienylboronic acid instead of 4-pyridylboronic acid in step 3.

mp 231–232° C.; IR (KBr) 3200, 1650, 1600, 1430, 1350, 1220, 1000, 820, 700 cm⁻¹; ¹H-NMR (CDCl₃) δ 8.65–8.57 (m, 2H), 8.50 (br. s, 1H), 7.46 (dd, J=5.1, 1.1 Hz, 1H), 7.34 (dd, J=4.4, 1.8 Hz, 2H), 7.25 (d, J=1.1 Hz, 1H), 7.14 (dd, J=5.1, 3.7 Hz, 1H), 2.45 (s, 3H), 2.25 (s, 3H); MS (EI) m/l 284, 283, 282 (M⁺); Anal. Calcd. for $C_{16}H_{14}N_2OS$: C, 68.06; H, 5.00; N, 9.92. Found: C, 67.74; H, 5.00; N, 9.68.

Example 53

4-Oxo-3-phenyl-1-(4-pyridyl)-4,5,6,7-tetrahydroisoindole

7-Oxo-1-phenyl-4,5,6,7-tetrahydroisoindole and 4-Oxo-1-phenyl-4,5,6,7-tetrahydroisoindole (Step 1)

NaH (60% oil dispersion; 420 mg, 10.5 mmol) was washed with Et₂O (2×15 mL) and dried under reduced pressure. To NaH was added a solution of N-(benzotriazole-1-ylmethyl)-α-(methylthio)phenylimine (988 mg, 3.5 mmol) and 2-cyclohexen-1-one (0.41 mL, 4.3 mmol) in THF (12 mL) and DMSO (3 mL) at 0° C. under N₂. The reaction mixture was stirred at 40° C. for 2 hours, and was quenched by water (15 mL). The whole was extracted with Et₂O (2×15 mL) and ethyl acetate (15 mL), and the combined organic layers were washed with brine (15 mL), dried over MgSO₄ and filtered. The filtrate was concentrated and the residue (isomeric ratio=ca 6.6:1) was purified by flash chromatography eluting with hexane-ethyl acetate (5:1→2:1) to afford the less polar product (85 mg, 11% yield) and the polar product (541 mg, 73% yield).

7-Oxo-1-phenyl-4,5,6,7-tetrahydroisoindole (less polar):
¹H-NMR (CDCl₃) δ 8.44 (br. s, 1H), 7.76 (dd, J=8.5, 1.9 Hz, 2H), 7.45–7.29 (m, 3H), 6.61 (t, J=1.1 Hz, 1H), 2.76 (t, J=6.3 Hz, 2H), 2.53 (t, J=6.5 Hz, 2H), 2.13–2.04 (m, 2H); MS (EI) m/z 221 (M⁺);

4-Oxo-1-phenyl-4,5,6,7-tetrahydroisoindole (polar):
¹H-NMR (CDCl₃) δ 9.18 (br. s, 1H), 7.50–7.37 (m, 5H), 7.33–7.23 (m, 1H), 2.89 (t, J=5.9 Hz, 2H), 2.53 (dd, J=7.2, 5.7 Hz, 2H), 2.14–2.04 (m, 2H); MS (EI) m/z 221 (M⁺);

1-Bromo-4-oxo-3-phenyl-4,5,6,7-tetrahydroisoindole

The subtitle compound was prepared according to the procedure of Example 45 (Method C) using 7-oxo-1-phenyl-4,5,6,7-tetrahydroisoindole instead of 3-acetyl-2,4-dimethyl-1H-pyrrole in step 1.

¹H-NMR (CDCl₃) δ 8.38 (br. s, 1H), 7.72 (dd, J=7.7, 1.5 Hz, 2H), 7.47–7.32 (m, 3H), 2.64 (t, J=6.2 Hz, 2H), 2.52 (t, J=6.5 Hz, 2H), 2.13–2.03 (m, 2H); MS (EI) m/z 291 (M⁺), 289 (M⁺).

4-Oxo-3-phenyl-1-(4-pyriddy)-4,5,6,7-tetrahydroisoindole

The title compound was prepared according to the procedure of Example 45 (Method C) using 1-bromo-4-oxo-3-phenyl-4,5,6,7-tetrahydroisoindole instead of 3-acetyl-5-bromo-2,4-dimethyl-1H-pyrrole in step 2.

mp 259–260° C.; ¹H-NMR (CDCl₃) δ 8.75 (br. s, 1H), 8.63 (d, J=6.2 Hz, 2H), 7.81–7.76 (m, 2H), 7.49–7.37 (m, 3H), 7.33 (dd, J=4.6, 1.6 Hz, 2H), 3.00 (t, J=6.0 Hz, 2H), 2.59 (t, J=6.4 Hz, 2H), 2.20–2.10 (m, 2H); MS (EI) m/z 288 (M⁺);

Example 54

7-Oxo-3-phenyl-1-(4-pyridyl)-4,5,6,7-tetrahydroisoindole

1-Bromo-7-Oxo-3-phenyl-4,5,6,7-tetrahydroisoindole

The subtitle compound was prepared according to the procedure of Example 45 (Method C) using 4-oxo-1-phenyl-4,5,6,7-tetrahydroisoindole instead of 3-acetyl-2,4-dimethyl-1H-pyrrole in step 1.

¹H-NMR (CDCl₃) δ 8.95 (br. s, 1H), 7.47–7.26 (m, 5H), 2.88 (t, J=6.1 Hz, 2H), 2.54 (t, J=6.4 Hz, 2H), 2.12–2.02 (m, 2H); MS (EI) m/z 291 (M), 289 (M⁺);

7-Oxo-3-phenyl-1-(4-pyridyl)-4,5,6,7-tetrahydroisoindole

The title compound was prepared according to the procedure of Example 45 (Method C) using 1-bromo-7-oxo-3- phenyl-4,5,6,7-tetrahydroisoindole instead of 3-acetyl-5-bromo-2,4-dimethyl-1H-pyrrole in step 2.

mp 254–255° C.; IR (KBr) 2950, 1660, 1600, 1585, 1450, 1000, 820, 720, 700 cm$^{-1}$; $^1$H-NMR (CDCl$_3$) δ 8.91 (br. s, 1H), 8.68–8.60 (m, 2H), 7.76 (dd, J=4.6, 1.6 Hz, 2H), 7.48 (d, J=4.4 Hz, 2H), 7.42–7.30 (m, 1H), 2.94 (t, J=6.2 Hz, 2H), 2.61 (t, J=6.4 Hz, 2H), 2.17–2.07 (m, 2H); MS (EI) m/z 288 (M$^+$); Anal. Calcd for C$_{19}$H$_{16}$N$_2$O 0.1H$_2$O: C, 78.65; H, 5.63; N, 9.65. Found: C, 78.40; H, 5.50; N, 9.55.

Example 55

4-Oxo-2-(4-pyridyl)-3,6,6-trimethyl-4,5,6,7-tetrahydro-1H-indole

The title compound was prepared according to the procedure of Example 49 using 2,2-dimethyl-1,3-cyclohexanedione instead of 1,3-cyclohexanedione in step 1.

mp: 241–241.5° C.; IR (KBr) 2950, 1660, 1605, 1480, 1375, 1000, 825 cm$^{-1}$;. $^1$H-NMR (CDCl$_3$) δ 8.61 (dd, J=4.6, 1.7 Hz, 2H), 8.44 (br. s, 1H), 7.31 (dd, J=4.6 Hz, 1.7 Hz, 2H), 2.71 (s, 2H), 2.55 (s, 3H), 2.37 (s, 2H), 1.15 (s, 6H); MS (EI) 254(M$^+$); Anal. Calcd for C$_{16}$H$_{18}$N$_2$O: C, 75.56; H, 7.13; N, 11.01. Found: C, 75.19, H, 7.21; N, 10.86.

Example 56

3-Methyl-4-oxo-6-phenyl-2-(4-pyridyl)-4,5,6,7-tetrahydro-1H-indole

The title compound was prepared according to the procedure of Example 49 using 2-phenyl-1,3-cyclohexanedione instead of 1,3-cyclohexanedione in step 1.

mp: 256–257° C.; IR (KBr) 3220, 1620, 1600, 1485, 1440, 1410, 1380, 1070, 820, 760, 700 cm$^{-1}$. $^1$H-NMR (CDCl$_3$) δ 8.61 (d, J=6.2 Hz, 2H), 7.35–7.25 (m, 7H), 3.62–3.49 (m, 1H), 3.15–3.06 (m, 2H), 2.80–2.76 (m, 2H), 2.60 (s, 3H); MS (EI) 302 (M$^+$); Anal. Calcd for C$_{20}$H$_{18}$N$_2$O 0.2H$_2$O: C, 78.97; H, 6.03; N, 9.21. Found: C, 79.00, H, 5.99; N, 9.12.

Example 57

3-Cyano-4-methyl-2,5-di(4-pyridyl-1H-pyrrole

The titled compound was prepared according to the procedure of Example 1 using β-aminocrotononitrile instead of 2,4-pentanedione.

mp: 270–275° C. (Recryst. from ethyl acetate-EtOH); IR (KBr) ν 2200, 1610, 1590, 14430, 1320, 1220, 1000, 820, 770, 680, 520 cm$^{-1}$; $^1$H-NMR (DMSO-d$_6$) δ 12.52 (br. s, 1H), 8.73 (dd, J=4.8 Hz, 1.8 Hz, 2H), 8.68 (dd, J=4.4 Hz, 1.5 Hz, 2H), 7.85(dd,J=4.8 Hz, 1.5 Hz, 2H), 7.64 (dd, J=4.4 Hz, 1.5 Hz, 2H), 2.37 (s, 3H); Anal. Calcd. for C$_{16}$H$_{12}$N$_4$ 1.0H$_2$O: C, 69.05; H, 5.07; N, 20.13. Found: C, 68.71; H, 4.98; N, 20.07.

The compounds of example 58–74 were prepared according to the procedure of example 46 using the corresponding boronic acids or tin reagents instead of 4-pyridineboronic acid in step 3.

Example 58

3-Acetyl-2-(3-aminophenyl)-4-methyl-5-(4-pyridyl)-1H-pyrrole mp 193–195° C.; $^1$H-NMR (CDCl$_3$) δ 8.61(dd, J=4.8 Hz, 1.9 Hz, 2H), 8.42 (bs, 1H), 7.34 (dd, J=4.8 Hz, 1.9 Hz, 2H), 7.28–7.21 (m, 1H), 6.84 (d, J=7.7 Hz, 1H), 6.77–6.74 (m, 2H), 3.81 (br. s, 2H), 2.45 (s, 3H), 2.17 (s, 3H); MS (FAB) m/z 292 (M+H)$^+$; Anal. Calcd. for C$_{18}$H$_{17}$N$_3$O 0.4H$_2$O: C, 72.41; H, 6.01; N, 14.07. Found: C, 72.50; H, 5.83; N, 13.92.

Example 59

3-Acetyl-4-methyl-2-(2-naphthyl)-5-(4-pyridyl)-1H-pyrrole mp 116–123° C.; $^1$H-NMR (CDCl$_3$) δ 8.78 (br.s, 1H), 8.61–8.57 (m, 2H), 7.95–7.84 (m, 4H), 7.60–7.53 (m, 3H), 7.39–7.35 (m, 2H), 2.47 (s, 3H), 2.13 (s, 3H); MS (FAB) m/z 327 (M+H)$^+$; Anal. Calcd. for C$_{22}$H$_{18}$N$_2$O 0.2H$_2$O: C, 80.07; H, 5.62; N, 8.49. Found: C, 80.23; H, 5.67; N, 8.25.

Example 60

3-Acetyl-2-(4-formylphenyl)-4-methyl-5-(4-pyridyl)-1H-pyrrole mp 97–100° C.; $^1$H-NMR (CDCl$_3$) δ 10.06 (s, 1H), 9.21 (br.s, 1H), 8.58(d, J=5.9 Hz, 2H), 7.96 (d, J=8.0 Hz, 2H), 7.66 (d, J=8.0 Hz, 2H), 7.38 (d, J=5.9 Hz, 2H), 2.44 (s, 3H), 2.21 (s, 3H); MS (EI) m/z 304 (M$^+$);

Eample 61

3-Acetyl-4-methyl-2-(1-naphthyl)-5-(4-pyridyl)-1H-pyrrole mp 218–220° C.; $^1$H-NMR (CDCl$_3$) δ 8.69 (s, 1H), 8.57 (d, J=6.2 Hz, 2H), 8.00–7.92 (m, 2H), 7.78–7.68 (m, 1H), 7.60–7.48 (m, 3H), 7.42–7.33 (m, 3H), 2.58 (s, 3H), 1.77 (s, 3H); MS (EI) m/z 326 (M)$^+$.

Eample 62

3-Acetyl-2-{3-(4-fluorophenoxy)phenyl}-4-methyl-5-(4-pyridyl)-1H-pyrrole mp 158–159° C.; $^1$H-NMR (CDCl$_3$) δ 8.63–8.60 (m, 2H), 8.43 (br.s, 1H), 7.45–7.38 (m, 1H), 7.34–7.32 (m, 2H), 7.20–7.17 (m, 1H), 7.07–7.02 (m, 6H), 2.44 (s, 3H), 2.16 (s, 3H); MS (FAB) m/z 387 (M+H)$^+$; Anal. Calcd. for C$_{24}$H$_{19}$N$_2$O$_2$F 0.1H$_2$O: C, 74.25; H, 4.98; N, 7.22. Found: C, 74.44; H, 4.92; N, 6.84.

Example 63

3-Acetyl-2-{(4-methoxycarbonyl)phenyl}-4-methyl-5-(4-pyridyl)-1H-pyrrole mp 187–189° C.; $^1$H-NMR (CDCl$_3$) δ 9.25 (br.s, 1H), 8.54 (d, J=4.8 Hz, 2H), 8.09 (d, J=8.1 Hz, 2H), 7.54 (d, J=8.1 Hz, 2H), 7.37 (d, J=4.8 Hz, 2H), 3.93 (s, 3H), 2.43 (s, 3H), 2.15 (s, 3H); MS (FAB) m/z 335 (M+H)$^+$; Anal. Calcd. for C$_{20}$H$_{18}$N$_2$O$_3$ 0.2H$_2$O: C, 71.08; H, 5.49; N, 8.29. Found: C, 71.25; H, 5.45; N, 8.03.

Example 64

3-Acetyl-4-methyl-2-(3-nitrophenyl)-5-(4-pyridyl)-1H-pyrrole mp 214–217° C.; $^1$H-NMR (CDCl$_3$) δ 9.35 (br.s, 1H), 8.57 (d, J=5.1 Hz, 2H), 8.37 (t, J=1.9 Hz, 1H), 8.28–8.24 (m, 1H), 7.85–7.80 (m, 1H), 7.62 (t, J=8.1 Hz, 1H), 7.39–7.35 (m, 2H), 2.44 (s, 3H), 2.25 (s, 3H); MS (FAB) m/z 335 (M+H)$^+$; Anal. Calcd. for C$_{18}$H$_{15}$N$_3$O$_3$ H$_2$O: C, 63.71; H, 5.05; N, 12.38. Found: C, 63.46; H, 4.56; N, 12.00.

Example 65

3-Acetyl-4-methyl-2-(3-pyridyl)-5-(4-pyridyl)-1H-pyrrole mp 182–186° C.; $^1$H-NMR (CDCl$_3$) δ 9.77 (br.s, 1H), 8.73–8.70 (m, 1H), 8.60–8.54 (m, 3H), 7.86–7.81 (m, 1H), 7.40–7.34 (m, 3H), 2.47 (s, 3H), 2.18 (s, 3H); MS (FAB) m/z 278 (M+H)$^+$; Anal. Calcd. for $C_{17}H_{15}N_3O$ 0.8H$_2$O: C, 69.99; H, 5.74; N, 14.40. Found: C, 69.82; H, 5.28; N, 14.22.

Example 66

3-Acetyl-2-(3-chloro-4-fluorophenyl)-4-methyl-5-(4-pyridyl)-1H-pyrrole mp 206–209° C.; $^1$H-NMR (CDCl$_3$) δ 9.43 (br.s, 1H), 8.50 (br.d, J=6.2 Hz, 2H), 7.55 (dd, J=6.9 Hz, 2.2 Hz, 1H), 7.37–7.32 (m, 3H), 7.21 (t, J=8.8 Hz, 1H), 2.43 (s, 3H), 2.16 (s, 3H); MS (ESI) m/z 328 (M+H)$^+$; Anal. Calcd. for $C_{18}H_{14}N_2OClF$: C, 65.76; H, 4.29; N, 8.52. Found: C, 66.16; H, 4.40; N, 8.26.

Example 67

3-Acetyl-4-methyl-5-(4-pyridyl)-2-vinyl-1H-pyrrole mp 150–155° C.; $^1$H-NMR (CDCl$_3$) δ 8.64 (dd, J=4.7 Hz, 1.8 Hz, 2H), 8.65–8.60 (br.s, 1H), 7.32 (dd, J=4.7 Hz, 1.8 Hz, 2H), 7.20 (dd. J=17.5 Hz, 11.4 Hz, 1H), 5.57 (d, J=17.5 Hz, 1H), 5.38 (d, J=11.4 Hz, 1H), 2.52 (s, 3H), 2.43 (s, 3H); MS (EI) m/z 226 (M$^+$).

Example 68

3-Acetyl-2-(4-chlorophenyl)-4-methyl-5-(4-pyridyl)-1H-pyrrole mp 187.5–189.5° C.; $^1$H-NMR (CDCl$_3$) δ 8.91 (br.s, 1H), 8.56 (br.d, J=6.2 Hz, 2H), 7.48–7.40 (m, 4H), 7.35 (br.d, J=6.2 Hz, 2H), 2.44 (s, 3H), 2.14 (s, 3H); MS (ESI) m/z 309 (M−H)$^-$; Anal. Calcd. for $C_{18}H_{15}N_2OCl$: C, 69.57; H, 4.86; N, 9.01. Found: C, 69.21; H, 5.01; N, 8.74.

Example 69

3-Acetyl-2-(2-furyl)-4-methyl-5-(4-pyridyl)-1H-pyrrole mp 218–220° C.; $^1$H-NMR (CDCl$_3$) δ 8.95 (br.s, 1H), 8.65 (br.d, J=6.2 Hz, 2H), 7.48 (d, J=1.8 Hz, 1H), 7.37–7.34 (m, 2H), 7.21 (d, J=3.3 Hz, 1H), 6.53 (dd, J=3.3 Hz, 1.8 Hz, 1H), 2.47 (s, 3H), 2.46 (s, 3H); MS (ESI) m/z 267 (M+H)$^+$; Anal. Calcd. for $C_{16}H_{14}N_2O_2$: C, 72.17; H, 5.30; N, 10.52. Found: C, 71.81; H, 5.40; N, 10.44.

Example 70

3-Acetyl-4-methyl-5-(4-pyridyl)-2-(3-thienyl)-1H-pyrrole mp 240–244° C.; $^1$H-NMR (CDCl$_3$) δ 8.94 (s, 1H), 8.55 (br.d, J=6.2 Hz, 2H), 7.49–7.42 (m, 2H), 7.34 (br.d, J=6.2 Hz, 2H), 7.22 (dd, J=5.1 Hz, 1.4 Hz, 1H), 2.46 (s, 3H), 2.18 (s, 3H); MS (ESI) m/z 283 (M+H)$^+$; Anal. Calcd. for $C_{16}H_{14}N_2OS$ 0.1H$_2$O: C, 67.63; H, 5.04; N, 9.86. Found: C, 67.53; H, 4.93; N, 9.59.

Example 71

3-Acetyl-4-methyl-2-(4-methylthiophenyl)-5-(4-pyridyl)-1H-pyrrole mp 169–172° C.; $^1$H-NMR (CDCl$_3$) δ 9.10 (s, 1H), 8.53 (dd, J=4.4 Hz, 1.4 Hz, 2H), 7.40–7.26 (m, 6H), 2.52 (s, 3H), 2.44 (s, 3H), 2.13 (s, 3H); MS (ESI) m/z 323 (M+H)$^+$; Anal. Calcd. for $C_{19}H_{18}N_2OS$ 0.2H$_2$O: C, 70.00; H, 5.69; N, 8.59. Found: C, 69.95; H, 5.83; N, 8.38.

Example 72

3-Acetyl-2-(2-fluorophenyl)-4-methyl-5(4-pyridyl-1H-pyrrole mp 220–222° C.; $^1$H-NMR (CDCl$_3$) δ 8.76 (br.s, 1H), 8.60 (dd, J=4.7 Hz, 1.4 Hz, 2H), 7.48–7.40 (m, 2H), 7.35 (dd, J=4.7 Hz, 1.4 Hz, 2H), 7.29–7.17 (m, 2H), 2.47 (s, 3H), 2.16 (s, 3); MS (ESI) m/z 295 (M+H)$^+$; Anal. Calcd. for $C_{18}H_{15}N_2OF$ 0.2H$_2$O: C, 72.57; H, 5.21; N, 9.40. Found: C, 72.87; H, 5.14; N, 9.47.

Example 73

3-Acetyl-4-methyl-5-(4-pyridyl)-2-(4-trifluoromethylphenyl)-1H-pyrrole mp 178.5–179.5° C.; $^1$H-NMR (CDCl$_3$) δ 9.14 (bs, 1H), 8.57–8.53 (m, 2H), 7.74–7.59 (m, 4H), 7.36 (dd, J=4.6 Hz, 1.7 Hz, 2H), 2.44 (s, 3H), 2.17 (s, 3H); IR (KBr) 3200, 1640, 1600, 1460, 1425, 1320, 1170, 1130, 1070, 1020, 950, 930cm$^{-1}$; MS (EI) m/z 344 (M$^+$); Anal. Calcd for $C_{14}H_{15}N_2OF_3$ 0.2H$_2$O: C, 65.59; H, 4.46; N, 8.05. Found: C, 65.32; H, 4.40; N, 8.08.

Example 74

3-Acetyl-2-(4-methoxyphenyl)-4-methy-5-(4-pyridyl)-1H-pyrrole mp 185–186° C.; $^1$H-NMR (CDCl$_3$) δ 8.61 (dd, J=4.4 Hz, 1.8 Hz, 2H), 8.40 (bs, 1H), 7.39 (dd, J=6.6 Hz, 2.2 Hz, 2H), 7.35 (dd, J=4.6, 1.7 Hz, 2H), 6.99 (dd, J=6.8, 2.0 Hz, 2H), 3.87 (s, 3H), 2.47 (s, 3H), 2.11 (s, 3H); IR (KBr) 3200, 1600, 1490, 1460, 1420, 1405, 1280, 1250, 1180, 1040, 840, 820 cm$^{-1}$; MS (EI) m/z 306 (M$^+$); Anal. Calcd for $C_{19}H_{18}N_2O_2$ 0.3H$_2$O: C, 73.20; H, 6.01; N, 8.99. Found: C, 73.18; H, 5.79; N, 8.93.

Example 75

3-Acetyl-4-methyl-2-(4-methylsulfinylphenyl)-5-(4-pyridyl)-1H-pyrrole

To a stirred solution of 3-acetyl-4-methyl-2-(4-methylthiophenyl)-5-(4-pyridyl)-1H-pyrrole (0.24 g, 0.74 mmol) in methanol (8 mL) was added a solution of NaIO$_4$ (0.6 g) in water (16 mL) at room temperature. After stirring for 15 hours, the precipitates were collected by filtration. The filtrate was extracted with CH$_2$Cl$_2$—EtOH (10:1, 50 mL×2), dried over MgSO$_4$, and concentrated ini vacuo. The solids were purified by flash chromatography eluting with CH$_2$Cl$_2$—EtOH (10:1) to provide the title compound (0.24 g, quantitative yield).

mp 249–250° C.; $^1$H-NMR (CDCl$_3$) δ 10.8 (s, 1H), 8.56 (d, J=5.9 Hz, 2H), 7.60 (d, J=8.1 Hz, 2H), 7.50–7.45 (m, 4H), 2.69 (s, 3H), 2.47 (s, 3H), 2.18 (s, 3H); MS (ESI) m/z 339 (M+H)$^+$; Anal. Calcd. for $C_{19}H_{18}N_2O_2S$ 0.2H$_2$O: C, 66.72; H, 5.42; N, 8.19. Found: C, 66.52; H, 5.64; N, 8.10.

Example 76

3-Acetyl-4-methyl-2-(4-morpholino)-5-(4-pyridyl)-1H-pyrrole

A mixture of 3-acetyl-2-bromo4-methyl-5-(4-pyridyl)-1H-pyrrole (1.6 g, 5.74 mmol) and morpholine (12 mL) was heated at 135° C. for 12 hours. After cooling down, the precipitates were collected by filtration. The filtrate was purified by flash chromatography eluting with CH$_2$Cl$_2$—

EtOH (10:1) to provide 0.72 g of yellow solids. Recrystallization from ethyl acetate-EtOH provided the title compound (0.65 g, 40% yield).

mp 218–220° C.; $^1$H-NMR (CDCl$_3$) δ 8.57 (br.s, 1H), 8.53 (d, J=5.9 Hz, 2H), 7.26–7.23 (m, 2H), 3.89 (t, J=4.4Hz, 4H), 3.18 (t, J=4.4 Hz, 4H), 2.55 (s, 3H); 2.42 (s, 3H); MS (FAB) m/z 286 (M+H)$^+$; Anal. Calcd. for C$_{16}$H$_{19}$N$_3$O$_2$: C, 67.35; H, 6.71; N, 14.73. Found: C, 67.27; H, 7.07; N, 14.77.

The compounds of example 77–81 were prepared according to the procedure of example 76 using the corresponding cyclic amines instead of morpholine.

Example 77

3-Acetyl-4-methyl-2-(1-piperidinyl -5-(4-pyridyl-1H-pyrrole mp 204–207° C.; $^1$H-NMR (CDCl$_3$) δ 8.55–8.52 (m, 2H), 8.23 (br.s, 1H), 7.25–7.22 (m, 2H), 3.11 (t, J=5.1 Hz, 4H), 2.54 (s, 3H), 2.41 (s, 3H), 1.77–1.61 (m, 6H); MS (FAB) m/z 284 (M+H)$^+$; Anal. Calcd. for C$_{17}$H$_{21}$N$_3$O 0.2H$_2$O: C, 71.15; H, 7.52; N, 14.64. Found: C, 71.23; H, 7.61;N, 14.36.

Example 78

3-Acetyl-4-methyl-2-(4-phenylpiperazin-1-yl)-5-(4-pyridyl)-1H-pyrrole mp 218–220° C.; $^1$H-NMR (CDCl$_3$) δ 8.57–8.53 (m, 2H), 8.46 (br.s, 1H), 7.33–7.24 (m, 4H), 6.99–6.89 (m, 3H), 3.50–3.34 (m, 8H), 2.57 (s, 3H), 2.43 (s, 3H); MS (FAB) m/z 361 (M+H)$^+$; Anal. Calcd. for C$_{22}$H$_{24}$N$_4$O 0.2H$_2$O: C, 72.58; H, 6.76; N, 15.39. Found: C, 72.52; H, 6.86;N, 15.15.

Example 79

3-Acetyl-2-{(1,4-dioxa-8-azaspiro[4.5]-decan)-8-yl}-4-methyl-5-(4-pyridyl)-1H-pyrrole mp 200–203° C.; $^1$H-NMR (CDCl$_3$) δ 8.55 (d, J=6.3 Hz, 2H), 8.25 (br.s, 1H), 7.23 (d, J=6.3 Hz, 2H), 4.00 (s, 4H), 3.25 (t, J=5.1 Hz, 4H), 2.55 (s, 3H), 2.42 (s, 3H), 1.92 (t, J=5.1 Hz, 4H); MS (FAB) m/z 342 (M+H)$^+$; Anal. Calcd. for C$_{19}$H$_{23}$N$_3$O$_3$ 0.4H$_2$O: C, 65.46; H, 6.88; N, 12.05. Found: C, 65.32; H, 6.73; N, 12.30.

Example 80

3-Acetyl-2-(cis-2,6-dimethylmorpholin-4-yl)-4-methyl-5-(4-pyridyl)-1H-pyrrole mp 95–100° C.; $^1$H-NMR (CDCl$_3$) δ 9.42 (br.s, 1H), 8.43 (d, J=5.8 Hz, 2H), 7.28–7.24 (m, 2H), 3.92–3.83 (m, 2H), 3.24 (br.s, 1H), 3.20 (br.s, 1H), 2.72–2.62 (m, 2H), 2.53 (s, 3H), 2.41 (s, 3H), 1.20 (d, J=6.3 Hz, 6H); MS (EI) m/z 313 (M$^+$);

Example 81

3-Acetyl-4-methyl-5-(4-pyridyl)-2-{4-(2-pyridyl) piperazin-1-yl}-1H-pyrrole mp 89–92° C.; $^1$H-NMR (CDCl$_3$) δ 8.75 (br.s, 1H), 8.51 (d, J=5.1 Hz, 2H), 8.22 (d, J=4.0 Hz, 1H), 7.52 (t, J=8.1 Hz, 1H), 7.24 (d, J=5.1 Hz, 2H), 6.71–6.66 (m, 2H), 3.75–3.72 (m, 4H), 3.31–3.27 (m, 4H), 2.58 (s, 3H), 2.42 (s, 3H); MS (ESI) m/z 362 (M+H)$^+$; Anal. Calcd. for C$_{21}$H$_{23}$N$_5$O 0.1H$_2$O: C, 69.44; H, 6.44; N, 19.28. Found: C, 69.14; H. 6.57; N, 18.98.

Example 82

4-Oxo-2-(4-pyridyl)-3,5,5trimethyl-4,5,6,7-tetrahydro-1H-indole and 4-Oxo-2-(4-pyridyl)-3,7,7-trimethyl-4,5,6,7-tetrahydro-1H-indole 4-Oxo-3,5,5-trimethyl-4,5,6,7-tetrahydro-1H-indole and 4-Oxo-3,7,7-trimethyl-4,5,6,7-tetrahydro-1H-indole The subtitle compounds were prepared according to the procedure of Example 49 using 4,4-dimethylcyclohexane-1,3-dione instead of cyclohexane-1,3-dione in step 1.

4-Oxo-3,5,5-trimethyl-4,5,6,7-tetrahydro-1H-indole $^1$H-NMR (CDCl$_3$) δ 7.92 (br.s, 1H), 6.41 (s, 1H), 2.79 (t, J=6.2 Hz, 2H), 2.29 (d, J=1.1 Hz, 3H), 1.97 (t, J=6.2 Hz, 2H), 1.18 (s, 6H).

4-Oxo-3,7,7-trimethyl-4,5,6,7-tetrahydro-1H-indole $^1$H-NMR (CDCl$_3$) δ 8.10 (br.s, 1H), 6.40 (d, J=1.1 Hz, 1H), 2.54 (t, J=6.2 Hz, 2H), 2.29 (d, J=1.1 Hz, 3H), 1.96 (t, J=6.2 Hz, 2H), 1.34 (s, 6H).

2-Bromo-4-oxo-3,5,5-trimethyl-4,5,6,7-tetrahydro-1H-indole and 2-Bromo-4-oxo-3,7,7-trimethyl-4,5,6,7-tetrahydro-1H-indole The subtitle compounds were prepared ccording to the procedure of Example 45 (Method C) using 4-oxo-3,5,5-trimethyl-4,5,6,7-tetrahydro-1H-indole and 4-oxo-3,7,7-trimethyl-4,5,6,7-tetrahydro-1H-indole instead of 3-acetyl-2,4-dimethyl-1H-pyrrole in step 1.

2-Bromo-4-oxo-3,5,5-trimethyl-4,5,6,7-tetrahydro-1H-indole $^1$H-NMR (CDCl$_3$) δ 8.15 (br.s, 1H), 2.77 (t, J=6.3 Hz, 2H), 2.29 (s, 3H), 1.97 (t, J=6.3 Hz, 2H), 1.17 (s, 6H).

2-Bromo-4-oxo-3,7,7-trimethyl-4,5,6,7-tetrahydro-1H-indole $^1$H-NMR (CDCl$_3$) δ 8.15 (br.s, 1H), 2.54 (t, J=6.3 Hz, 2H), 2.22 (d, J=1.1 Hz, 3H), 1.96 (t, J=6.3 Hz, 2H), 1.34 (s, 6H).

4-Oxo-2-(4-pyridyl)-3,5,5-trimethyl-4,5,6,7-tetrahydro-1H-indole and 4-Oxo-2-(4-pyridyl)-3,7,7-trimethyl-4,5,6,7-tetrahydro-1H-indole The title compounds were prepared according to the procedure of Example 45 (Method C) using 2-bromo-4-oxo-3,5,5-trimethyl-4,5,6,7-tetrahydro- 1H-indole and 2-bromo-4-oxo-3,7,7-trimethyl-4,5,6,7-tetrahydro-1H-indole instead of 3-acetyl-3-bromo-2,4-dimethyl-1H-pyrrole in step 2.

4-Oxo-2-(4-pyridyl)-3,5,5-trimethyl-4,5,6,7-tetrahydro-1H-indole mp 237–239° C.; $^1$H-NMR (CDCl$_3$) δ 8.77 (br.s, 1H), 8.59–8.56 (m, 2H), 7.33–7.30 (m, 2H), 2.89 (t, J=6.2 Hz, 2H), 2.54 (s, 3H), 2.02 (t, J=6.2 Hz, 2H), 1.21 (s, 6H); MS (FAB) m/z 255 (M+H)$^+$; Anal. Calcd. for C$_{16}$H$_{18}$N$_2$O 0.3H$_2$O: C, 73.99; H, 7.22; N, 10.79. Found: C, 74.05; H, 7.15; N, 10.52.

4-Oxo-2-(4-pyridyl)-3,7,7-trimethyl-4,5,6,7-tetrahydro-1H-indole mp 278–280° C.; $^1$H-NMR (CDCl$_3$) δ 8.61–8.58 (m, 2H), 8.49 (br.s, 1H), 7.33–7.28 (m, 2H), 2.58 (t, J=6.2 Hz, 2H), 2.54 (s, 3H), 2.00 (t, J=6.2 Hz, 2H), 1.42 (s, 6H); MS (FAB) m/z 255 (M+H)$^+$; Anal. Calcd. for C$_{16}$H$_{18}$N$_2$O 0.2H$_2$O: C, 74.51; H, 7.19; N, 10.86. Found: C, 74.53; H,7.31;N, 10.63.

Example 83

3-Methyl-4-oxo-2-(4-cyclohepteno(b)pyrrole

The title compounds were prepared according to the procedure of Example 49 using cycloheptane-1,3-dione instead of cyclohexane-1,3-dione in step 1.

3-Methyl-4-oxo-cyclohepteno(b)pyrrole $^1$H-NMR (CDCl$_3$) δ 9.50 (br.s, 1H), 6.35 (s, 1H), 2.90–2.80 (m, 2H), 2.70–2.60 (m, 2H), 2.26 (s, 3H), 1.95–1.85 (m, 4H).

2-Bromo-3-methyl-4-oxo-cyclohepteno(b)pyrrole $^1$H-NMR (CDCl$_3$) δ 8.60 (br.s, 11H), 2.88 (t, J=5.9 Hz, 2H), 2.67 (t, J=5.5 Hz, 2H), 2.21 (s, 3H), 1.90–1.86 (m, 4H).

3-Methyl-4-oxo-2-(4-pyridyl)-cyclohepteno(b)pyrrole mp 205–210° C.; $^1$H-NMR (CDCl$_3$) δ 8.85 (br.s, 1H), 8.57–8.53 (m, 2H), 7.32–7.25 (m, 2H), 3.00–2.95 (m, 2H), 2.73–2.68 (m, 2H), 2.48 (s, 3H), 1.98–1.93 (m, 4H); MS (ESI) m/z 241 (M+H)$^+$; Anal. Calcd. for $C_{15}H_{16}N_2O$ 0.5H$_2$O: C, 72.26; H, 6.87; N, 11.24. Found: C, 71.98; H, 6.46; N, 11.29.

Example 84

3-Acetyl-4-methyl-2-nitro-5-(4-pyridyl)-1H-pyrrole

To a cooled (−10~−20° C.) acetic anhydride (1.2 mL) was added fuming nitric acid (0.13 mL) and sulfuric acid (1 drop). After stirring for 3 minutes, 3-acetyl-4-methyl-5-(4-pyridyl)-1H-pyrrole (0.2 g, 1 mmol) was added to the mixture. The resulting mixture was allowed to warm to room temperature and stirred for additional 1 hour. The mixture was poured into saturated aqueous NaHCO$_3$. The whole was extracted with ethyl acetate (30 mL×4), the combined organic layers washed with brine, dried over MgSO$_4$, and concentrated in vacito. The residue was purified by flash chromatography eluting with ethyl acetate-hexane (2:1) to provide the title compound (35 mg, 14% yield).

mp 187–188° C.; $^1$H-NMR (CDCl$_3$) δ 10.95 (br.s, 1H), 8.67 (d, J=5.9 Hz, 2H), 7.43–7.40 (m, 2H), 2.62 (s, 3H), 2.23 (s, 3H); MS (EI) m/z 245 (M$^+$); Anal. Calcd. for $C_{12}H_{11}N_3O_3$ 0.25H$_2$O: C, 57.71; H, 4.64; N, 16.83. Found: C, 58.23; H, 4.50; N, 16.28.

Example 85

2,4-Dimethyl-3-triflluoroacetiy-5-(4-pyridyl)-1H-pyrrole 2,4-Dimethyl-3-trifluoroacetyl-1H-pyrrole According to the literature procedure (Chiswell, B. *Inorganica Chimica Acta*. 1972, 629), a mixture of anti-pyruvic aldehyde 1-oxime (1.3 g, 15 mmol), 1,1,1-trifluoro-2,4-pentadione (1.85 mL, 15 mmol), glacial acetic acid (12 mL) and H$_2$O (3.0 mL) was stirred vigorously at room temperature. To this flask, zinc dust (3 g) was added slowly keeping the temperature below 60° C. After addition, the resulting brown solution was heated under reflux condition for 2 hours. After cooling down to room temperature, the reaction mixture was basified by an addition of 2 M aqueous NaOH, then filtered. The filtrate was extracted with CH$_2$Cl$_2$ (20 mL×3), the combined organic layer dried over MgSO$_4$, and concentrated iii vacito. The residue was purified by flash chromatography (1–3:1 CH$_2$Cl$_2$-Hexane) to afford the subtitle compound (0.42 g, 15% yield) as an oil.

$^1$H-NMR (CDCl$_3$) δ 8.15 (br. s, 1H), 6.41 (q, J=1.1 Hz, 1H), 2.52 (s, 3H), 2.23 (t, J=1.1Hz, 3H); MS (EI) m/z 191 (M$^+$);

2-Bromo-3,5-dimethyl-4-trifluoroacetyl-1H-pyrrole

The subtitle compound was prepared acording to the procedure of Example 45 (Method C) using 2,4-dimethyl-3-trifluoroacetyl-1H-pyrrole instead of 3-acetyl-2,4-dimethyl-1H-pyrrole in step 1.

$^1$H-NMR (CDCl$_3$) δ 8.45 (br. s, 1H), 2.50 (s, 3H), 2.19 (s, 3H); MS (EI) m/z 271 (M$^+$), 269 (M$^+$);

2,4-Dimethyl-3-trifluoroacetyl-5-(4-pyridyl)-1H-pyrrole

The title compound was prepared according to the procedure of Example 45 (Method C) using 2-bromo-3,5-dimethyl-4-trifluoroacetyl-1H-pyrrole instead of 3-acetyl-5-bromo-2,4-dimethyl-1H-pyrrole in step 2.

mp 169–170° C.; $^1$H-NMR (CDCl$_3$) δ 10.3 (br. s, 1H), 8.52 (d, J=4.8 Hz, 2H), 7.34 (dd, J=4.6 Hz, 1.7 Hz, 2H), 2.61 (s, 3H), 2.42 (s, 3H); MS (EI) m/z 268 (M$^+$); IR (KBr) 3000, 1665, 1605, 1475, 1440, 1425, 1280, 1200, 1160, 1040, 1000, 920, 830, 735 cm$^{-1}$; Anal. Calcd for $C_{13}H_{11}N_2OF$: C, 58.21; H. 4.13; N, 10.44. Found: C, 57.91; H, 4.08; N, 10.37.

Example 86

3,6-Dimethyl-4-oxo-2-(4-pyridyl)-4,5,6,7-tetrahydro-1H-indole

According to the literature procedure (Chiswell, B. *Inorganica Chimica Acta*. 1972, 629), a mixture of 1-hydroxyimino-1-(4-pyridyl)-2-propanone (Tanaka, A et. al., *Chem. Pharm. Bull*., 1992, 40, 3206) (0.49 g, 3.0 mmol), 5-methyl-1,3-cyclohexanedione (0.38 g, 3.0 mmol), glacial acetic acid (2.4 mL) and H$_2$O (0.6 mL) was stirred vigorously at room temperature. To this flask, zinc dust (0.6 g) was added slowly keeping the temperature below 60° C. Afer addition, the resulting brown solution was heated under reflux condition for 2 hours. After cooling down to room temperature, the reaction mixture was basified by an addition of 2 M aqueous NaOH, then filtered. The filtrate was extracted with CH$_2$Cl$_2$ (20 mL×3), the combined organic layer was dried over MgSO$_4$, and concentrated in vacuo. The residue was purified by flash chromatography (1–5:1 EtOAc-Hexane then EtOAc only) to give the desired product (0.12 g, 17% yield).

mp 247–248° C.; $^1$H-NMR (CDCl$_3$) δ 8.59 (dd, J=4.6 Hz, 1.6 Hz, 3H), 7.31 (dd, J=4.6 Hz, 1.6 Hz, 2H), 2.95–2.86 (m, 1H), 2.60–2.30 (m, 3H), 2.54 (s, 3H), 2.30–2.19 (m, 1H), 1.16 (d, J=6.2 Hz, 3H); IR (KBr) 2950, 1650, 1600, 1520, 1480, 1420, 1380, 1220, 1070, 995, 835, 680 cm$^{-1}$; MS (EI) m/z 240 (M$^+$); Anal. Calcd for $C_{15}H_{16}N_2O$ 0.1H$_2$O: C, 74.42; H, 6.74; N, 11.57. Found: C, 74.18; H, 6.80; N,11.23.

Example 87

3-Methyl-4-oxo-2-(4-pyridyl)-6-thia-4,5,6,7-tetrahydro-1H-indole

According to the literature procedure (Chiswell, B. *Inorganica Chimica Acta*. 1972, 629), a mixture of 1-hydroxyimino-1-(4-pyridyl)-2-propanone (0.45 g, 2.7 mmol), thiacyclohexane-3,5-dione (Terasawa, T., Okada, T., *J. Org. Chem*. 1977, 42, 1163) (0.39 g, 3.0 mmol), glacial acetic acid (2.4 mL) and H$_2$O (0.6 mL) was stirred vigorously at room temperture. To this flask, zinc dust (0.6 g) was added slowly keeping the temperature below 60° C. After addition, the resulting brown solution was heated under reflux condition for 2 hours. After cooling down to room temperature, the reaction mixture was basified by an addition of 2 M aqueous NaOH, then filtered. The filtrate was extracted with CH$_2$Cl$_2$ (20 mL×3), the combined organic layer dried over MgSO$_4$, and concentrated in vacuo. The residue was purified by column chromatography (2–4:1 ethyl acetate-Hexane then EtOAc only) then recystallization from hot ethyl acetate and hexane to afford the title compound (0.10 g, 15% yield).

mp 209–210° C.; $^1$H-NMR (CDCl$_3$) δ 8.98 (br s, 1H), 8.60 (dd, J=4.6, 1.7 Hz, 2H), 7.31 (dd, J=4.6, 1.7 Hz, 2H), 3.86 (s, 2H), 3.41 (s, 2H), 2.52 (s, 3H); IR (KBr) 2900, 2750, 1640, 1600, 1480, 1420, 1370, 1060, 1000, 830 cm$^{-1}$; MS (EI) m/z 244 (M$^+$); Anal. Calcd for $C_{13}H_{12}N_2OS$: C, 63.91; H. 4.95; N, 11.47. Found: C, 64.11; H, 5.06; N, 11.37.

Example 88

3Acetyl-2-formyl-4-methyl-5-(4-pyridyl)-1H-pyrrole

3-Acetyl-2,4-dimethyl-5-(4-pyridyl)-1H-pyrrole (800 mg, 3.74 mmol) was dissolved with THF (37 mL), acetic acid (45 mL) and water (37 mL). Ammonium cerium(IV) nitrate (8.38 g, 15.3 mmol) was added to the mixture at room temperature and stirred for 1.5 hours. The mixture was neutralized with 2 M aqueous NaOH solution and extracted with ethyl acetate (150 mL×3). The combined organic layers were washed with brine, dried over $MgSO_4$, and evaporated in vacio. The residue was purified by flash chromatography eluting with ethyl acetate-hexane (2:1) to afford the title compound (190 mg, 22% yield) as a solid.

mp: 208–209° C.; IR(KBr) v 1660, 1600, 1470, 1430, 1280, 1250, 840 $cm^{-1}$; $^1$H-NMR $(CDCl_3)\delta$ 3 10.07 (s, 1H), 9.99 (s, 1H), 8.72 (dd, J=4.4 Hz, 1.5 Hz, 2H), 7.39 (dd, J=4.4 Hz, 1.5 Hz, 2H), 2.65 (s, 3H), 2.45 (s, 3H); Anal. Calcd. for $C_{13}H_{12}N_2O_2$ $0.1H_2O$: C, 67.87; H, 5.35; N, 12.18. Found: C, 67.81; H, 5.33; N, 11.95.

Example 89

3-Acetyl-2-hydroxymethyl-4-methyl-5-(4-pyridyl)-1H-pyrrole

To a stirred solution of 3-acetyl-2-formyl-4-methyl-5-(4-pyridyl)-1H-pyrrole (84 mg, 0.37 mmol) in $CH_2Cl_2$ (2 mL) and methanol (2 mL) was added sodium borohydride (14 mg, 0.37 mmol) at 0° C. and stirred for 30 minutes at room temperature. The mixture was poured into water (15 mL) and extracted with ethyl acetate-ethanol (10:1, 20 mL×3). The combined organic layers were washed with brine, dried over $MgSO_4$, and evaporated in vactio. Recrystallization from ethyl acetate provided the title compound (20 mg, 24% yield) as a solid.

mp: 163–165° C.; $^1$H-NMR $(CDCl_3)$ δ 9.20 (s, 1H), 8.87–8.58 (m, 2H), 7.35–7.20 (m, 2H), 4.80 (s, 2H), 2.53 (s, 3H), 2.48 (s, 3H); IR(KBr) v 1640, 1600, 1580, 1480, 1370, 1060, 1000, 940, 830 $cm^{-1}$; Anal. Calcd. for $C_{13}H_{14}N_2O_2$ $0.4H_2O$: C, 65.75; H, 6.28; N, 11.80. Found: C, 65.97; H, 6.16; N, 11.53.

Example 90

4-Methyl-3-(3-methylbutanoyl)-2,5-di(4-pyridyl)-1H-pyrrole

The title compound was prepared according to the procedure of Example 1 using 6-methyl-2,4-heptanedione instead of 2,4-pentanedione.

mp 199–201° C.; $^1$H-NMR (DMSO-$d_6$) d 11.96 (br.s, 1H), 8.68–8.52 (m, 4H), 7.58–7.40 (m, 4H), 2.35 (d, J=7.0 Hz, 2H), 2.31 (s, 3H), 2.08–1.90 (m, 1H), 0.75 (d, J=6.6 Hz, 6H); Anal. Calcd. for $C_{20}H_{21}N_3O$: C, 75.21 H, 6.63; N, 13.16. Found: C, 75.08; H, 6.61; N, 13.19.

Example 91

Methyl 4-Methyl-2-phenyl-5-(4-pyridyl)pyrrole-3-carboxylate

Methyl 4-Methyl-2-phenylpyrrole-3-carboxylate

A mixture of N-(benzotriazol-1-yl-methyl)-α-(methylthio)phenylimine (Katritzky, A. R. et. al., Tetrahedron, 1995, 51, 13271) (1.65 g, 5.84 mmol), methyl 3-oxobutanoate (878 mg, 8.77 mmol) and 60% NaH in oil (701 mg, 17.5 mmol) in THF (20 mL) and DMSO (5 mL) was stirred for 4 hours at room temperature. An excess NaH was quenched with water carefully. The mixture was diluted with diethyl ether (150 mL), washed with aqueous 10% NaOH (50 mL×3), dried over $MgSO_4$, and concentrated in vaczio. The residue was purified by flash chromatography eluting with ethyl acetate-hexane (1:5) to afford the subtitle compound (973 mg, 78% yield) as an oil.

$^1$H-NMR $(CDCl_3)$ δ:8.31 (s, 1H), 7.47–7.25 (m, 5H), 6.53 (s, 1H), 3.67 (s, 3H), 2.29 (s, 3H).

Methyl 5-Bromo-4-methyl-2-phenylpyrrole-3-carboxylate

To a solution of methyl 4-methyl-2-phenylpyrrole-3-carboxylate (74 mg, 0.341 mmol) in TEF (1.5 mL) was added NBS (67 mg, 0.375 mmol) at −78° C. After being stirred for 0.25 hour at the same temperature, the mixture was allowed to warm to room temperature. The mixture was poured into ice-water (5 mL). The whole was extracted with ethyl acetate (20 mL), dried over $Na_2SO_4$ and concentrated in vacuo. The residual oil was purified by flash chromatography eluting with ethyl acetate-hexane (1:8) to afford the subtitle compound (97 mg, 96% yield) as crystals.

$^1$H-NMR $(CDCl_3)$ δ:8.44 (br.s, 1H), 7.43–7.25 (m, 5H), 3.66 (s, 3H), 2.23 (s, 3H).

Methyl 4-Methyl-2-phenyl-5-(4-pyridyl)pyrrole-3-carboxylate

A mixture of methyl 5-bromo-4-methyl-2-phenylpyrrole-3-carboxylate (82 mg, 0.278 mmol), 4-pyridylboronic acid (68 mg, 0.556 mmol), $PdCl_2(PPh_3)_2$ (20 mg, 0.0278 mmol), and saturated aqueous $NaHCO_3$ (0.3 mL) in dimethoxy-ethane (1.5 mL) was refluxed for 16 hours. The mixture was extracted with $CH_2Cl_2$ (10 mL×3), the combined organic layer dried over $Na_2SO_4$, and concentrated ini vacito. The residue was purified by PTLC (1 mm) with acetone-hexane (1:2) to afford the title compound (37 mg, 46% yield).

mp: 202–204° C.; $^1$H-NMR $(CDCl_3)$ δ: 9.72 (br.s, 1H), 8.46 (br.s, 2H), 7.66–7.26 (m, 7H), 3.70 (s, 3H), 2.49 (s, 3H); IR(KBr) v: 3450, 1700, 1600, 1470, 1440, 1260, 1080, 700 $cm^{-1}$; MS (EI) m/z 292 ($M^+$); Anal. Calcd. for $C_{18}H_{15}N_3O_2$ $0.2C_4H_{10}O$ $0.1H_2O$: C; 73.09, H; 5.94, N; 9.07; Found: C, 73.12, H; 5.44, N; 8.72.

Example 92

(6RS)-6-Methyl-1,3-di(4-pyridyl)-6,7-dihydro-2H-pyrano[3.4-c]-4-one

A mixture of 4-pyridinecarboxaldehyde (2.09 g, 19.5 mmol), 5,6-dihydro-4-hydroxy-6-methyl-2H-pyran-2-one (1.00 g, 7.80 mmol), and 25% ammonia solution (2.0 mL) in ethanol (5 mL) was refluxed for 7 hours. After cooling to room temperature, the mixture was concentrated ini vacuo. The residual oil was purified by flash chromatography eluting with methanol-$CH_2Cl_2$(1:15) to afford 108 mg. Recrystallized form ethyl acetate-hexane gave the title compound (60 mg, 2.5% yield).

mp: >280° C.; $^1$H-NMR (DMSO-$d_6$) δ: 12.39 (br.s, 1H), 8.53–8.46 (m, 4H), 7.26–7.13 (m, 4H), 4.74 (ddq, J=, 11.4, 6.2, and 3.9 Hz, 1H), 3.04 (dd, J=16.5 and 3.9 Hz, 1H), 2.88 (dd, J=16.5 and 11.4 Hz, 1H), 1.44 (d, J=6.2 Hz, 3H); IR(KBr) v: 3450, 1680, 1600, 1580, 1480, 1420, 1380, 1080, 1040, 820 $cm^{-1}$; Anal. Calcd. for $C_{18}H_{15}N_3O_2$ $0.2$ $C_4H_8O_2$: C; 69.92, H; 5.18, N; 13.01. Found: C; 69.54, H; 5.19, N; 13.01

Example 93

Ethyl 2,4-Dimetyl-5-(4-pyridyl)pyrrole-3-carboxylate

The title compound was prepared according to the procedure of Example 45 (Method C) using ethyl 5-bromo-2,4-dimetylpyrrole-3-carboxylate (Cordell, G. A, J. Org. Chem., 1975, 40, 3161) instead of 3-acetyl-5-bromo-2,4-dimethyl-1H-pyrrole in step 2.

mp: 180–181.5° C.; $^1$H-NMR $(CDCl_3)$ δ: 9.18 (br.s, 1H), 8.54(d, J=4.4Hz, 1H), 8.53 (d, J=4.8 Hz, 1H), 7.31 (d, J=4.8 Hz, 1H), 7.30 (d, J=4.4 Hz, 1H), 4.31 (q, J=7.0 Hz, 2H), 2.57 (s, 3H), 2.47 (s, 3 H), 1.37 (t, J=7.0 Hz, 3H); IR(KBr) v:

3450, 1690, 1600, 1430, 1260, 1100, 1000, 830 cm$^{-1}$; Anal. Calcd for $C_{14}H_{16}N_2O_2$ 0.1$H_2O$: C; 68.33, H; 6.64, N; 11.38. Found: C; 68.00, H; 6.66, N; 11.30.

Example 94

Methyl 2-(2-Methoxyethyl)-4-methyl-5-(4-pyridyl)pyrrole-3-carboxyalte

To a solution of 1-hydroxyimino-1-(4-pyridyl)-2-propanone (500 mg, 3.05 mmol) in glacial acetic acid (18 mL) was added methyl 5-methoxy-3-oxopentanoate (634 mg, 3.96 mmol) at room temperature. Zn powder (597 mg, 9.14 mmol) was added to the mixture at room temperature and the mixture was heated for 1 hour at 100° C. The mixture was filtered through a pad of Celite and the pad was washed with acetic acid thoroughly. The filtrate was evaporated to give a oily residue, which was purified by flash chromatography eluting with acetone-hexane (1:2) to afford the title compound (220 mg, 26% yield).

mp: 177–179° C.; $^1$H-NMR (CDCl$_3$) δ: 9.81 (br.s, 1H), 8.56–8.53 (m, 2H), 7.29–7.27 (m, 2H), 3.83 (s, 3H), 3.72 (t, J=5.7 Hz, 2H), 3.41 (s, 3H), 3.29 (t, J=5.7 Hz, 2 H), 2.45 (s, 3H); IR(KBr) v: 3450, 1690, 1610, 1480, 1360, 1260, 1120, 1000, 830 cm$^{-1}$; Anal. Calcd. for $C_{15}H_{18}N_2O_3$: C; 65.68, H; 6.61, N; 10.21. Found: C; 65.79, H; 6.65, N; 10.13.

Example 95

Metyl 2,5-di(4-Pyridyl)pyrrole-3-carboxylate

The title compound was prepared according to the procedure of Example 10 using methyl 3-methoxyacrylate instead of ethyl propionylacetate.

mp: >270° C.; $^1$H-NMR (DMSO-d6) δ: 12.40 (br.s, 1H), 8.53 (d, J=5.9 Hz, 2H), 8.42 (d, J=6.2 Hz, 2H), 7.75 (s, 1H), 7.23 (d, J=4.8 Hz, 2H), 7.09 (d, J=5.5 Hz, 2H), 3.66 (s, 3H); IR(KBr) v: 3450, 1700, 1600, 1430, 1420, 1350, 1190, 830 cm$^{-1}$; Anal. Calcd. for $C_{16}H_{13}N_3O_2$ 0.5 $H_2CO_3$: C; 63.87, H; 4.55, N; 13.54. Found: C; 63.56, H; 4.45, N; 13.81.

In addition, the chemical structures of the compounds prepared in the above Working Examples are summarized in the following Table. In Table, the following abbreviations are used: Me for methyl, Et for ethyl or Ph for phenyl, and $R^2$ is attached to the 4-position of the pyrrole ring and $R^3$ is attached to the 3-position of the pyrrole ring.

| Ex. | $R^1$ | $R^2$ | $R^3$ | $R^4$ | $(R^5)_m$ |
|---|---|---|---|---|---|
| 1 | H | Me | acetyl | 4-pyridyl | — |
| 2 (dihydrochloride monohydrate) | H | Me | acetyl | 4-pyridyl | — |
| 3 | H | Et | propanoyl | 4-pyridyl | — |
| 4 | H | F$_3$C— | acetyl | 4-pyridyl | — |
| 5 | H | Me | propanoyl | 4-pyridyl | — |
| 6 | H | Me | pentanoyl | 4-pyridyl | — |
| 7 | H | phenyl | acetyl | 4-pyridyl | — |
| 8 | H | Me | acetyl | 4-quinolyl | (CH=CH—CH=CH)— |
| 9 | H | Me | acetyl | 4-pyridyl | (CH=CH—CH=CH)— |
| 10 | H | Et | Et—O—C(O)— | 4-pyridyl | — |
| 11 | H | Me | Et—O—C(O)— | 4-pyridyl | — |
| 12 | H | Me | Me—O—C(O)— | 4-pyridyl | — |
| 13 | H | Me | Ph—CH$_2$—O—C(O)— | 4-pyridyl | — |
| 14 | H | Me | allyloxy-C(O)— | 4-pyridyl | — |
| 15 | H | Me | (CH$_3$)$_2$CH—O—C(O)— | 4-pyridyl | — |
| 16 | H | Me | (CH$_3$)$_3$C—O—C(O)— | 4-pyridyl | — |
| 17 | H | Me | CH$_3$(CH$_2$)$_2$O—C(O)— | 4-pyridyl | — |
| 18 | H | Ph | Et—O—C(O)— | 4-pyridyl | — |
| 19 | H | Me | butoxy-C(O)— | 4-pyridyl | — |
| 20 | H | Me | MeO(CH$_2$)$_2$O—C(O)— | 4-pyridyl | — |
| 21 | H | propyl | Et—O—C(O)— | 4-pyridyl | — |
| 22 | H | (CH$_3$)$_2$CH— | Et—O—C(O)— | 4-pyridyl | — |
| 23 | H | butyl | Et—O—C(O)— | 4-pyridyl | — |
| 24 | H | MeO—CH$_2$— | Me—O—C(O)— | 4-pyridyl | — |
| 25 | H | nitro-Ph | Et—O—C(O)— | 4-pyridyl | — |
| 26 | H | Me | formyl | 4-pyridyl | — |
| 27 | H | Me | methanesulfonyl | 4-pyridyl | — |
| 28 | H | Et | acetyl | 4-pyridyl | — |
| 29 | H | propyl | acetyl | 4-pyridyl | — |
| 30 | H | (CH$_3$)$_2$CH— | acetyl | 4-pyridyl | — |
| 31 | H | butyl | acetyl | 4-pyridyl | — |
| 32 | H | MeO—CH$_2$— | acetyl | 4-pyridyl | — |
| 33 | H | HO—CH$_2$— | acetyl | 4-pyridyl | — |
| 34 | H | Me | CH$_3$CH(OH)— | 4-pyridyl | — |
| 35 (hydrogen chloride) | H | Me | CH$_3$O—N=C(CH$_3$)— | 4-pyridyl | — |
| 36 | H | Me | acetyl | 4-pyridyl | — |

-continued

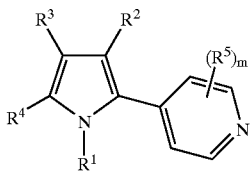

| Ex. | R¹ | R² | R³ | R⁴ | (R⁵)ₘ |
|---|---|---|---|---|---|
| | (N,N'-dioxide) | | | | |
| | H | Me | acetyl | 4-pyridyl | — |
| | (mixture of N-oxide and N'-oxide) | | | | |
| 37 | Me—O—CH₂— | Me | acetyl | 4-pyridyl | — |
| 38 | Me—O—(CH₂)₂— | Me | acetyl | 4-pyridyl | — |
| 39 | H | Me | HO—CH₂— | 4-pyridyl | — |
| 40 | H | Me | H₂N—C(O)— | 4-pyridyl | — |
| 41 | H | Me | HOOC— | 4-pyridyl | — |
| | (morpholinium) | | | | |
| 42 | H | 4-pyridyl | acetyl | Me | — |
| 43 | H | H | acetyl | Me | — |
| 44 | H | Et—O—C(O)— | Me | Ph | — |
| 45 | H | Me | acetyl | Me | — |
| 46 | H | Me | acetyl | Ph | — |
| 47 | H | acetyl | Me | Ph | — |
| 48 | H | Me | acetyl | H | — |
| 49 | H | Me | C(O)—CH₂—CH₂—CH₂— | | — |
| 50 | H | Me | acetyl | Br | — |
| 51 | H | Me | acetyl | F—Ph | — |
| 52 | H | Me | acetyl | 2-thienyl | — |
| 53 | H | CH₂—CH₂—CH₂—C(O)— | | Ph | — |
| 54 | H | C(O)—CH₂—CH₂—CH₂— | | Ph | — |
| 55 | H | Me | C(O)—CH₂—C(CH₃)₂—CH₂— | | — |
| 56 | H | Me | C(O)—CH₂—CHPh—CH₂— | | — |
| 57 | H | Me | cyano | 4-pyridyl | — |
| 58 | H | Me | acetyl | 3-amino-Ph | — |
| 59 | H | Me | acetyl | 2-naphthyl | — |
| 60 | H | Me | acetyl | 4-formyl-Ph | — |
| 61 | H | Me | acetyl | 1-naphthyl | — |
| 62 | H | Me | acetyl | 3-(4-F—Ph—O—)—Ph | — |
| 63 | H | Me | acetyl | 4-Me—O—C(O)—Ph | — |
| 64 | H | Me | acetyl | 3-nitro-Ph | — |
| 65 | H | Me | acetyl | 3-pyridyl | — |
| 66 | H | Me | acetyl | 3-Cl, 4-F—Ph | — |
| 67 | H | Me | acetyl | vinyl | — |
| 68 | H | Me | acetyl | 4-Cl—Ph | — |
| 69 | H | Me | acetyl | 2-furyl | — |
| 70 | H | Me | acetyl | 3-thienyl | — |
| 71 | H | Me | acetyl | 4-Me—S—Ph | — |
| 72 | H | Me | acetyl | 2-F—Ph— | — |
| 73 | H | Me | acetyl | 4-F₃C—Ph | — |
| 74 | H | Me | acetyl | 4-Me—O—Ph— | — |
| 75 | H | Me | acetyl | 4-Me—S(O)—Ph | — |
| 76 | H | Me | acetyl | 4-morpholino | — |
| 77 | H | Me | acetyl | 1-piperidinyl | — |
| 78 | H | Me | acetyl | 4-Ph-piperazin-1-yl | — |
| 79 | H | Me | acetyl | (1,4-dioxa-8-azaspiro[4,5]-decan)-8-yl | — |
| 80 | H | Me | acetyl | cis-2,6-dimethyl morpholin-4-yl | — |
| 81 | H | Me | acetyl | 4-(2-pyridyl) piperazin-1-yl | — |
| 82 | H | Me | | —C(O)C(CH₃)₂(CH₂)₂— | — |
| | H | Me | | —C(O)(CH₂)₂C(CH₃)₂— | — |
| 83 | H | Me | | —C(O)(CH₂)₄— | — |
| 84 | H | Me | acetyl | nitro | — |
| 85 | H | Me | CF₃C(O)— | Me | — |
| 86 | H | Me | | —C(O)CH₂CH(CH₃)CH₂— | — |
| 87 | H | Me | | —C(O)CH₂—S—CH₂— | — |
| 88 | H | Me | acetyl | formyl | — |
| 89 | H | Me | acetyl | OH—CH₂— | — |
| 90 | H | Me | (CH₃)₂CHCH₂C(O)— | 4-pyridyl | — |
| 91 | H | Me | CH₃OC(O)— | Ph | — |
| 92 | H | Me | —C(O)—O—CH(CH₃)CH₂— | 4-pyridyl | — |
| 93 | H | Me | EtOC(O)— | Me | — |

-continued

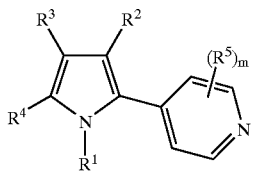

| Ex. | $R^1$ | $R^2$ | $R^3$ | $R^4$ | $(R^5)_m$ |
|---|---|---|---|---|---|
| 94 | H | MeO(CH$_2$)$_2$— | MeOC(O)— | Me | — |
| 95 | H | Me | MeOC(O)— | H | — |

What is claimed is:

1. A compound of the formula:

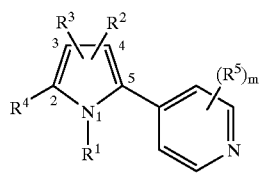

(I)

and its pharmaceutically acceptable salts, wherein
$R^1$ is selected from the following:
  (a) hydrogen, $R^6$—, $R^6$—NH—, hydroxy-$R^6$— or $R^6$—O—$R^6$—;
  (b) $R^6$—CO—, $R^6$—O—CO—$R^6$—, carboxy-$R^6$—, $NH_2$—CO— or $R^6$—NH—CO—; and
  (c) Ar—, Ar—$R^6$—, Ar—NH— or Ar—CO—;
    wherein Ar is selected from phenyl, naphthyl, pyridyl, quinolyl, thienyl, flryl, pyrrolyl, indolyl, benzothienyl and benzofuryl, the aryl or heteroaryl groups being optionally substituted with one or two substituents selected from $C_{1-4}$ alkyl, $C_{1-4}$ alkoxy, halo-substituted $C_{1-4}$ alkyl, halo-substituted $C_{1-4}$ alkoxy, nitro, hydroxy, amino, $R^6$—NH—, $(R^6)_2$N—, halo, formyl, halo-substituted phenoxy, halo-substituted phenyl, $C_{1-4}$ alkyl-substituted phenoxy, halo-substituted phenylthio, $C_{1-4}$ alkoxycarbonyl, $C_{1-4}$ alkylthio and $C_{1-4}$ alkyl-SO—;
    provided $R^1$ is not quinolyl; and
    wherein $R^6$ is $C_{1-6}$ alkyl optionally substituted by up to four halogen atoms;
$R^2$ is selected from the following:
  (d) hydrogen, halo, $R^6$—, $C_{2-6}$ alkenyl, $C_{2-6}$ alkynyl, hydroxy-$R^6$—, $R^6$—O—$R^6$—, mercapto-$R^6$—, $R^6$—S—$R^6$—, —$NH_2$, $R^6$—NH—, $(R^6)_2$—N—, $R^6$—O—, $R^6$—S—, $R^6$—SO— and $R^6$—$SO_2$—;
  (e) 1,4-dioxa-8-azaspiro[4,5]-decanyl,

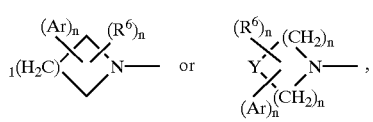

wherein Y is selected from —NH, —N—$R^6$, —N—Ar, O and S; l is 0, 1, 2, 3, 4 or 5; n is independently 0, 1 or 2; and Ar is as defined above;
  (f) Ar—, Ar—$R^6$—, Ar—$C_{2-6}$ alkenyl, Ar—$C_{2-6}$ alkynyl, Ar—O—, Ar—O—$R^6$—, Ar—$R^6$—O—, Ar—S—, Ar—$R^6$—S—, Ar—NH—, (Ar)$_2$—$R^6$—, Ar—$R^6$—NH— or (Ar)$_2$—N—;
  (g) $R^6$—CO—, —$NO_2$, $NH_2$—CO—, $R^6$—NH—CO—, $(R^6)_2$—N—CO—, Ar—CO—, (Ar—$R^6$)$_2$—N—CO—, Ar—$R^6$—CO—, Ar—NH—CO— or Ar—$R^6$—NH—CO—; and
  (h) $R^6$—CO—NH—, Ar—CO—NH—, Ar—$R^6$—CO—NH— or $H_2N$—CO—NH—;
    wherein Ar and $R^6$ are as defined above, provided that $R^2$ is not Ar;
R is $R^6$—CO—;
$R^4$ is pyridyl wherein said pyridyl may optionally be substituted with one or two substituents independently selected from $C_{1-4}$ alkyl, hydroxy, $C_{1-4}$ alkoxy, halo, formyl, fluorophenoxy, methoxycarbonyl, ethoxycarbonyl, methylthio, ethylthio and methyl-SO—;
$R^5$ is independently selected from the following:
  (n) hydrogen, halo, $R^6$—, hydroxy-$R^6$— or $R^6$—O—$R^6$—;
  (o) Ar—, Ar—$R^6$—, Ar—O—, Ar—S—, Ar—NH— or Ar—CO—; and
  (p) $R^6$—CO—, $R^6$—CO— or $R^6$—NH—CO—; or two of $R^5$ which are attached to adjacent carbon atoms on the pyridine ring complete a fused benzene ring, the benzene ring being optionally substituted with one or two substituents selected from $C_{1-4}$ alkyl, halo-substituted $C_{1-4}$ alkyl, halo-substituted $C_{1-4}$ alkoxy, nitro, hydroxy, amino and halo;
    wherein $R^6$ and Ar are as defined above;
m is 0, 1, 2, 3 or 4;
$R^3$ is at position 3; and
the nitrogen atom of the pyridyl ring attached to the 5-position of the pyrrole ring is optionally replaced by a N oxide group.

2. A compound according to claim 1, wherein $R^1$ is selected from group (a); $R^2$ is selected from group (d), (e) or (f), provided that $R^2$ is not Ar; and $R^1$ is selected from group (n); and m is 0, 1 or 2.

3. A compound according to claim 2, wherein $R^1$ is hydrogen, $C_{1-4}$ alkyl, $C_{1-4}$ alkylamino, halo substituted $C_{1-4}$ alkyl, hydroxy-$C_{1-4}$ alkyl, $C_{1-4}$ alkoxyalkyl or halo $C_{1-4}$ alkoxy-$C_{1-4}$ alkyl; $R^2$ is hydrogen, halo, $R^6$—, hydroxy-$R^6$— or $R^6$—O—$R^6$—; $R^5$ is hydrogen, halo, $C_{1-4}$ alkyl or halo substituted $C_{1-4}$ alkyl; and m is 0 or 1.

4. A compound according to claim 3, wherein $R^1$ is hydrogen, $C_{1-4}$ alkyl or $C_{1-4}$ alkoxy-$C_{1-4}$ alkyl; $R^2$ is hydrogen, halo, $C_{1-4}$ alkyl optionally substituted by halo, hydroxy-$C_{1-4}$ alkyl or $C_{1-4}$-alkoxy-$C_{1-4}$ alkyl; $R^3$ is $C_{1-4}$ alkylcarbonyl; and $R^5$ is hydrogen or halo.

5. A compound according to claim 4, wherein $R^1$ is hydrogen, $C_{1-4}$ alkyl or $C_{1-4}$ alkoxy-$C_{1-4}$ alkyl; $R^2$ is $C_{1-4}$ alkyl optionally substituted by halo, hydroxy-$C_{1-4}$ alkyl or $C_{1-4}$-alkoxy-$C_{1-4}$ alkyl; $R^3$ is $C_{1-4}$ alkylcarbonyl; $R^4$ is optionally substituted with $C_{1-4}$ alkoxy, halo, formyl, 4-fluorophenoxy, methoxycarbonyl, ethoxycarbonyl or methylthio; and $R^5$ is hydrogen.

6. A compound according to claim 1, wherein $R^1$ is hydrogen, methyl or methoxyethyl; $R^2$ is methyl, ethyl, monofluoromethyl, difluoromethyl, trifluoromethyl, phenyl, n-propyl, isopropyl, n-bytyl, isobutyl, methoxymethyl, nitrophenyl, hydroxymethyl or pyridyl; $R^3$ is acetyl, propanoyl, or pentanoyl; $R^2$ is at the 4 position of the pyrrole ring; $R^4$ is pyridyl; and $R^5$ is hydrogen.

7. A compound according to claim 1, being one of the following:
3-acetyl-4-methyl-2,5-di(4-pyridyl)-1H-pyrrole;
3-acetyl-4-ethyl-2,5-di(4-pyridyl)-1H-pyrrole;
3-acetyl-2,5-di(4-pyridyl)-4-trifluoromethyl-1H-pyrrole.

8. A process for preparing a compound of the formula:

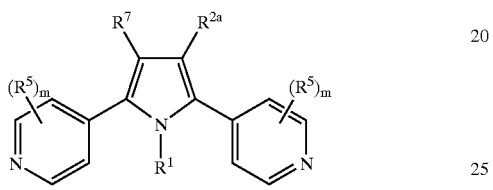

wherein $R^1$, $R^5$ and m are defined in claim 1; $R^{2a}$ are independently hydrogen, $C_{1-6}$ alkyl, $C_{2-6}$ alkenyl, $C_{2-6}$ alkynyl, Ar or Ar—$C_{1-4}$ alkyl; and $R^7$ is —C(O)$R^{3a}$, —C(O)O$R^{3a}$, —CN or —SO$_2R^{3a}$, wherein $R^{3a}$ is hydrogen, $C_{1-6}$ alkyl, $C_{2-6}$ alkenyl, $C_{2-6}$ alkynyl, Ar or Ar—$C_{1-4}$ alkyl,
which comprises reacting a compound of the formula:

with a compound of the formula:

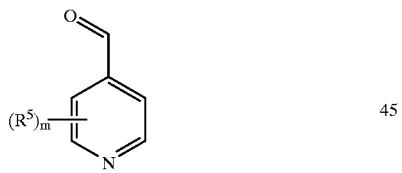

and amine $R^1NH_2$ in a reaction-inert solvent.

9. A pharmaceutical composition for the treatment of cytokine-mediated diseases or CAMs mediated diseases, which comprises a therapeutically effective amount of a compound of the formula:

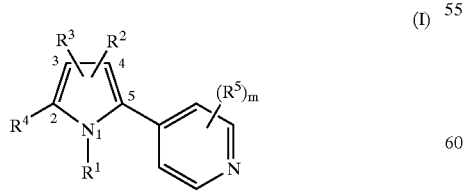

(I)

and its pharmaceutically acceptable salts, wherein
$R^1$ is selected from the following:
(a) hydrogen, $R^6$—, $R^6$—NH—, hydroxy-$R^6$— or $R^6$—O—$R^6$—;

(b) $R^6$—CO—, $R^6$—O—CO—$R^6$—, carboxy-$R^6$—, $NH_2$—CO— or $R^6$—NH—CO—; and
(c) Ar—, Ar—$R^6$—, Ar—NH— or Ar—CO—;
wherein Ar is selected from phenyl, naphthyl, pyridyl, quinolyl, thienyl, furyl, pyrrolyl, indolyl, benzothienyl and benzofuryl, the aryl or heteroaryl groups being optionally substituted with one or two substituents selected from $C_{1-4}$ alkyl, $C_{1-4}$ alkoxy, halo-substituted $C_{1-4}$ alkyl, halo-substituted $C_{1-4}$ alkoxy, nitro, hydroxy, amino, $R^6$—NH—, $(R^6)_2$N—, halo, formyl, halo-substituted phenoxy, halo-substituted phenyl, $C_{1-4}$ alkyl-substituted phenoxy, halo-substituted phenylthio, $C_{1-4}$ alkoxycarbonyl, $C_{1-4}$ alkylthio and $C_{1-4}$ alkyl-SO—;
provided $R^1$ is not quinolyl; and
wherein $R^6$ is $C_{1-6}$ alkyl optionally substituted by up to four halogen atoms;
$R^2$ is selected from the following:
(d) hydrogen, halo, $R^6$—, $C_{2-6}$ alkenyl, $C_{2-6}$ alkynyl, hydroxy-$R^6$—, $R^6$—O—$R^6$—, mercapto-$R^6$—, $R^6$—S—$R^6$—, —$NH_2$, $R^6$—NH—, $(R^6)_2$—N—, $R^6$—O—, $R^6$—S—, $R^6$—SO— and $R^6$—$SO_2$—;
(e) 1,4-dioxa-8-azaspiro[4,5]-decanyl,

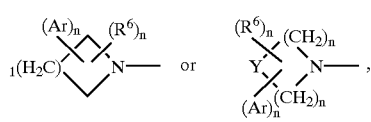

wherein Y is selected from —NH, —N—$R^6$, —N—Ar, 0 and S; l is 0, 1, 2, 3, 4 or 5; n is independently 0, 1 or 2; and Ar is as defined above;
(f) Ar—, Ar—$R^6$—, Ar—$C_{2-6}$ alkenyl, Ar—$C_{2-6}$ alkynyl, Ar—O—, Ar—O—$R^6$—, Ar—$R^6$—O—, Ar—S—, Ar—$R^6$—S—, Ar—NH—, $(Ar)_2$—$R^6$—, Ar—$R^6$—NH— or $(Ar)_2$—N—;
(g) $R^6$—CO—, —$NO_2$, $NH_2$—CO—, $R^6$—NH—CO—, $(R^6)_2$—N—CO—, Ar—CO—, $(Ar—R^6)_2$—N—CO—, Ar—$R^6$—CO—, Ar—NH—CO— or Ar—$R^6$—NH—CO—; and
(h) $R^6$—CO—NH—, Ar—CO—NH—, Ar—$R^6$—CO—NH— or $H_2N$—CO—NH—;
wherein Ar and $R^6$ are as defmed above, provided that $R^2$ is not Ar;
$R^3$ is $R^6$—CO—;
$R^4$ is pyridyl wherein said pyridyl may optionally be substituted with one or two substituents independently selected from $C_{1-4}$ alkyl, hydroxy, $C_{1-4}$ alkoxy, halo, formyl, fluorophenoxy, methoxycarbonyl, ethoxycarbonyl, methylthio, ethylthio and methyl-SO—;
$R^5$ is independently selected from the following:
(n) hydrogen, halo, $R^6$—, hydroxy-$R^6$— or $R^6$—O—$R^6$—;
(o) Ar—, Ar—$R^6$—, Ar—O—, Ar—S—, Ar—NH— or Ar—CO—; and
(p) $R^6$—CO—, $R^6$—O—CO— or $R^6$—NH—CO—; or two of $R^5$ which are attached to adjacent carbon atoms on the pyridine ring complete a fused benzene ring, the benzene ring being optionally substituted with one or two substituents selected from $C_{1-4}$ alkyl, halo-substituted $C_{1-4}$ alkyl, halo-substituted $C_{1-4}$ alkoxy, nitro, hydroxy, amino and halo;

wherein $R^6$ and Ar are as defined above;

m is 0, 1, 2, 3 or 4;

$R^3$ is at position 3; and the nitrogen atom of the pyridyl ring attached to the 5-position of the pyrrole ring is optionally replaced by a N oxide group.

10. A pharmaceutical composition according to claim 9, wherein $R^1$ is selected from group (a); $R^2$ is selected from group (d), (e) or (f), provided that $R^2$ is not Ar; and $R^5$ is selected from group (n); and m is 0, 1 or 2.

11. A pharmaceutical composition according to claim 10, wherein $R^1$ is hydrogen, $C_{1-4}$ alkyl, $C_{1-4}$ alkylamino, halo substituted $C_{1-4}$ alkyl, hydroxy-$C_{1-4}$ alkyl, $C_{1-4}$ alkoxyalkyl or halo $C_{1-4}$ alkoxy-$C_{1-4}$ alkyl; $R^2$ is hydrogen, halo, $R^6$—, hydroxy-$R^6$— or $R^6$—O—$R^6$—; $R^5$ is hydrogen, halo, $C_{1-4}$ alkyl or halo substituted $C_{1-4}$ alkyl; and m is 0 or 1.

12. A pharmaceutical composition according to claim 11, wherein $R^1$ is hydrogen, $C_{1-4}$ alkyl or $C_{1-4}$ alkoxy-$C_{1-4}$ alkyl; $R^2$ is hydrogen, halo, $C_{1-4}$ alkyl optionally substituted by halo, hydroxy-$C_{1-4}$ alkyl or $C_{1-4}$-alkoxy-$C_{1-4}$ alkyl; $R^3$ is $C_{1-4}$ alkylcarbonyl; and $R^5$ is hydrogen or halo.

13. A pharmaceutical composition according to claim 12, wherein $R^1$ is hydrogen, $C_{1-4}$ alkyl or $C_{1-4}$ alkoxy-$C_{1-4}$ alkyl; $R^2$ is $C_{1-4}$ alkyl optionally substituted by halo, hydroxy-$C_{1-4}$ alkyl or $C_{1-4}$-alkoxy-$C_{1-4}$ alkyl; $R^4$ is optionally substituted with $C_{1-4}$ alkoxy, halo, formyl, 4-fluorophenoxy, methoxycarbonyl, ethoxycarbonyl or metht and $R^5$ is hydrogen.

14. A pharmaceutical composition according to claim 10, wherein $R^1$ is hydrogen, methyl or methoxyethyl; $R^2$ is methyl, ethyl, monofluoromethyl, difluoromethyl, trifluoromethyl, phenyl, n-propyl, isopropyl, n-bytyl, isobutyl, methoxymethyl, nitrophenyl, hydroxymethyl or pyridyl; $R^3$ is acetyl, propanoyl, or pentanoyl; $R^4$ is pyridyl; and $R^5$ is hydrogen.

15. A pharmaceutical composition according to claim 10, comprising a compound selected from:

3-acetyl-4-methyl-2,5-di(4-pyridyl)-1H-pyrrole;

3-acetyl-4-ethyl-2,5-di(4-pyridyl)-1H-pyrrole;

3-acetyl-2,5-di(4-pyridyl)-4-trifluoromethyl-1H-pyrrole.

16. A pharmaceutical composition for the treatment of arthritis, sepsis, septic shock, psoriasis, and crohn's disease, which comprises a therapeutically effective amount of a compound of claim 1 and its pharmaceutically acceptable carrier.

17. A method for the treatment of disease conditions caused by cytokine-mediated diseases or CAMs mediated diseases, in a mammalian subject, which comprises administering to said subject a therapeutically effective amount of a compound according to claim 1.

18. A method for the treatment of arthritis, sepsis, septic shock, psoriasis, and crohn's disease, which comprises administering to said subject a therapeutically effective amount of a compound according to claim 1.

* * * * *